US007527972B2

(12) United States Patent
Prabhakar et al.

(10) Patent No.: US 7,527,972 B2
(45) Date of Patent: May 5, 2009

(54) USES OF BISPECIFIC ANTIBODY COATED DENDRITIC CELLS PULSED WITH ANTIGENS AND GM-CSF IN IMMUNE REGULATION

(75) Inventors: Bellur S. Prabhakar, Oak Brook, IL (US); Mark J. Holterman, River Forest, IL (US); Chenthamarakshan Vasu, Chicago, IL (US); Matthew N. Meriggioli, Clarendon Hills, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/560,649

(22) Filed: Nov. 16, 2006

(65) Prior Publication Data

US 2007/0184031 A1    Aug. 9, 2007

Related U.S. Application Data

(63) Continuation-in-part of application No. PCT/US2005/017210, filed on May 16, 2005.

(60) Provisional application No. 60/571,831, filed on May 17, 2004, provisional application No. 60/599,212, filed on Aug. 5, 2004, provisional application No. 60/673,726, filed on Apr. 21, 2005, provisional application No. 60/825,459, filed on Sep. 13, 2006.

(51) Int. Cl.
  *C12N 5/00* (2006.01)
  *A61K 39/00* (2006.01)
  *C12P 21/08* (2006.01)

(52) U.S. Cl. .................. 435/325; 424/136.1; 424/154.1; 530/387.3; 530/388.75

(58) Field of Classification Search ........................ None
See application file for complete search history.

(56) References Cited

U.S. PATENT DOCUMENTS

| 6,475,483 B1 | 11/2002 | Steinman et al. | |
| 6,682,736 B1 * | 1/2004 | Hanson et al. | 424/144.1 |
| 2002/0039581 A1 | 4/2002 | Carreno et al. | |
| 2003/0167502 A1 | 9/2003 | Deo et al. | |

FOREIGN PATENT DOCUMENTS

| WO | WO 02/051430 A | 7/2002 |
| WO | WO 02/055675 A | 7/2002 |

OTHER PUBLICATIONS

International Search Report issued in PCT/US2005/017210 (2006).
Carreno et al., "CTLA-4 (CD152) Can Inhibit T Cell Activation by Two Different Mechanisms Depending on Its Level of Cell Surface Expression," *The Journal of Immunology* 165: 1352-1356 (2000).
Caturegli et al., "Hypothyroidism in Transgenic Mice Expressing IFN-γ in the Thyroid," *PNAS* 97(4): 1719-1724 (2000).
Chai et al., "CD152 Ligation by CD80 on T Cells Is Required for the Induction of Unresponsiveness by Costimulation-Deficient Antigen Presentation," *The Journal of Immunology* 165: 3037-3042 (2000).
Chambers et al., "The Lymphoproliferative Defect in CTLA-4—Deficient Mice is Ameliorated by an Inhibitory NK Cell Receptors," *Blood* 99(12): 4509-4516 (2002).
Dogan et al., "Absence of IL-4, and Not Suppression of the Th2 Response, Prevents Development of Experimental Autoimmune Graves' Disease," *The Journal of Immunology* 170: 2195-2204 (2003).
Griffin et al., "Blockade of T Cell Activation Using a Surface-Linked Single-Chain Antibody to CTLA-4 (CD152)," *The Journal of Immunology* 164: 4433-4442 (2000).
Guinan et al., "Transplantation of Anergic Histoincompatible Bone Marrow Allografts," *The New England Journal of Medicine* 340(22): 1704-1714 (1999).
Hurwitz et al., "Cytotoxic T Lymphocyte Antigen-4 (CTLA-4) Limits the Expansion of Encephalitogenic T Cells in Experimental Autoimmune Encephalomyelitis (EAE)-resistant BALB/c Mice," *PNAS* 99(5): 3013-3017 (2002).
Jonuleit et al., "Induction of Interleukin 10-producing, Nonproliferating CD4+ T Cells with Regulatory Properties by Repetitive Stimulation with Allogeneic Immature Human Dendritic Cells," *J. Exp. Med.* 192(9): 1213-1222 (2000).
Kaithamana et al., "Induction of Experimental Autoimmune Graves' Disease in BALB/C Mice," *The Journal of Immunology* 163: 5157-5164 (1999).
Lazetic et al., "Chimeric Co-stimulatory Molecules That Selectively Act through CD28 or CTLA-4 on Human T Cells," *The Journal of Biological Chemistry* 277(41): 38660-38668 (2002).
Lin et al., "Cytotoxic T Lymphocyte Antigen 4 (CTLA4) Blockade Accelerates the Acute Rejection of Cardiac Allografts in CD28-Deficient Mice: CTLA4 Can Function Independently of CD28," *J. Exp. Med.* 188(1): 199-204 (1998).
Peterson et al., "B7.2 Has Opposing Roles During the Activation Versus Effector Stages of Experimental Autoimmune Thyroiditis," *The Journal of Immunology* 162: 1859-1867 (1999).
Rao et al., "Targeted Delivery of Anti-CTLA-4 Antibody Downregulates T Cell Function in Vitro and in Vivo," *Clinical Immunology* 101(2): 136-145 (2001).

(Continued)

*Primary Examiner*—Ilia Ouspenski
(74) *Attorney, Agent, or Firm*—Barnes & Thornburg LLP; Alice O. Martin

(57) ABSTRACT

GM-CSF administered before immunization exerted a sustained suppressive effect against the induction of myasthenia gravis (MG). This suppression was associated with lowered serum autoantibody levels, reduced T cell proliferative responses to AChR, and an expansion in the population of FoxP3+ regulatory T cells. Manipulating DCs to expand regulatory T cells is useful for the control of autoimmune diseases such as myasthenia gravis MG.

8 Claims, 24 Drawing Sheets

OTHER PUBLICATIONS

Samoilova et al., "B7 Blockade Prevents Activation-Induced Cell Death of Thymocytes," *International Immunology* 9(11): 1663-1668 (1997).

Samoilova et al., "CTLA-4 Is Required for the Induction of High Dose Oral Tolerance," *International Immunology* 10(4): 491-498 (1998).

Stassi et al., "Fas/Fas Ligand-Driven T Cell Apoptosis as a Consequence of Ineffective Thyroid Immunoprivilege in Hashimoto's Thyroiditis," *The Journal of Immunology* 162: 263-267 (1999).

Takeuchi et al., "TGF-β Promotes Immune Deviation by Altering Accessory Signals of Antigen-Presenting Cells," *The Journal of Immunology* 160: 1589-1597 (1998).

Tang et al., "Apoptosis of Thyrocytes and Effector Cells During Induction of Resolution of Granulomatous Experimental Autoimmune Thyroiditis," *International Immunology* 12(12): 1629-1639 (2000).

Thorstenson et al., "Generation of Anergic and Potentially Immunoregulatory CD25+ CD4 T Cells In Vivo After Induction of Peripheral Tolerance with Intravenous or Oral Antigen," *The Journal of Immunology* 167: 188-195 (2001).

Vasu et al., "CD80 and CD86 C Domains Play an Important Role in Receptor Binding and Co-Stimulatory Properties," *International Immunology*, 15(2): 167-175 (2003).

Vasu et al., "Selective Induction of Dendritic Cells Using Granulocyte Macrophage-Colony Stimulating Factor, But Not fms-Like Tyrosine Kinase Receptor 3-Ligand, Activates Thyroglobulin-Specific CD4+/CD25+ T Cells and Suppresses Experimental Autoimmune Thyroiditis," *The Journal of Immunology*, 170: 5511-5522 (2003).

Vasu et al., "Targeted Engagement of CTLA-4 Prevents Autoimmune Thyroiditis," *International Immunology* 15 (5): 641-654 (2003).

Walunas et al., "CTLA-4 Ligation Blocks CD28-dependent T Cell Activation," *J. Exp. Med.* 183: 2541-2550 (1996).

Wei et al., "Expression and Regulation of Fas and Fas Ligand on Thyrocytes and Infiltrating Cells During Induction and Resolution of Granulomatous Experimental Autoimmune Thyroiditis," *The Journal of Immunology* 167: 6678-6686 (2001).

Wells et al., "Signaling throught CD28 and CTLA-4 Controls Two Distinct Forms of T Cell Anergy," *J. Clin. Invest.* 108(6): 895-904 (2001).

Zhang et al., "Activation of CD25+ CD4+ Regulatory T Cells by Oral Antigen Administration," *The Journal of Immunology* 167: 4245-4253 (2001).

Adorini et al., "Tolerogenic Dendritic Cells Induced by Vitamin D Receptor Ligands Enhance Regulatory T Cells Inhibiting Allograft Rejection and Autoimmune Diseases," *Journal of Cellular Biochemistry* 88: 227-233 (2003).

Aruna et al., "Suppression of Myasthenogenic Responses of a T Cell Line by a Dual Altered Peptide Ligand by Induction of CD4+CD25+ Regulatory Cells," *PNAS* 102 (29): 10285-10290 (2005).

Asano et al., "Autoimmune Disease as a Consequence of Developmental Abnormality of a T Cell Subpopulation," *J. Exp. Med.* 184: 387-396 (1996).

Balasa et al., "Is Pathogenic Humoral Autoimmunity a Th1 Response? Lessons from (for) Myasthenia Gravis," *Viewpoint Immunology Today* 21(1): 19-23 (2000).

Batteux et al., "Curative Treatment of Experimental Autoimmune Thyroiditis by In Vivo Adminstration of Plasmid DNA Coding for Interleukin-10," *Eur. J. Immunol.* 29: 958-963 (1999).

Brocke et al., "In Vitro Proliferative Responses and Antibody Titers Specific to Human Acetylcholine Receptor Synthetic Peptides in Patients with Myasthenia Gravis and Relation to HLA Class II Genes," *J. Clin. Invest.* 82: 1894-1900 (1988).

Dieckmann et al., "Human CD+CD25+ Regulatory, Contact-Dependent T Cells Induce Interleukin 10-Producing, Contact-Independent Type 1-Like Regulatory T Cells," *J. Exp. Med.* 196 (2): 247-253 (2002).

Drachman, "Myasthenia Gravis," *The New England Journal of Medicine* 330 (25): 1797-1810 (1994).

Duan et al., "Protective Potential of Experimental Autoimmue Myasthenia Gravis in Lewis Rats by IL-10-Modified Dendritic Cells," *Neurobiology of Disease* 16: 461-467 (2004).

Gad et al., "Dendritic Cells in Peripheral Tolerance and Immunity," *APMIS* 111: 766-775 (2003).

Goulvestre et al., "Chemokines Modulate Experimental Autoimmune Thyroiditis Through Attraction of Autoreactive or Regulatory T Cells," *Eur. J. Immunol.* 32: 3435-3442 (2002).

Groux et al., "The Complex Role of Interleukin-10 in Autoimmunity," *Journal of Autoimmunity* 20: 281-285 (2003).

Groux et al., "Role of Dendritic Cells in the Generation of Regulatory T Cells," *Seminars in Immunology* 16: 99-106 (2004).

Hackstein et al., "Designer Dendritic Cells for Tolerance Induction: Guided Not Misguided Missiles," *Trends in Immunology* 22 (8): 437-442 (2001).

Hamilton et al., "Spatial Correlation Between Thyroid Epithelial Cells Expressing Class II MHC Molecules and Interferon-Gamma-Containing Lymphocytes in Human Thyroid Autoimmune Disease," *Clin. Exp. Immunol.* 83: 64-68 (1991).

Hara et al., "IL-10 Is Required for Regulatory T Cells to Mediate Tolerance to Alloantigens In Vivo," *The Journal of Immunology* 166: 3789-3796 (2001).

Horwitz et al., "The Role of the Combination of IL-2 and TGF-Beta or IL-10 in the Generation and Function of CD4+CD25+ and CD8+ Regulatory T Cells Subsets," *Journal of Leukocyte Biology* 74: 471-478 (2003).

Jonuleit et al., "Dendritic Cells as a Tool to Induce Angergic and Regulatory T Cells," *Trends in Immunology* 22 (7): 394-400 (2001).

Jonuleit et al., "Infectious Tolerance: Human CD25+ Regulatory T Cells Convey Suppressor Activity to Conventional CD4+ T Helper Cells," *J. Exp. Med.* 196 (2): 255-260 (2002).

Karachunski et al., "Absence of IFN-Gamma or IL-12 Has Different Effects on Experimental Myasthenia Gravis in C57BL/6 Mice," *The Journal of Immunology* 164: 5236-5244 (2000).

Kingsley et al., "CD25+CD4+ Regulatory T Cells Prevent Graft Rejection: CTLA-4- and IL-10-Dependent Immunoregulation of Alloresponses," *The Journal of Immunology*, 168: 1080-1086 (2002).

Kuwana, "Induction of Anergic and Regulatory T Cells by Plasmacytoid Dendritic Cells and Other Dendritic Cells Subsets," *Human Immunology*, 63: 1156-1163 (2002).

Levings et al., "T-Regulatory 1 Cells: A Novel Subset of CD4+ T Cells with Immunoregulatory Properties," *J. Allergy Clin. Immunol.* 106 (1): S109-S112 (2000).

Levings et al., "The Role of IL-10 and TGF-Beta in the Differentiation and Effector Function of T Regulatory Cells," *Int. Arch Allergy Immunol.* 129: 263-276 (2002).

Li et al., "Experimental Study in Induction of Tolerance to Experimental Autoimmune Myasthenia Gravis by Immature Dendritic Cells," *Journal of Huazhong University of Science and Technology [Med Sci]* 25 (2): 215-218 (2005).

Lutz et al., "Immature Dendritic Cells Generated with Low Doses of GM-CSF in the Absence of IL-4 Are Maturation Resistant and Prolong Allograft Survival In Vivo," *Eur. J. Immunol.* 30: 1813-1822 (2000).

Lutz et al., "Immature, Semi-Mature and Fully Mature Dendritic Cells: Which Signals Induce Tolerance or Immunity?," *Trends in Immunology* 23 (9): 445-449 (2002).

Mahnke et al., "Induction of CD4+/CD25+ Regulatory T Cells by Targeting of Antigens to Immature Dendritic Cells," *Blood* 101 (12): 4862-4869 (2003).

Maldonado-Lopez et al., "CD8 Alpha+ and CD8 Alpha- Subclasses of Dendritic Cells Direct the Development of Distinct T Helper Cells In Vivo," *J. Exp. Med.* 189 (3): 587-592 (1999).

Maldonado-Lopez et al., "Role of CD8 Alpha+ and CD8 Alpha- Dendritic Cells in the Induction of Primary Immune Reponses In Vivo," *J. Leukoc. Biol.* 66: 242-246 (1999).

Maldonado-Lopez et al., "Cytokines Regulate the Capactiy of CD8 Alpha+ and CD8 Alpha- Dendritic Cells to Prime Th1/Th2 Cells In Vivo," *The Journal of Immunology* 167: 4345-4350 (2001).

Menges et al., "Repetitive Injections of Dendritic Cells Matured with Tumor Necrosis Factor Alpha Induce Antigen-Specific Protection of Mice from Autoimmunity," *J. Exp. Med.* 195 (1): 15-21 (2002).

Mignon-Godefroy et al., "Curative and Protective Effects of IL-10 in Experimental Autoimmune Thyroiditis (EAT)," *The Journal of Immunology* 154: 6634-6643 (1995).

Min et al., "Inhibitory Feedback Loop Between Tolerogenic Dendritic Cells and Regulatory T Cells in Transplant Tolerance," *The Journal of Immunology* 170: 1304-1312 (2003).

Montani et al., "Regulation of Major Histocompatibility Class II Gene Expression in FRTL-5 Thyrocytes: Opposite Effects of Interferon and Methimazole," *Endocrinology* 139 (1): 290-302 (1998).

Morel et al., "Dendritic Cells, T Cell Tolerance and Therapy of Adverse Immune Reactions," *Clin. Exp. Immunol.* 133: 1-10 (2003).

Morelli et al., "Dendritic Cells: Regulators of Alloimmunity and Opportunities for Tolerance Induction," *Immunological Reviews* 196: 125-146 (2003).

Morris et al., "CD 137 Signaling Interferes with Activation and Function of CD4+CD25+ Regulatory T Cells in Induced Tolerance to Experimental Autoimmune Thyroiditis," *Cellular Immunology* 226: 20-29 (2003).

Moser, "Dendritic Cells in Immunity and Tolerance—Do They Display Opposite Functions?," *Immunity* 19: 5-8 (2003).

Nagane et al., "Dendritic Cells in Hyperplastic Thymuses from Patients with Myasthenia Gravis," *Muscle Nerve* 27: 582-589 (2003).

O'Garra et al., "Regulatory T Cells and Mechanisms of Immune System Control," *Nature Medicine* 10 (8): 801-805 (2004).

O'Keeffe et al., "Effects of Administration of Progenipoietin 1, Flt-3 Ligand, Granulocyte Colong-Stimulating Factor, and Pegylated Granulocyte-Macrophage Colony-Stimulating Factor on Dendritic Cell Subsets in Mice," *Blood*. 99 (6): 2122-2130 (2002).

Piccirillo et al., "Cornerstone of Peripheral Tolerance: Naturally Ocurring CD4+CD25+ Regulatory T Cells," *Trends in Immunology* 25 (7): 374-380 (2004).

Pinkoski et al., "Murder by Proxy," *Nature Immunology* 1 (6): 461-462 (2000).

Pujol-Borrell et al., "Inappropriate Major Histocompatibility Complex Class II Expression by Thyroid Follicular Cells in Thyroid Autoimmune Disease and by Pancreatic Beta Cells in Type I Diabetes," *Mol. Biol. Med.* 3: 159-165 (1986).

Roncarolo et al., "Type 1 T Regulatory Cells," *Immunological Reviews*. 182: 68-79 (2001).

Rossi et al., "Human Dendritic Cells: Potent Antigen-Presenting Cells at the Crossroads of Innate and Adaptive Immunity," *The Journal of Immunology* 175: 1373-1381 (2005).

Rutella et al., "Regulatory T Cells and Tolerogenic Dendritic Cells: from Basic Biology to Clinical Applications," *Immunology Letters* 94: 11-26 (2004).

Shevach et al., "Regulatory T Cells in Autoimmunity," *Annu. Rev. Immunol.* 18: 423-499 (2000).

Stafford et al., "Newer Insights into the Pathogenesis of Experimental Autoimmune Thyroiditis," *Intern. Rev. Immunol.* 19: 501-533 (2000).

Stassi et al., "Control of Target Cell Survival in Thyroid Autoimmunity by T Helper Cytokines Via Regulation of Apoptotic Proteins," *Nature Immunology* 1 (6): 483-488 (2000).

Stassi et al., "Autoimmune Thyroid Disease: New Models of Cell Death in Autoimmunity," *Nature Reviews Immunology* 2: 195-204 (2002).

Thompson et al., "Regulatory T Cells," *Current Opinion in Pharmacology* 4: 408-414 (2004).

Tourneur et al., "IL-10 Is Necessary for FasL-Induced Protection from Experimental Autoimmune Thyroiditis But Not for FasL_Induced Immune Deviation," *Eur. J. Immunol.* 32: 1292-1299 (2002).

Vasu et al., "Modulation of Dendritic Cell Function and Cytokine Production to Prevent Thyroid Autoimmunity," *Autoimmunity* 36 (6-7): 389-396 (2003).

Vincent et al., "Myasthenia Gravis," *The Lancet* 357 (9274): 2122-2128 (2001).

Vincent et al., "Unravelling the Pathogenesis of Myasthenia Gravis," *Immunology* 2: 797-804 (2002).

Wakkach et al., "Characterization of Dendritic Cells that Induce Tolerance and T Regulatory 1 Cell Differentiation In Vivo," *Immunity* 18: 605-617 (2003).

Wang et al., "A Unique Combination of Inflammatory Cytokines Enhances Apoptosis of Thyroid Follicular Cells and Transforms Nondestructive to Destructive Thyroiditis in Experimental Autoimmune Thyroiditis," *The Journal of Immunology* 168: 2470-2474 (2002).

Weetman et al., "Autoimmune Thyroid Disease: Further Developments in Our Understanding," *Endocrine Reviews* 15 (6): 788-830 (1994).

Xiao et al., "Induction of Peripheral Tolerance to Experimental Autoimmune Myasthenia Gravis by Acetylcholine Receptor-Pulsed Dendritic Cells," *Cellular Immunology* 223: 63-69 (2003).

Zhang et al., "Noninvolvement of IL-4 and IL-10 in tolerance Induction to Experimental Autoimmune Thyroiditis," *Cellular Immunology* 187: 95-102 (1998).

Zhang et al., "Gene Therapy of Experimental Autoimmune Thyroiditis Mice by In Vivo Administration of Plasmid DNA Coding for Human Interleukin-10," *Acta Pharmacol. Sin.* 24 (9): 885-890 (2003).

Zhang et al., "IL-10 Is Involved in the Suppression of Experimental Autoimmune Encephalomyelitis by CD25+CD4+ Regulatory T Cels," *International Immunology* 16 (2): 249-256 (2004).

Zheng et al., "Natural and Induced CD4+CD25+ Cells Educate CD4+CD25- Cells to Develop Suppressive Activity: The Role of IL,2, TGF-Beta, and IL-10," *The Journal of Immunology* 172: 5213-5221 (2004).

Banchereau et al., "Denritic cells and the control of immunity," *Nature*, 392 (6673): 245-252 (1998).

Cobbold, "T cell toleranc in transplantation; possibilities for therapeutic intervention," *Expert Opinion on Therapeutic Targets*, 6 (5): 583-599 (2002).

Panoutsakopoulou et al., "Suppression of autoimmune disease after vaccination with autoreactive T cells that express Qa-1 peptide complexes," *J. Clin. Invest.*, 113 (8): 1218-1224 (2004).

Rastellini et al., "Granulocyte/macrophage colony-stimulating factor-stimulated hepatic dendritic cell progenitors prolong pancreatic islet allograft survival," *Transplantation*, 60 (11): 1366-1370 (1995).

European Search Report issued in EP 05 74 9769 (2008).

* cited by examiner

A.

B.

USES OF BISPECIFIC ANTIBODY COATED DENDRITIC CELLS PULSED WITH ANTIGENS AND GM-CSF IN IMMUNE REGULATION

CROSS-REFERENCE TO RELATED PATENT APPLICATIONS

This patent application claims priority to U.S. patent application No. 60/825,459, filed Sep. 13, 2006, and is a continuation-in-part of co-pending International Patent Application No. PCT/US05/17210, filed May 16, 2005, which claims priority to U.S. application No. 60/571,831, filed May 17, 2004, and U.S. application No. 60/599,212, filed Aug. 5, 2004, and U.S. application No. 60/673,726, filed Apr. 21, 2005, the disclosures of which are incorporated by reference herein in their entirety.

The invention was made with government support under Grant No. 5 K08 01021-01 awarded by the National Institutes of Health. The U.S. government has certain rights in the invention.

BACKGROUND OF THE DISCLOSURE

T-cells act as the control center for the cellular immune response. T-cell activity can be up or down regulated resulting in the attack or ignoring of an antigen, respectively. The ability to down-regulate or become tolerant to specific antigens is crucial for the preservation of "self" antigens (the molecules that are naïve to our bodies for normal function). On the other hand, non-tolerized T-cells attack and destroy antigens that are foreign to our bodies. Examples of foreign bodies are viruses or defective proteins on the surface of cancer cells.

It is beneficial that T-cells attack foreign antigens to preserve the integrity of our bodies, however, situations can arise where attacking T-cells become a problem. For example, after an organ has been transplanted into a body from another human, or even an animal, there are numerous foreign antigens on the surface of the cells of the foreign tissue. The T-cells do not recognize the difference between a tumor and a beneficial kidney transplant. Thus, the T-cells attack the new kidney as though it is harmful to the body. Attack by the T-cells results in the destruction of the new kidney. This event is referred to as rejection of the transplant.

Rejection of a donated organ from another person or animal can be avoided by ensuring that T-cells do not attack the foreign antigens on the cell surfaces of the new tissue. Physicians accomplish this goal by using immunosuppressive drugs to turn off T-cells so they do not attack the foreign antigens of the donated organ. Thus, the foreign organ is tolerated by the body and is not rejected. Unfortunately, immunosuppressive drugs suppress the entire immune system and other foreign antigens, such as those on virally infected cells and tumor cells, go unchecked by T-cells and can multiply without interference from the T-cells. In fact, immunosuppressive drugs knock out other parts of the immune system, for example, B-cells, resulting in the body being susceptible to attack by bacterial, viral, and fungal organisms. Consequently, immunosuppressive drugs are effective in non-rejection of the organ transplant, but also result in risk of infectious organisms. This problem is addressed by keeping the organ transplant recipient in an environment as clear as possible of infectious agents, but keeping the environment completely infectious agent-free is impossible.

One of the marvels of the immune system is that it is designed to recognize each of the millions of antigens individually. When the immune system is presented with the proper antigenic information, the T-cells will attack only that specific antigen(s). Similarly, T-cells can be tolerized against specific antigens if only those antigens are presented to the immune system in the proper manner. Thus, if only the antigens of the transplant organ are presented to the T-cells for tolerance, the T-cells will leave the transplant alone and still stand guard against other infectious agents.

Central to the regulation of the immune response against any given antigen is the role of the helper T cells. These CD4+ cells interact with an antigen presenting cell (APC) expressing a specific antigenic peptide complexed with MHC Class II antigens. It is generally accepted that two signals are required for effective activation of T lymphocytes. Signal one is provided via interactions with the T cell receptor and its specific antigenic peptide complexed with the MHC protein. The second signal is referred to as the costimulatory signal and it is now believed that a major mediator of signal two is delivered via the T cell surface protein CD28. The CD28 ligands, B7.1 (CD80) and B7.2 (CD86), are primarily found on antigen presenting cells (APCs), but are also sometimes expressed on other non-lymphoid tissues. CD28 engagement also results in an increase in CTLA-4 cell surface expression. CTLA-4 is a critical T cell surface receptor and signaling via CTLA-4 results in the down modulation of the T cell response. CTLA-4 knockout mice have early lethality from a severe lymphoproliferative disorder. Crosslinking experiments with anti-CTLA-4 antibodies in the presence of TCR signaling and CD28 crosslinking show hampered T cell activity. Memory T cells were more sensitive to CTLA-4 mediated inhibition than were nayve cells. CTLA-4 engagement by anti-CTLA-4 antibody generates the antigen or target specific immunoregulatory T cells that effectively suppress unwanted antigen or tissue specific immune response. It has been suggested that T cells constitutively expressing the CD25 marker (CD4+/CD25+ T cells) are critical for ensuring peripheral tolerance against self-reactive T cells.

Dendritic cells are antigen presenting cells (DCs) belonging to a family of professional antigen presenting cells (APCs) that are present in small numbers virtually in all organs. DCs are unique in that they are highly mobile and migrate from peripheral tissues to the lymphoid organs via the blood and/or the lymphatics, a property that is not commonly associated with other APCs. A general property of all subtypes of DCs is that they pass through several stages of maturation during their life span. Immature DCs express low levels of MHC class-II and co-stimulatory molecules, but the surface expression of these molecules dramatically increases upon maturation in response to appropriate antigenic or inflammatory stimuli. A number of stimuli, provided by microbial products and inflammatory chemokines [e.g. tumor necrosis factor-α (TNF-α) and IL-1] can induce migration of DCs, and regulate changes in the expression of chemokine receptors and adhesion proteins on their surface. Immature DCs, in the periphery, are specialized for antigen capture by endocytosis or macropinocytosis, however, once matured, the DCs lose their ability to capture the antigen and become highly efficient antigen presenting cells (APCs). These APCs activate antigen specific naïve T cells in the peripheral lymphoid organs, where the antigen is trapped and both cell types co-localize. In addition to their interaction with T cell receptors (TCRs), DCs can activate T cells through several membrane-bound receptor-ligand interactions and through cytokine production. These interactions can significantly affect not only the magnitude but also the qualitative nature of the T cell response. Another remarkable property of DCs is that they maintain their ability to present antigens encountered in the peripheral tissues even after they have migrated to T cell zones in the lymphoid organs. This allows accumulation and persistence (for over 100 h) of MHC class-I/II-peptide complexes. In contrast, the intracellular sequestration of class-II peptide complexes, and a blockade of peptide loading to MHC molecules in immature DCs can delay the presentation of peptides in the context of MHC. These events are regulated by inflammatory stimuli, which facilitate migration of peptide loaded DCs into the T cell zone in lymph nodes. Stable MHC-peptide complexes expressed on the surface of mature DCs form an immunological synapse with naïve T cells resulting in optimal T cell activation.

Engagement of CTLA-4 can induce regulatory T cells and suppress autoimmune responses: CTLA-4 is a critical T cell surface receptor and signaling via CTLA-4 results in the down modulation of the T cell response. Evidence continues to accumulate that the induction of peripheral T cell tolerance in vivo requires CTLA-4 engagement. Further, recent studies have shown that the CD4$^+$CD25$^+$ Treg cells constitutively express CTLA-4 and suggest that signaling via CTLA-4 is essential for the functioning and maintenance of these cells. High affinity B7.1 interaction, but not B7.2 interaction, with CTLA-4 is important in T cell down-modulation and the Ig-constant like c-domain of B7.1 is important in this high affinity interaction. In addition, interactions between B7.1 and CTLA-4 on activated T cells results in T cells with a regulatory phenotype. The target specific tolerogenic effect of CTLA-4 engagement in an alloantigen system as well as in a murine model of Hashimoto's thyroiditis was demonstrated by the inventors. This tolerance induction by CTLA-4 engagement is mediated by CD4$^+$CD25$^+$ Treg cells and the cytokines (IL-10 and/or TGF-β1) produced by those cells.

The burden of immune-mediated diseases is staggering. In the United States, these conditions result in direct and indirect costs that exceed $100 billion. Autoimmune diseases such as rheumatoid arthritis, type I diabetes and multiple sclerosis together affect approximately 5% of the U.S. population. At least 7% of American children are asthmatic, and more than one in five individuals in the United States are affected by allergies. In addition, immune-mediated graft rejection remains a significant obstacle to the successful transplantation of potentially life-saving organs" (NIAID Publication, Jan. 23, 2001).

Effective intervention against inflammation, autoimmune disease and transplant rejection requires the ability to down regulate the immune response. Traditional clinical approaches to these conditions have relied on the administration of immunosuppressive drugs that result in a global attenuation of the immune response. As evidenced by patients suffering from AIDS, or those receiving immunosuppressive agents to prevent transplant rejection, an individual with a weakened immune response is susceptible to a wide range of opportunistic infectious agents and an increased risk for developing malignancies. These potentially fatal side effects continue to be the limiting factors of current immunosuppressive drugs.

Organ transplants from other humans, or in theory other animals, would be feasible if the T-cells that would normally attack antigens on the cells of the transplanted organ were down-regulated.

Granulocyte-macrophage-colony-stimulating-factor (GM-CSF) has the potential, not only to prevent, but also to suppress experimental autoimmune thyroiditis (EAT). GM-CSF induced EAT suppression in mice was accompanied by an increase in the frequency of CD4$^+$CD25$^+$ regulatory T cells that could suppress mouse thyroglobulin (mTg) specific T cell responses in vitro, but the underlying mechanism of this suppression was not elucidated. GM-CSF can induce DCs with a semi-mature phenotype, an important characteristic of DCs that are known to play a critical role in the induction and maintenance of regulatory T cells. Adoptive transfer of CD4$^+$CD25$^+$ T cells from GM-CSF treated and mTg primed donors into untreated, but mTg primed, recipients resulted in decreased mTg specific T cell responses. Furthermore, lymphocytes obtained from these donors and recipients after adoptive transfer produced significantly higher levels of IL-10 relative to mTg primed, untreated, control mice. Administration of anti-IL-10 receptor (αIL-10R) antibody into GM-CSF treated mice abrogated GM-CSF induced suppression of EAT as indicated by increased mTg specific T cell responses, thyroid lymphocyte infiltration, and follicular destruction. Interestingly, in vivo blockade of IL-10 receptor did not affect GM-CSF induced expansion of CD4$^+$CD25$^+$ T cells. However, IL-10 induced immunosuppression was due to its direct effects on mTg specific effector T cells. Taken together, these results indicated that IL-10, produced by CD4$^+$CD25$^+$ T cells that were likely induced by semi-mature DCs, is essential for disease suppression in GM-CSF treated mice.

Though dendritic cells (DCs) are essential for the induction of an effective immune response against foreign antigens, they can also play a critical role in promoting and maintaining tolerance to self-antigens. Modulation of DC phenotype and maturation status in vitro and in vivo can have a profound effect on T cell activation and differentiation, and skew the immune response. Different subsets of DCs can preferentially influence a Th1 or a Th2 type response. Specifically, injection of CD8a$^+$ DCs triggers the development of Th1 cells whereas CD8a$^-$ DCs induce Th2-type responses to soluble antigens. Therefore, targeted expansion of a particular DC subset might be used to shift an immune response from one type to another and thereby prevent autoimmune disease development. In addition, DC maturation can be modulated using different cytokines to induce either regulatory T cells or effector T cells.

Neither CD8a$^+$ nor CD8a$^-$ DCs can induce optimal T cell responses when they are immature, but become potent activators of T cells when they are matured. While immature DCs, characterized by expression of low levels of co-stimulatory molecules and pro-inflammatory cytokines, can promote anergy; semi-matured DCs that express significant levels of MHC class II and co-stimulatory molecules, but low levels of pro-inflammatory cytokines compared to mature DCs can induce regulatory T cells. Modulation of functional properties of DCs can be an effective therapeutic approach for autoimmune conditions.

Experimental autoimmune thyroiditis is a well established mouse model for Hashimoto's thyroiditis (HT). Hashimoto's thyroiditis is an organ-specific autoimmune disease characterized by lymphocyte infiltration of the thyroid that eventually leads to follicular destruction. In HT, thyroglobulin specific T cells are generated and they migrate to the thyroid. These cells produce IFN-γ, which induces expression of MHC class II on thyrocytes, and results in further expansion and accumulation of activated mTg specific T cells. The mechanism(s) of thyroid destruction, though not completely understood, appears to involve cytokine production by thyroid infiltrating T cells that can facilitate apoptosis of thyrocytes through caspase activation.

Administration of GM-CSF or Flt3-L, potent dendritic cell growth factors, resulted in suppression or augmentation of EAT respectively. Treatment with GM-CSF induced CD8a$^-$ DCs and caused a shift in the immune response against thyroglobulin from a Th1 response to a Th2 response, as seen by increased IL-4 production with a concomitant decrease in IFN-γ production. However, GM-CSF induced suppression of EAT was not associated with mere Th2 skewing but also with a selective expansion of $CD4^+CD25^+$ regulatory T cells that could suppress mTg specific responses in vitro. $CD4^+CD25^+$ regulatory T cells play a critical role in the suppression of autoimmunnity. Depletion or absence of $CD4^+CD25^+$ regulatory T cells has been reported to result in the development of autoimmune disease. Although how regulatory $CD4^+CD25^+$ T cells suppress autoimmunity is not fully understood, suppressor cytokines, such as IL-10, have been implicated. In GM-CSF treated mice, there was considerable increase in the levels of IL-10, and neutralization of IL-10 in lymphocyte cultures derived from GM-CSF treated mice restored mTg specific T cell responses. Furthermore, lymphocytes from GM-CSF treated mice, that were depleted of $CD4^+CD25^+$ T cells showed enhanced mTg specific proliferation with a concomitant decrease in the levels of IL-10 in vitro, suggesting that these cells were the source of IL-10.

Investigation of a direct role of $CD4^+CD25^+$ T cells and IL-10 in GM-CSF induced suppression of EAT showed that adoptive transfer of $CD4^+CD25^+$ T cells from GM-CSF treated mice into mTg primed mice can suppress mTg specific proliferation, and cells from recipient mice can produce higher levels of IL-10. Furthermore, in vivo blockade of IL-10 receptor can abrogate GM-CSF induced suppression and restore mTg specific T cell responses resulting in the development of EAT. An increase in DCs with a semi-mature phenotype in GM-CSF treated mice was observed. Since semi-matured DCs can induce regulatory T cells, data suggested a mechanism for the induction of regulatory T cells. Results support arolethat $CD4^+CD25^+$ T cells and IL-10 play in GM-CSF induced suppression of EAT.

Autoimmune myasthenia gravis (MG)2 is a T cell-dependent, Ab-mediated, organ-specific autoimmune disease. Autoantibodies targeted to the skeletal muscle acetylcholine receptor (AChR) impair neuromuscular transmission resulting in muscle weakness. Current therapies for MG produce nonspecific immune suppression, must usually be continued lifelong to maintain disease control, and are associated with significant chronic side effects and enhanced risk for infection and malignancy.

SUMMARY OF THE DISCLOSURE

Methods and compositions disclosed include a dendritic cell or cells coated with an anti-CTLA-4 antibody, wherein the antibody is also capable of binding to a specific antigen or a specific tissue.

A bispecific antibody includes a dendritic cell bound to an anti-CTLA-4 antibody that also is capable of binding to a specific antigen or tissue.

A method to induce a tissue specific tolerance includes the steps of:
(a) maturing dendritic cells with antigens of interest to activate T-cells; and
(b) contacting the activated T-cells with dendritic cells coated with an anti-CTLA-4 antibody to engage CTLA-4 on the surface of the activated T-cells.

A method to induce antigen specific tolerance includes the steps of:
(a) presenting at least one specific antigen to a dendritic cell;
(b) facilitating the dendritic cell processing and presenting the antigen;
(c) allowing the dendritic cell to stabilize cell surface molecular expression;
(d) preventing further antigen processing; and
(e) treating the antigen expressing dendritic cell with a bispecific antibody that binds to the dendritic cell surface and retains the ability to bind to the CTLA-4 molecule on the surface of a T cell or other lymphocyte.

A method to induce antigen specific T cell tolerance includes culturing bispecific antibody coated dendritic cells with T cells. The culturing may be in vitro.

A method to protect a graft from a host-graft rejection in a mammal includes the steps of:
(a) presenting an antigen responsible for a host-graft rejection to a dendritic cell;
(b) culturing a bispecific antibody coated dentritic cell with T-cells to induce antigen specific T-cell tolerance; and
(c) administering the T-cells to the host.

A method to affect maturation of dendritic cells, wherein the cells are held in semi-mature status that can induce regulatory T cells includes the steps of (a) pulsing dendritic cells; (b) coating the pulsed dendritic cells with an appropriate bi-specific antibody, wherein one arm provides target/antigen specificity and the other arm provides CTLA-4 ligation; and (c) contacting the cells with GM-CSF.

Regulatory T cells (Tregs) are either generic or antigen specific. The regulatory T cells produce TGF-beta and/or IL-10 through which Tregs can suppress immune responses.

A method of treating an autoimmune disease includes the steps of administering to a patient in need of treatment, a therapeutically effective amount of a composition comprising antigen-activated semi-mature dendritic cells, wherein the dendritic cells are produced by a method including culturing a tissue source on a substrate and in a culture medium, wherein said culture medium includes GM-CSF and at least one other factor which inhibits a proliferation or maturation of non-dendritic cell precursors, thereby increasing the proportion of dendritic cell precursors in the culture; and wherein the dendritic cells are pulsed with a self-protein, and wherein the dendritic cells process the self-protein to produce a modified self-protein antigen, which is expressed by the dendritic cells.

Diseases include Hashimoto's thyroiditis, type-1 diabetes, myasthenia gravis, atopic dermatitis and multiple sclerosis.

Methods to generate regulatory T cells includes the steps of:
1. Treating dendritic cells with GM-CSF to induce semi-matured cells either in vitro or in vivo.
2. These semi-matured dendritic cells can be pulsed with allo or self- antigen of interest.
3. They can then be coated with a bi-specific antibody with an ability to bind CTLA-4.
4. Coated cells can be used to induce regulatory T cells in vitro and/or inoculated into the host to induce regulatory T cells in vivo.
5. In vitro induced regulatory T cells can be infused into the host to prevent/suppress allo graft rejection or to treat autoimmune diseases.
6. It is also possible to directly inoculate GM-CSF and/or a bispecific antibody with an ability to bind CTLA-4, either together or sequentially, to induce regulatory T cells in vivo.

A method to affect maturation of dendritic cells, wherein the cells are held in semi-mature status that can induce regulatory T cells includes the steps of:
(a) pulsing dendritic cells;
(b) contacting the dendritic cells with GM-CSF; and (c) coating the pulsed dendritic cells with an appropriate bi-specific antibody, wherein one arm provides target or antigen specificity and the other arm provides CTLA-4 ligation.

The regulatory T cells (Tregs) can be either generic or antigen specific and the regulatory T cells produce TGF-beta and/or IL-10 through which Tregs can suppress immune responses.

A method to prevent development of T and B cell mediated autoimmune diseases includes the steps of:
(a) incubating dendritic cells with autologous tissue bearing autoantigens responsible for an autoimmune disease,
(b) maturing the dendritic cells,
(c) coating the dendritic cells with the bispecific antibody that signals antigen specific T cells to assume a regulatory type,
(d) using regulatory T cell to modulate antigen specific B cells to modulate the humoral component of an autoimmune disease.

The p value was calculated by comparing each value for the treated group with the corresponding value of the control group. *, $p \leq 0.05$.

Figure 21:
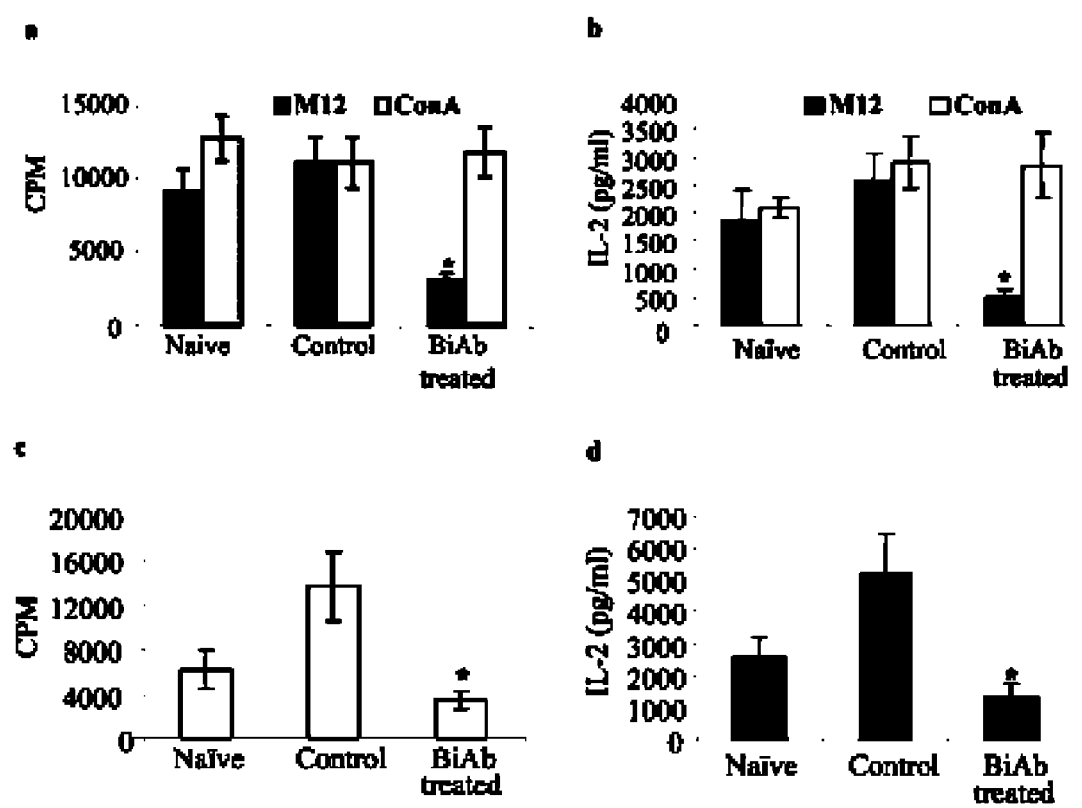

FIG. 21 shows lasting effect of tolerance induced upon CTLA-4 engagement. CBA/J ($H_2^k$) mice were immunized with BiAb-coated mM12 cells on days 0 and 10 as described in Materials and Methods. These mice were divided into two sets and sacrificed on either day 20 or 70. On day 20, spleen cells from naive mice (naive) or mice immunized with cBiAb-coated (control) or tBiAb-coated (BiAb-treated) mM12 cells were stimulated in triplicate wells ($0.5 \times 10^6$ spleen cells/well) with mitomycin C-treated M12 cells ($0.5 \times 10^5$/well) for up to 5 days. a, Lymphocytes were washed, counted, and restimulated with M12 cells or Con A (1 µg/nml) for 48 h for T cell proliferation assay by the [$^3$H]thymidine incorporation method. b, Spent media collected after 48 h were tested for IL-2 by ELISA. c and d, On day 60, the second set of mM12 immune as well as BiAb-treated mice were challenged with M12 cells, sacrificed on day 70 along with naive mice, and tested for T cell-proliferative and IL-2 responses to M12 cells. Background counts per minute (<200) and cytokine (<10 pg/ml) values in spleen cell cultures containing no M12 cells or Con A were subtracted from respective test values. Results are expressed as mean±SD of triplicate samples obtained from five individual mice. This experiment was repeated with similar results. The p value was calculated by comparing treated group values with the corresponding values for the control group. *, $p \leq 0.05$.

Figure 22:
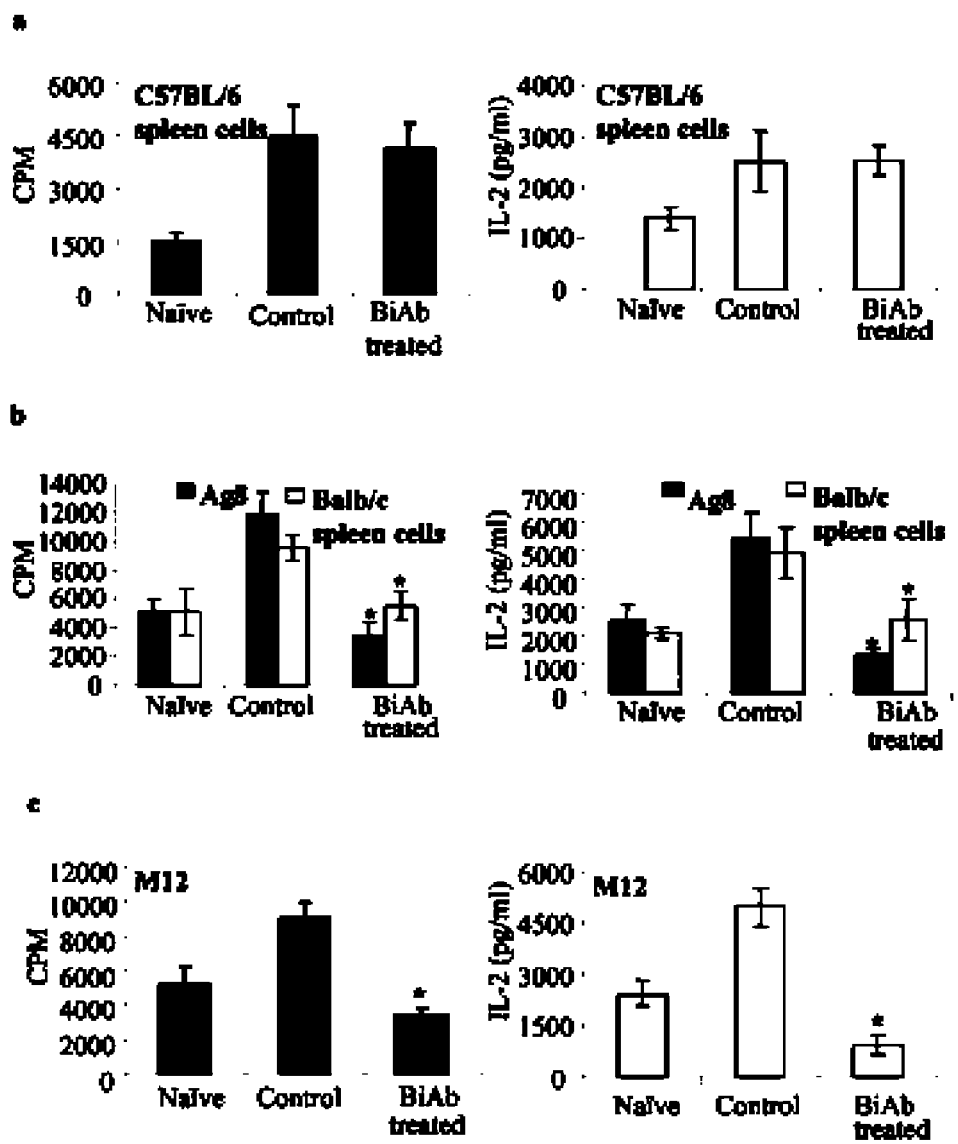

FIG. 22 shows an analysis of allotolerance specificity. CBA/J ($H_2^k$) mice were immunized with mM12 ($H_2^d$) cells in the presence of surface-bound cBiAb or tBiAb as described in Materials and Methods. Naive mice received neither mM12 cells nor BiAb. The control group received mM12 cells coated with cBiAb on days 0 and 10, and the BiAb-treated group received tBiAb-coated mM12 cells on days 0 and 10. Mice in mM12 immune and BiAb-treated groups received C57BL/6 spleen cells ($5 \times 10^6$ cells) on day 20. Spleen cells collected from all three groups on day 30 postimmunization were stimulated in triplicate wells ($0.5 \times 10^6$ cells/well) with either mitomycin C-treated spleen cells from C57BL/6 ($H_2^b$) ($1 \times 10^5$/well) (a), or BALB/c ($H_2^d$) ($1 \times 10^5$/well) mice or Ag8 B cells ($H_2^d$) ($0.5 \times 10^5$/well) (b), or M12 cells ($H_2^d$) ($0.5 \times 10^5$/well) for 48 h (c). The T cell-proliferative response (left panel) was measured by standard [$^3$H]thymidine incorporation (18-h) method. Spent media collected after 48 h from these cultures were tested for IL-2 by ELISA (right panel). Results are expressed as mean±SD of triplicate values obtained from three individual mice. This experiment was repeated with similar results. The p value was calculated by comparing values for the treated group with the corresponding values for the control group. *, p<0.05.

Figure 23:
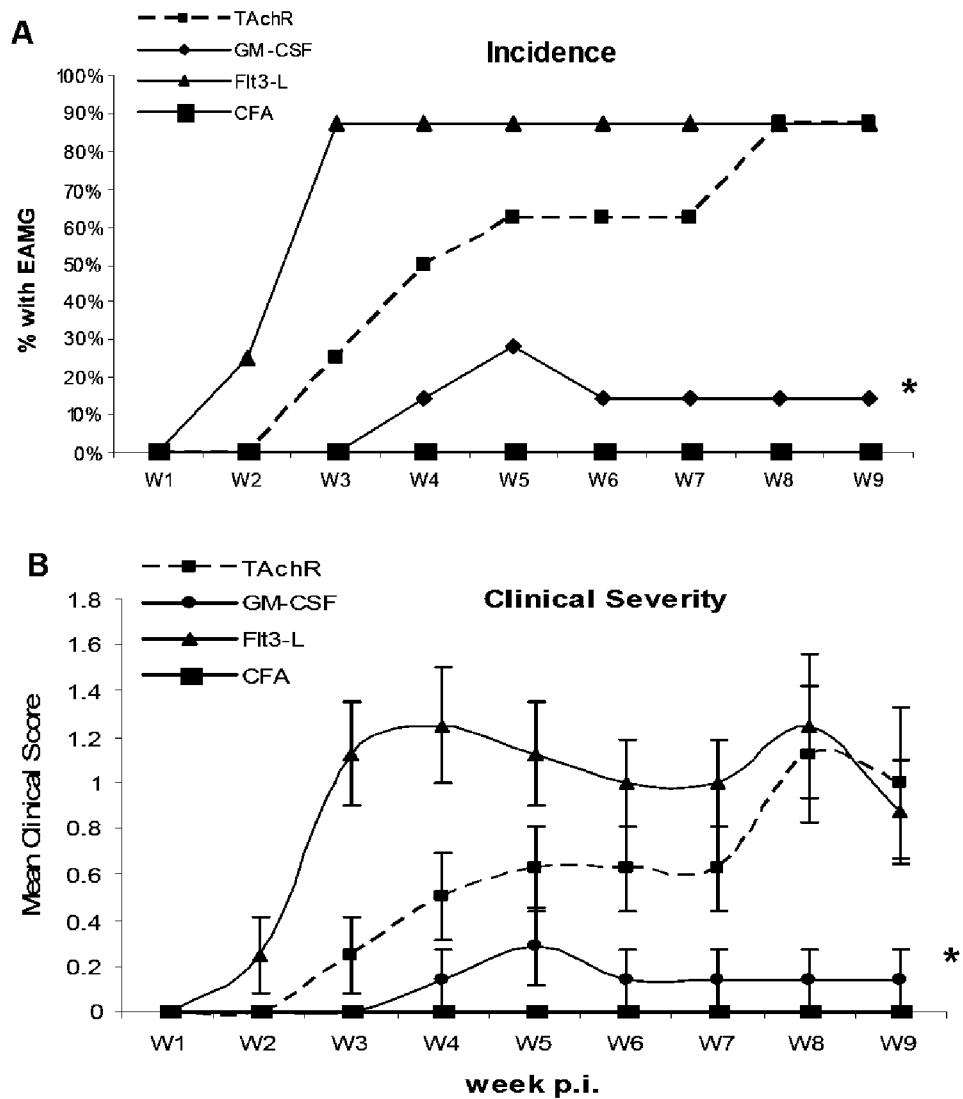

FIG. 23 shows frequency and severity of EAMG induction in GM-CSFtreated, Flt3-L-treated, untreated tAChR-immunized mice, and negative control (CFA) mice. Mice were evaluated as described in Materials and Methods on an every other day basis beginning after the first immunization. A, The percentage of animals demonstrating myasthenic weakness (incidence) in each experimental group is shown, with values given for each of the nine weeks of the observation period (W1-W9 on the x-axis). B, The average clinical score during weeks 1-9 of the observation period is shown for each of the four groups. Both incidence and disease severity were significantly lower in GM-CSF-treated mice compared with the untreated tAChR-immunized controls (*, p<0.01). FIG. 23A shows the incidence of EAMG over the 9-wk observation period; FIG. 23B shows the average clinical scores over the same period (tAChR=8, Flt3-L=8, GM-CSF=8, CFA=6). Disease incidence at the end of the observation period in GM-CSF-treated mice compared with tAChR-immunized controls showed a significant difference (p<0.01), as did average disease severity (p<0.01).

Figure 24:
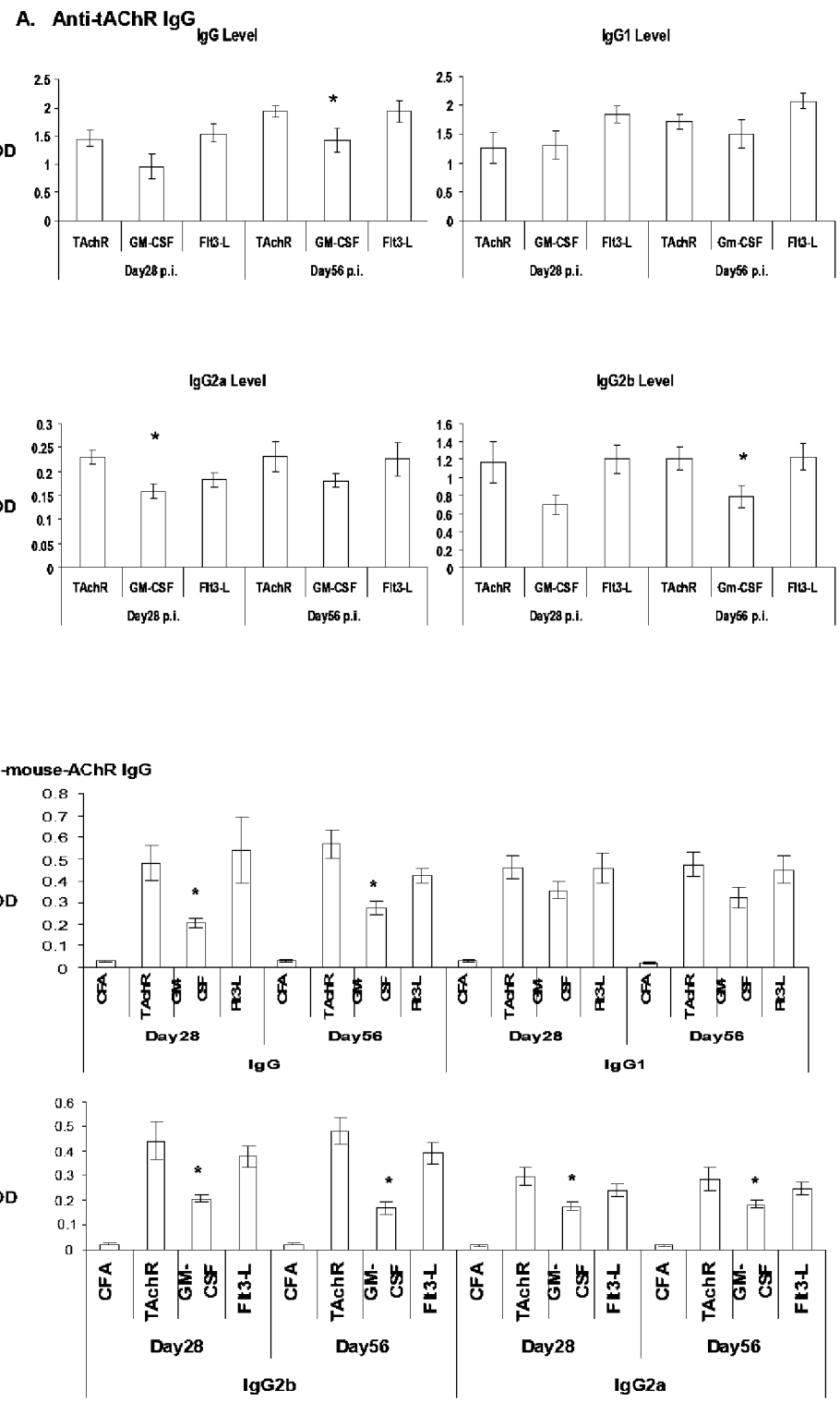

FIG. 24 shows serum anti-tAChR (A) and anti-mouse AChR (B) IgG and IgG subclasses for GM-CSF-treated, Flt3L-treated, and control mice. Anti-tAChR and anti-mouse AChR IgG Ab and IgG isotypes were analyzed by ELISA (n=8/group) on day 0, day 28 and day 56, with day 0 corresponding to the day of initial tAChR immunization. A, GM-CSF-treated mice showed significantly lower serum levels of anti-tAChR IgG, IgG2a, and IgG2b at day 28, and lower levels of anti-tAChR IgG and IgG2b at day 56. B, GM-CSF-treated mice also showed significantly lower level of anti-mouse AChR IgG, IgG2a, and IgG2b at days 28 and 56. Each column represents the mean±SE of three individual experiments conducted in triplicate (*, p<0.05).

Figure 25:
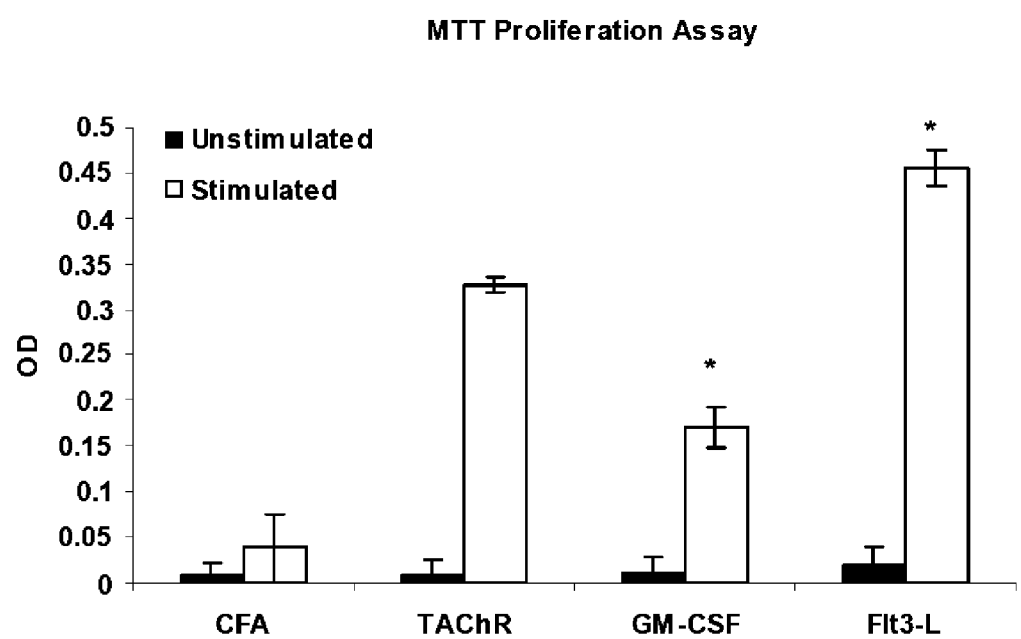

FIG. 25 shows effects of GM-CSF and Flt3-L on T cell-proliferative response to tAChR. Mice were treated with GM-CSF, Flt3-L, or PBS as described in Materials and Methods before immunization with tAChR on day 0. The negative control group (CFA) also received PBS. Mice were sacrificed on day 14 to obtain spleen cells, and the proliferative response to tAChR was assayed by MTT method. Spleen cells from mice treated with Flt3-L showed a significantly higher proliferative response to stimulation with tAChR, whereas GM-CSF-treated mice showed a significantly lower proliferative response. No differences were observed in the GM-CSFtreated, Flt3-L-treated, and untreated mice with nonspecific stimulation using the lectin Con A. All the results are expressed as mean values±SE (*, p<0.05).

Figure 26:
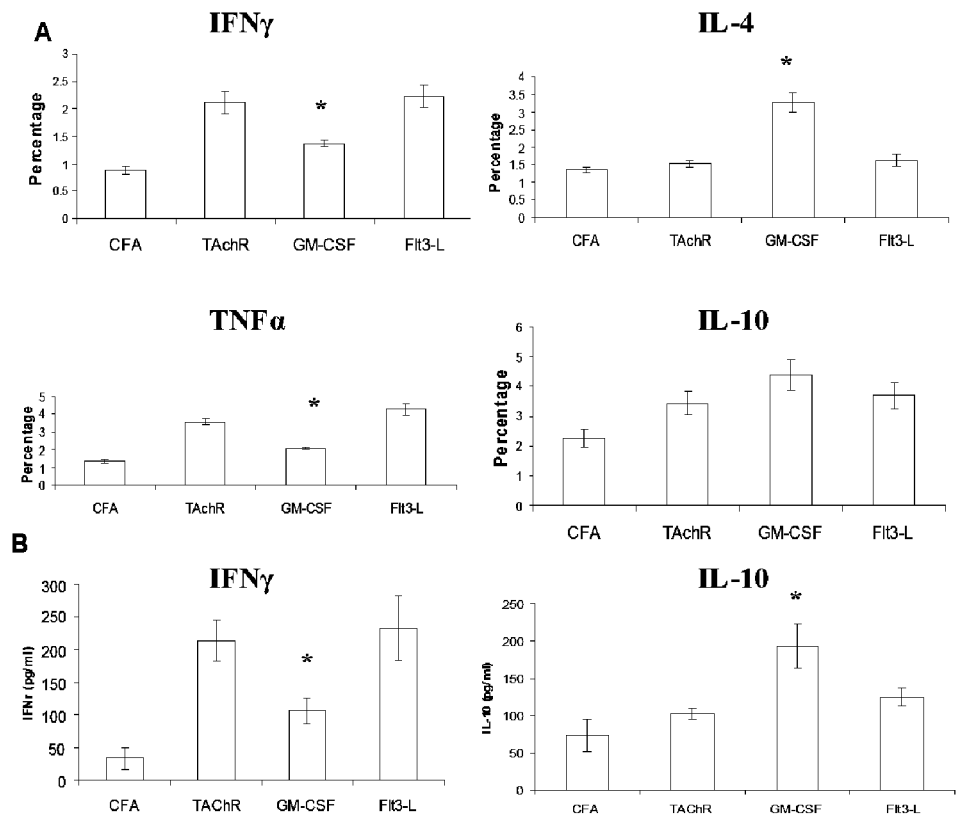

FIG. 26 shows cytokine response to tAChR stimulation. Mice were treated with GM-CSF or Flt3-L before immunization and sacrificed 14 days later. Cytokine response was measured using single-cell suspensions of splenocytes by intracellular cytokine staining (A) and/or by a multiplex suspension assay system (B). A, Intracellular staining for cytokine expression was conducted using FITC-labeled anti-CD4 and PE-labeled anti-IFN-y, PE-labeled anti-IL-4, PE-labeled anti-IL-10, or PE-labeled anti-TNF-a Abs followed by analysis by FACS. The percentages shown represent cytokine expression by isolated CD4+ cells. With GM-CSF treatment, significantly lower expression of IFN-y and TNF-a was observed, while higher levels of expression of IL-4 and IL-10 were found. B, The above splenocytes were also cultured for 48 h, and cell-free culture supernatants were assayed using a multiplex bead immunoassay for IFN-y and IL-10. Significantly lower levels of IFN-y and significantly higher levels of IL-10 were detected in GM-CSF-treated animals. A and B, Results are expressed as mean±SE (*, p<0.05).

Figure 27:
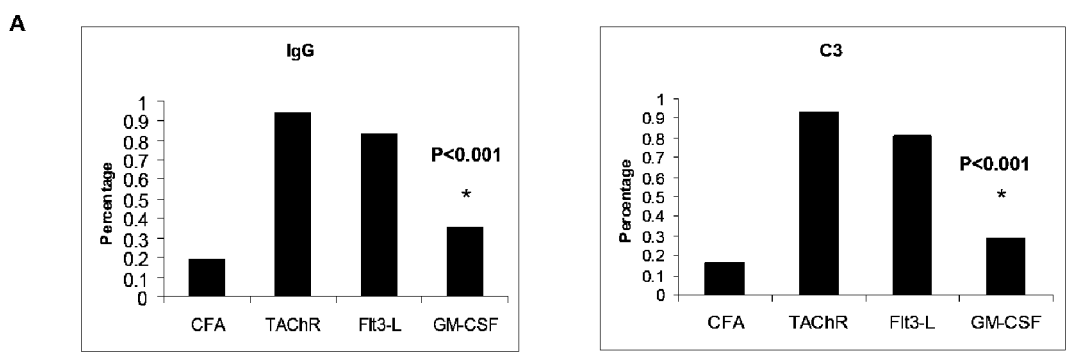

FIG. 27 shows effects of GM-CSF and Flt3-L on deposition of C3 and IgG at the NMJs of EAMG mice. Forelimb muscle specimens obtained from three mice from each of the four experimental groups were analyzed by standard immunohistochemical analysis. Cryosections of muscles were double-stained with tetramethylrhodamine-conjugated anti-BTx (second column) and goat anti-mouse IgG or goat anti-mouse C3 (first column); merge on the right. A, The percentages of visualized endplates showing immunoreactivity for C3 in each experimental group is shown in graphic form.

Figure 28:
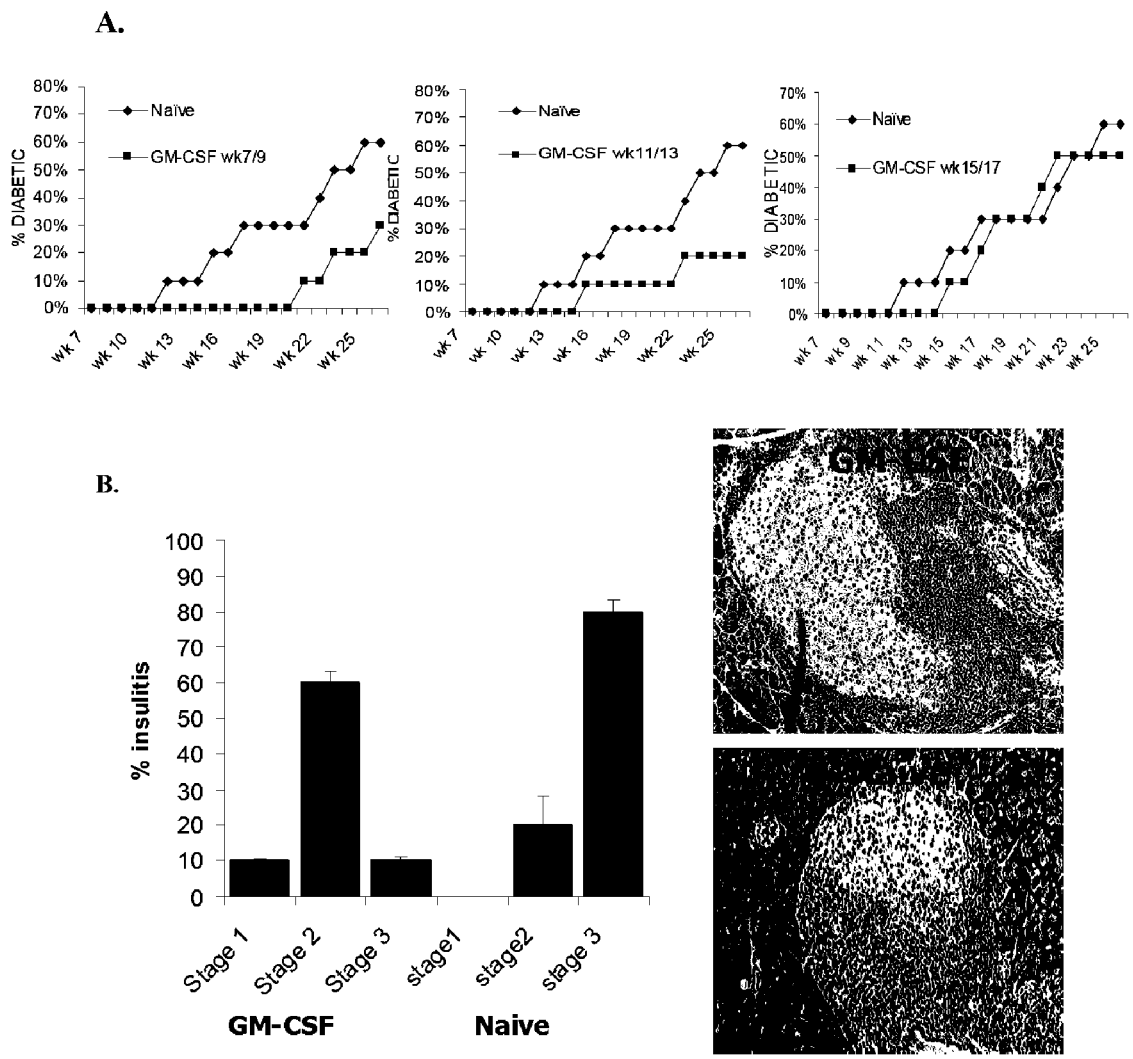

FIG. 28 shows diabetes prevalence in GM-CSF treated NOD mice. A.Groups of 10 NOD mice were treated twice with GM-CSF (2 □g/mouse) for five consecutive days at 7 and 9 wks (A), 11 and 13 wks (B), or 15 and 17 wks (C) of age IP, and blood glucose levels monitored weekly. Mice were diabetic when glucose levels remained above 250 mg/dL for 2 consecutive weeks. Experiment was terminated when >70% of untreated NOD mice became diabetic. B. Hematoxylin and eosin stained pancreatic sections and insulitis scored at 18 wks of age as described in methods. ±SD of islet counts from 5 organs per group.

Figure 29:
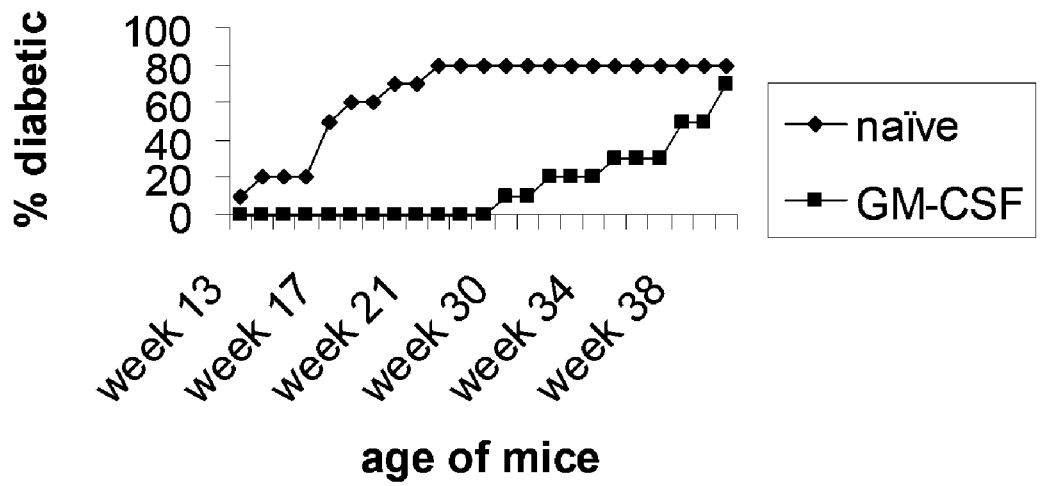

FIG. 29 shows therapeutic potential of GM-CSF. Groups of 10 NOD mice were treated with 2 μg/mL/mouse of GM-CSF on 5 consecutive days at 7, 9, 11, 13, 15 and 19 weeks of age and monitored for hyperglycemia. Mice were diabetic when glucose levels remained ≧250 mg/dL for 2 weeks. Experiment was terminated when 80% untreated mice developed hyperglycemia.

Figure 30:
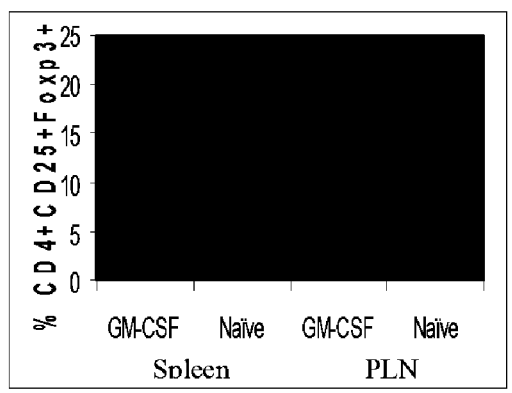

FIG. 30 shows that GM-CSF leads to an increase in Foxp3 expression. 8 week old GM-CSF treated and untreated mice were sacrificed and splenocytes and pancreatic lymph node (PLN) were subjected to intracellular staining for CD4CD25Foxp3. Representation of the average (n=3/group) CD4+CD25+Foxp3+ cells in each group are shown. Bars represent the mean±SD of foxp3+ T cells it at least 3 mice per group. Plots generated represent cells gated on CD4 and then analyzed for CD25 and Foxp3.

Figure 31:
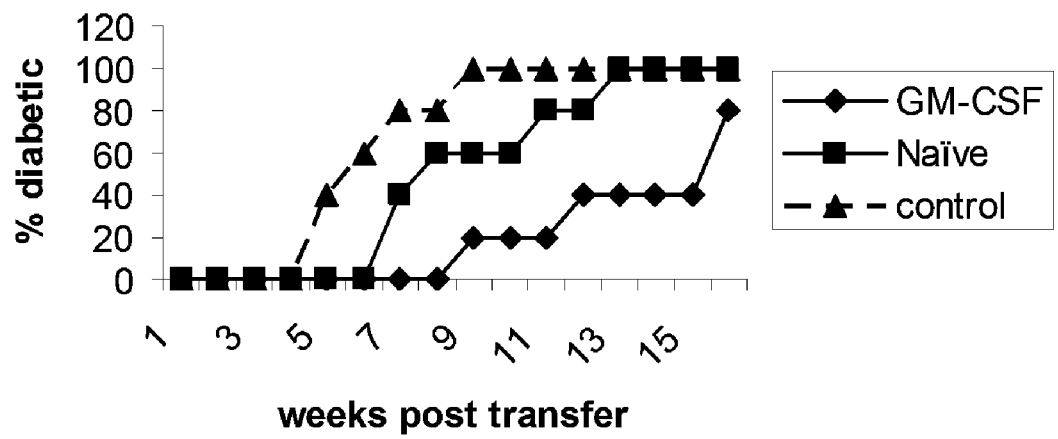

FIG. 31 shows that adoptive Transfer of CD4+CD25+ T cells from GM-CSF treated mice delays disease onset. Splenocytes from 16-20 wk old diabetic mice were transferred intravenously into 6 wk old NOD scid mice (n=5) either alone or with CD4+CD25+ T cells ($1 \times 10^6$) from 14 wk old GM-CSF treated or untreated non-diabetic female NOD mice. Diabetes incidence was monitored by measuring blood glucose levels weekly. Diabetes was determined when blood glucose rose above 250 mg/dL for 2 consecutive weeks.

Figure 32:
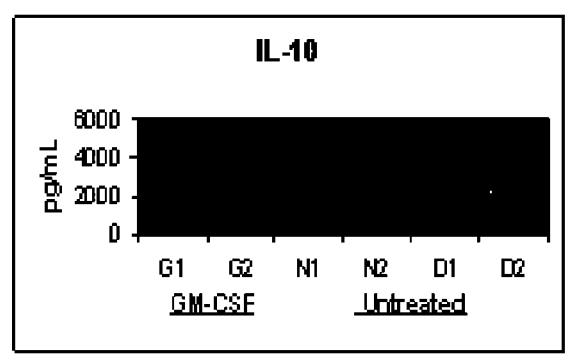

FIG. 32 shows that GM-CSF treatment results in increased IL-10 production. Splenocytes from 17-week old femal NOD mice GM-CSF treated, healthy naïve or diabetic groups were isolated and either cultures for 36 hours or cell free supernatant and tested for Il-10 production.

Figure 33:
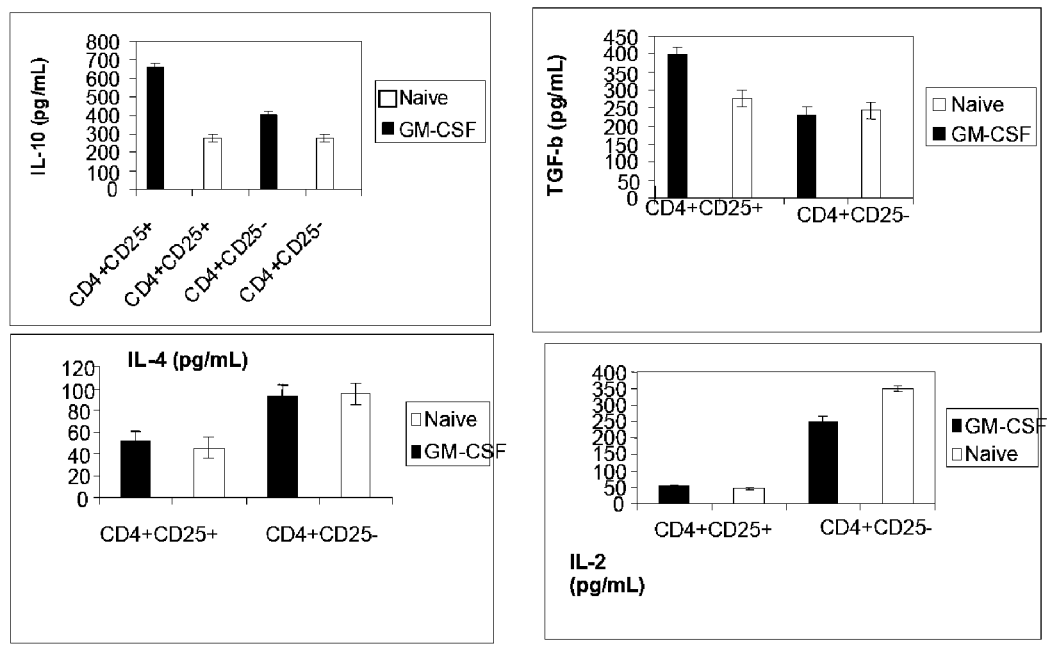

FIG. 33 shows that GM-CSF expands IL-10 and TGF-β producing Tregs. CD4+CD25+ and CD4+CD25− cells were isolated from 12 wk old naïve and GM-CSF treated female NOD mice (n=4). Cells were pooled and cultured ($2.5 \times 10^6$/well) for 48 hrs in the presence of αCD3/αCD28 (5 μg/mL) or without as a control. Cell free supernatants were harvested and analyzed for cytokine production by ELISA. The bars represent the mean±SD of triplicates.

Figure 34:
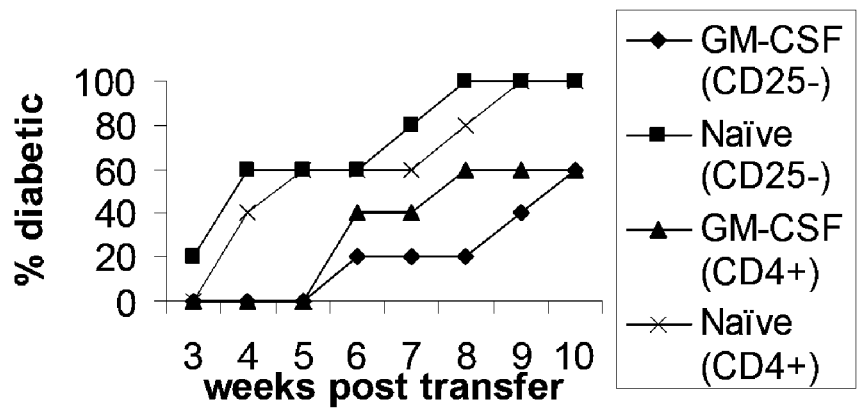

FIG. 34 shows that GM-CSF pretreatment of NOD scid mice delays disease onset in T cell adoptive transfer. Female NOD scid mice 6 weeks of age (n=5/group) were either treated with GM-CSF (10 days) or left untreated (naïve) followed by adoptive transfer of either CD4+CD25− (3×106) or whole CD4+ T cells (2×106) from 8 wk old mice. Glucose levels were monitored weekly for diabetes incidence. Mice were considered diabetic after two consecutive weeks of glucose >250mg/dL.

Figure 35:
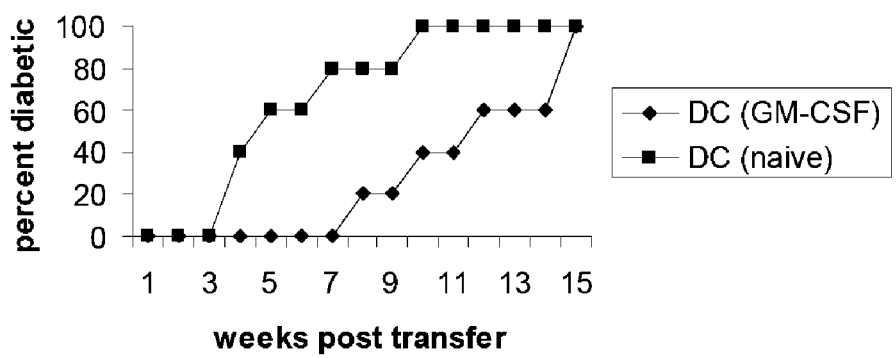
Figure 35:
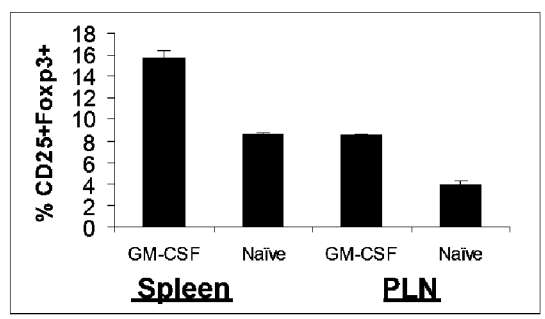

FIG. 35 shows that adoptive transfer of DCs from GM-CSF mice delays diabetes and expands Foxp3+ Tregs. a. DCs (2×106) from 10 week old female NOD mice which had been given a 2 week course of GM-CSF or age matched untreated mice were isolated and transferred intravenously to 7 week old NOD mice (n=5/group). Glucose levels were monitored weekly for diabetes incidence post transfer as previously described. b. 2 weeks post transfer mice (n=3/group) were sacrificed and analyzed for CD4+CD25+Foxp3+ expression in both spleen and pancreatic lymph node (PLN). Percentages represent average of CD4+CD25+Foxp3+ cells per group and bars represent the mean±SD of 3 mice per group.

DETAILED DESCRIPTION

Figure 1:
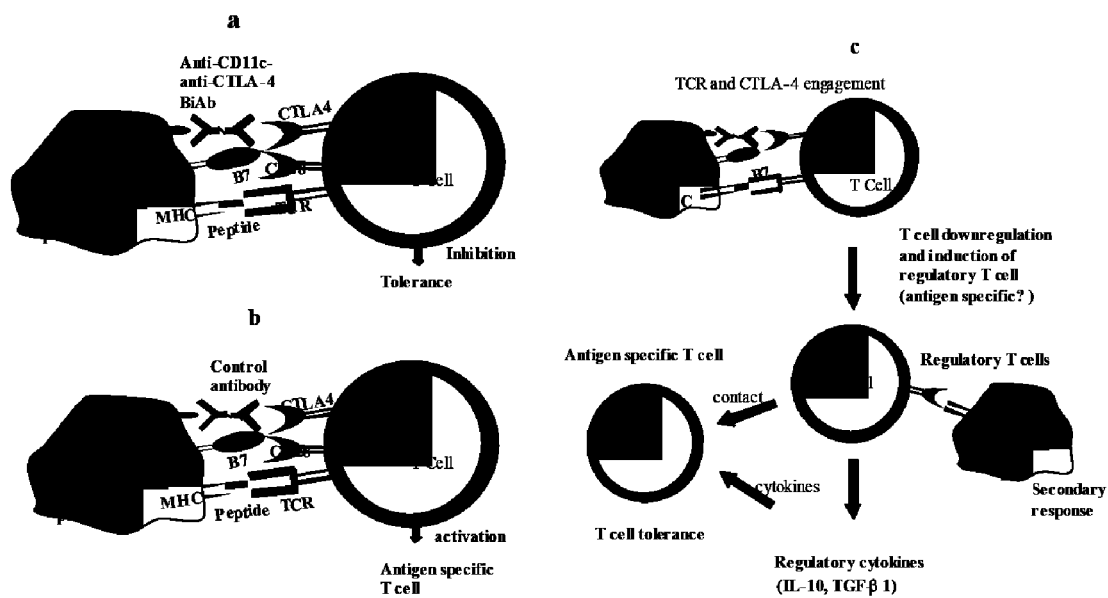
FIG. 1 shows bispecific antibody (BiAb) mediated tolerance induction; (a) activated T cells upon interaction with BiAb are turned down by CTLA-4 engagement by anti-CTLA-4 antibody; whereas (b) an antibody that does not interact with CTLA-4 (isotype control antibody) does not down regulate the T cell response to the antigen; and (c) tandem TCR and CTLA-4 engagements, presumably trigger a direct or indirect expansion of regulatory T cells with antigen specificity, which in turn down-regulates the antigen specific response of activated T cells and induces tolerance.

Transplantation involves suppressing all T-cells so that the foreign antigens of the transplant are not attacked by the T-cells, i.e. so the body does not reject the transplanted organ. The disadvantage of this approach is that the whole immune system is suppressed and the foreign antigens of infectious agents or cancerous tumors are not recognized. The body is helpless to protect itself. The disclosed method results in the suppression of only the part of the immune response that would reject the transplanted organ, thus allowing the immune system to protect the body against harmful foreign agents (FIG. 1).

A method is disclosed for presenting desired antigens such as antigens of a transplanted organ to T-cells so that they ignore those antigens. The method uses a linking molecule to bring antigen presenting cells and T-cells in close proximity for down-regulation of the T-cell via the CTLA-4 surface molecule. Presentation of the antigen(s) to the antigen-presenting cell is performed in vitro, as is the coating of the antigen-presenting cell with the bi-specific antibody complex. The antigen-presenting cells are then applied in-vivo such that the free binding site of the bi-specific antibody complex find the T-cells to be tolerized.

No systemic immunosuppressive is required not only for organ transplants, but also for any situation where the body is attacking "good" cells in the body. For example, autoimmune diseases all have in common T-cells attacking "self" antigens for an unknown reason. Autoimmune diseases are numerous, and include rheumatoid arthritis, type I diabetes, multiple sclerosis, systemic sclerosis, lupus, Hashimoto's thyroiditis, myasthenia gravis, and others.

Methods and compositions disclosed here involve the targeted removal or inactivation of those lymphocytes specifically involved in a given undesired immune response while leaving the remainder of the immune system intact. This specific removal involves inactivating only those lymphocytes that have a given antigen or tissue specificity, so that opportunistic infections, malignancies or other side effects can be avoided.

A strategy to engage CTLA-4 on T cells in an antigen specific manner combines the strong inhibitory signaling property of CTLA-4 and the exceptional antigen presentation property of dendritic cells (DCs). DC bound anti-CTLA-4 antibody engages CTLA-4 on the surface of activated T cells upon the TCR engagement of MHC-antigenic peptide on DCs. This suppresses T cell activation, which, in turn, leads to Treg cell induction, specific to an antigen of interest.

Antigen specific tolerance induction through CTLA-4 engagement uses a bispecific antibody. CTLA-4 is an exemplary T-cell receptor that is engaged by a b-specific antibody. Any receptor or ligand or a target on T-cell or any other immune cell that can be engaged by an antibody or otherwise to suppress T-cell activation or other immune cell activation, is suitable to practice the concept embodied in the disclosure.

In one aspect, tolerance is induced in an antigen specific manner by signaling through CTLA-4 on T cells by dendritic cell bound anti-CTLA-4. Anti-CTLA-4 antibody is known to cross-link and induce a CTLA-4 signal that results in T cell tolerance. This signaling ability of anti-CTLA-4 antibody is manipulated in an antigen specific manner. For this purpose, anti-CTLA-4 antibody is linked to a dendritic cell specific antibody, dendritic cells were coated with specific antigen/antigens pulsed dendritic cells so that upon in vivo or in vitro delivery, the anti-CTLA-4 portion of the BiAb will bind to the CTLA-4 on T cells and turns down T-cells.

The disclosed methods and compositions are useful because they effect: 1. Induction of tolerance to autoimmune target antigens to prevent/treat various autoimmune conditions; 2. Induction of tolerance to allo- or xeno- antigens to prevent rejection of transplanted tissue like, pancreatic islets, kidney, hearth, liver, intestine, skin, and so forth; 3. Induction of tolerance to allergens; 4. Induction of tolerance to the product of transgenes and their carrier vectors in gene therapy applications; 5. Treatment of graft versus host disease; 6. Induction of tolerance to inflammatory conditions such as inflammatory bowel disease; 7. Induction of tolerance to bacterial or viral pathogens that act as inducers of autoimmune disease or inflammatory immune mediated diseases through molecular mimicry.

The development of a clinically useful therapy for the induction of selective tissue-specific (or antigen-specific) immunomodulation generally meets the following criteria: 1. Specifically inactivates T cells involved in the undesired immune response; 2. Has little or no effect on the immune response to all other antigens and therefore minimizes the risk of opportunistic infections or compromised immune surveillance; 3. Involves agents that are biologically degradable without toxic side effects; 4. Has flexibility to direct the immunosuppression against different antigens expressed on different tissue types in various disease states; 5. Has the ability to attach different inhibitory signals to the targeting antibody for combination immunomodulation therapy.

This approach to an antigen-specific immunoregulation therapy has the flexibility to intervene against a variety of tissues and antigens and, unlike gene therapy, its dosage can be easily titrated to attain the desired effect or quickly terminated in the event of adverse side effects. This minimizes concerns about the long-term inhibition of immune surveillance and delayed presentations of malignancies.

Variations include: 1. Antibodies that can bind to any dendritic cell surface molecule, organ or tissue and are chemically linked to anti-CTLA-4 antibody. This bispecific antibody is coated onto dendritic cells or target tissue before transplantation or during an autoimmune process; 2. Genetically engineered antibodies are generated with specificity towards both the tissue of interest as well as the CTLA-4. This genetically engineered antibody is at least as effective as a chemically cross-linked antibody, 3. Dendritic cell tissue or target tissue is passively or actively (with chemical modifications) coated with anti-CTLA-4 antibody; 4. The peptide presented via the MHC can be produced via chemical, genetically engineered, or any equivalent means.

The signaling ability of anti-CTLA-4 antibody is manipulated in a tissue specific manner. For this purpose, anti-CTLA-4 antibody is linked to a tissue specific antibody, so that upon in vivo or in vitro delivery, antibodies bind to the tissue of interest and turn down tissue attacking T cells or T cells that are specific to the target tissue. For example, pancreatic islet cells are protected from autoimmune as well as allo- or xeno-immune response by coating the islets with a a bispecific antibody generated by linking an anti-Islet cell specific antibody (examples: Glut-2 or MHC class I antibody) to anti-CTLA-4 antibody. Any antibody specific to a tissue of interest can be linked to anti-CTLA-4 and used to protect the specific tissue.

GM-CSF can be modified to prolong and enhance its effects on the immune system, and prevent any undesired effect.

Semi-matured dendritic cells can be further modified or treated to enhance their efficiency of T reg induction.

EXAMPLE 1

Induction of Immune Tolerance and Regulatory T Cells Using Anti-CTLA-4 Antibody Coated DCs A novel approach to overcome the limitation (the requirement for tissue specific antibodies) of a tissue targeted CTLA-4 engagement strategy and to induce a robust Treg cell response in an antigen specific fashion uses anti-CTLA-4 antibody Tolerance induction by DC coated with anti-CD11c-anti-CTLA-4 Biab were analyzed. Mice were immunized with ovalbumin (ova) or thyroglobulin (Tg) on day 0. These mice were administered (i.v.) with respective antigen (ova or Tg) pulsed DC coated with isotype control BiAb (ova+DC or Tg+DC) or anti-CD11 c-anti-CTLA-4 BiAb (ova+DC+biAB or Tg+DC+BiAb) on day 8. Spleen cells were collected from these mice on day 20 and were tested for their T Cell proliferative IL-2, IL-10 and TGFbeta 1 responses. Resting cells collected from these mice were stained with FITC conjugated mouse CD4 antibody and PE-labeled anti mouse CD25 antibody. CD4+ cell population was gated.

Antigen pulsed DC are coated with a cross-linking anti-CTLA-4 antibody after coupling it to an anti-CD11c antibody. These cells were pulsed with either ovalbumin (ova) or Thyroglobulin (Tg) and injected intravenously into mice that had been primed with these antigens 10 days earlier. Mice injected with anti-CTLA-4 antibody coated DC showed significantly suppressed T cell proliferation and IL-2 production but increased IL-10 and TGF-betal response upon ex vivo restimulation with the same antigen compared to mice that received DC coated with isotype control antibody. These mice showed a significant increase in the $CD4^+CD25^+$ Treg cell population.

When the mice (test group) were immunized twice with ova and treated twice with anti-CTLA-4 coated ova pulsed DCs and rested for 15 days, the memory CD4+ T cell numbers were lower compared to the mice that received isotype control antibody coated DCs (control group). Although, the memory CD4+ T cell numbers were lower, these mice showed about 70% more $CD4^+CD25^+$ cells.

Induction of Treg cells to ova by ova pulsed DCs coated with Anti-CTLA-4 antibody was studied. Mice were immunized with ova+LPS on days 0 and 10 treated (i.v.) with ova pulsed control or anti-CTLA-4 antibody coated DCs ($2\times10^6$ cell/mouse) on days 20 and 30, rested for 15 days. These mice were sacrificed on day 45, tested for memory CD4+ T cells ($CD4+CD62L^{low}$), regulatory CD4+ T cells (CD4+CD25+), memory regulatory T cells ($CD4+CD25+CD62L^{high}$) T cells. Analysis was gated for CD4+ cells, or $CD4+CD62L^{low}$ cells or $CD4+CD62L^{high}$ cells.

Figure 16:
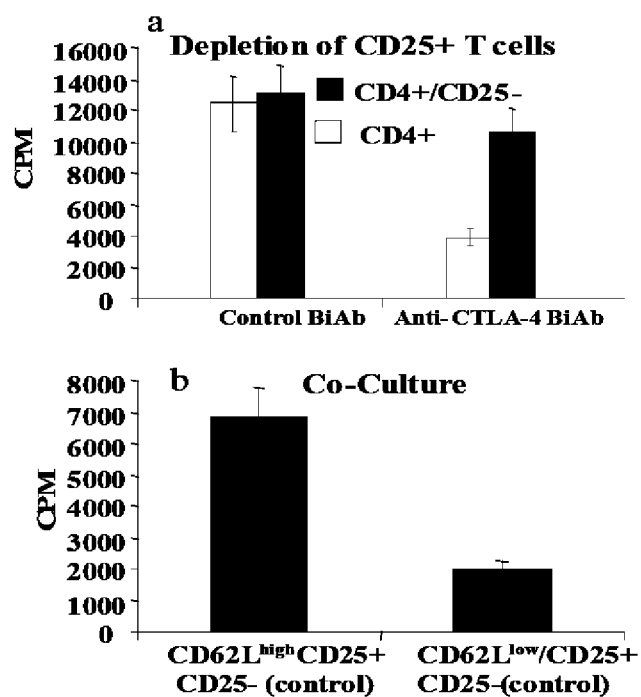
FIG. 16 illustrates immunosuppressive property of Treg cells to ova generated by ova pulsed DCs coated with anti-CTLA-4 antibody; mice were treated as disclosed (a); CD4$^+$ T cells were isolated from mice that received control antibody or anti-CTLA-4 antibody coated DCs, depleted of CD25$^+$ cells cultured in the presence of ova and APC; (b) naïve Treg cells (CD4+ CD25$^+$CD62L$^{low}$) isolated from mice that received anti-CTLA-4 antibody coated DCs were co-cultured with (CD4$^+$CD25$^-$) T cells from control mice at 1:10 ratio; a T cell proliferation assay were carried out using 3H-thymidine incorporation assay.

While the naïve $CD25^+$ T cell ($CD4^+CD25^+CD62L^{high}$) numbers were more or less the same in test and control groups, memory Treg cell ($CD4^+CD25^+CD62L^{low}$) numbers were about 150% more in test mice compared to control mice. These Treg cells could suppress antigen specific T cell response more significantly compared to $CD4^+CD25^+$ Treg cells with naïve phenotype (FIG. 16). This suggests that a large number of the memory cells generated in the test group have the Treg cells' phenotype and they are important in maintaining tolerance.

Figure 17:
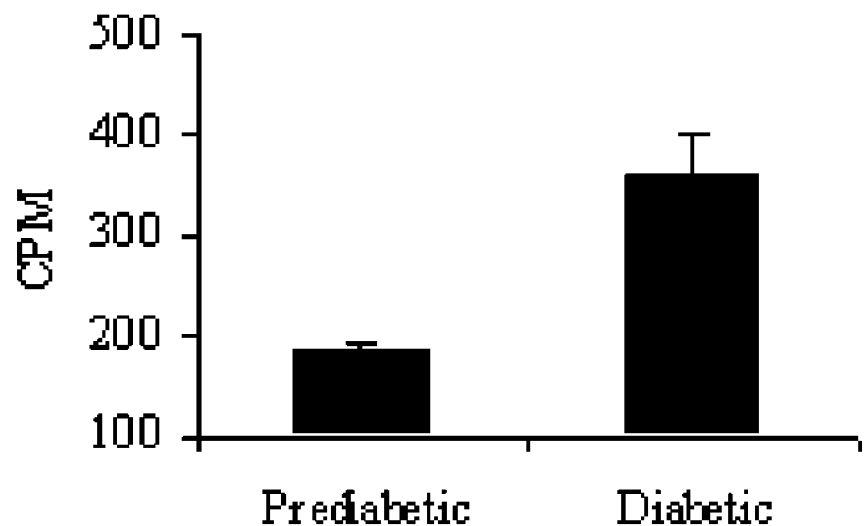
FIG. 17 shows GAD65 peptide specific T cells in NOD mice; spleen cells were collected from prediabetic and diabetic mice and incubated with pooled GAD65 peptides (GAD206-226, GAD217-236 and GAD286-300) and tested for T cell proliferative response; a T cell proliferation assay was carried out using standard 3H-thymidine incorporation assay.
Figure 18:
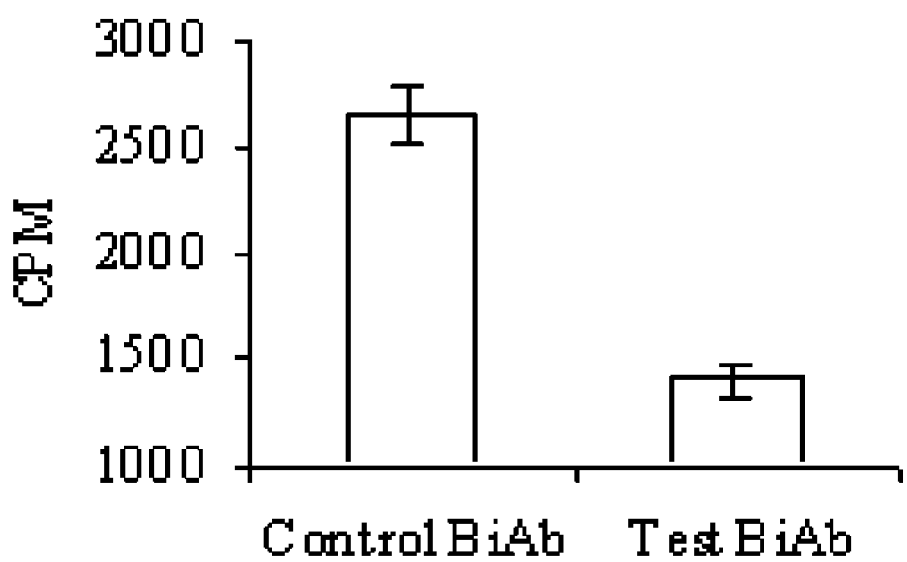
FIG. 18 shows in vitro suppression of GAD65 peptide specific T cell response upon DC directed CTLA-4 engagement; DCs isolated from prediabetic NOD mice were pulsed with pooled GAD65 peptides (GAD206-226, GAD17-236 and GAD286-300), coated with isotype control antibody (control BiAb) or anti-CTLA-4 antibody (Test BiAb) and incubated with T cells from diabetic NOD mice; a T cell proliferation assay was carried out using standard 3H-thymidine incorporation assay.

More than 60% of NOD mice developed spontaneous diabetes (glucose level, >250 g/dl) within 20 weeks of age. Recently, the anti-CTLA-4 coated DC approach was tested in NOD mice in vitro. A pool of three GAD-65 peptides (GAD206-226, GAD217-236 and GAD286-300), that are the primary and earliest targets for autoreactive T cells in NOD mice, were used as the antigen in an in vitro experiment using T cells collected from diabetic mice. As shown in FIG. 17, though the numbers were small, autoreactive T cells to these peptides were present in diabetic mice. DCs collected from pre-diabetic mice (treated ex vivo with LPS and TNF-α) were pulsed with these peptides and coated with anti-CTLA-4 antibody (using the BiAb approach) and tested against CD3+ T cells from diabetic mice. As shown in FIG. 18, anti-CTLA-4 antibody coated DCs suppressed the T cell response significantly compared to control antibody coated DCs. These results indicate that engagement of CTLA-4 at the immunological synapse by DC bound anti-CTLA-4 antibody delivers a negative signal and induces the differentiation of Treg cells even in NOD mice.

The above observations show that Treg cells can be generated by different means. The phenotypes (and the inhibitory nature) of Treg cells generated under different conditions differently may also be diverse. For example, as described above CD4+CD25+ Treg cell populations with three different cytokine induction patterns (TGF-β1 alone, TGF-β1, IL-4 and IL10 or IL-10 alone) have been observed in three different studies. This indicates that although CD4+CD25+ Treg cells include single population, functionally and/or phenotypically different sub-populations may exist. For example, anti-CTLA-4 antibody coated ova or Tg pulsed DC induced a robust CD4+CD25+ Treg cell response with memory phenotype.

EXAMPLE 2

Figure 2:
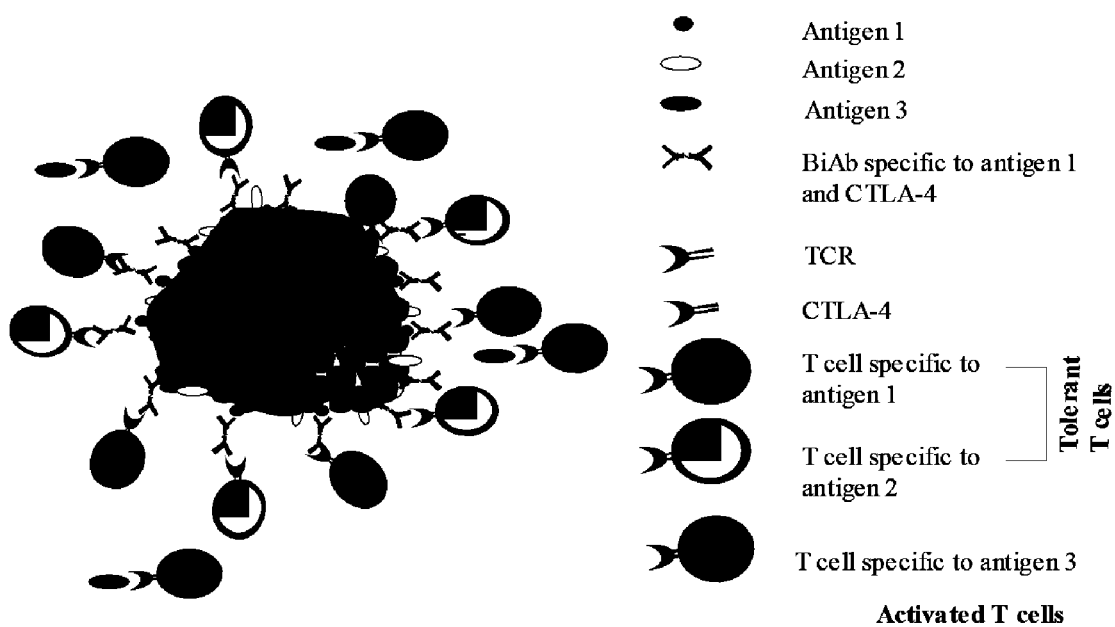
FIG. 2 shows bispecific antibody mediated tolerance induction is tissue specific;
upon targeting anti-CTLA-4 antibody to a tissue of interest using a tissue specific antibody, the antibody protects the tissue by turning down T cells specific to any antigen present in that tissue irrespective of to which antigen the BiAb is bound, however, an immune response to an unrelated antigen is not affected by this tissue targeted CTLA-4 engagement, unless those T cells specific for unrelated antigen are present in the tissue in which BiAbs are present.

Tissue Specific Tolerance Induction Through CTLA-4 Engagement Using a Bispecific Antibody (FIG. 2)

The therapeutic potential of CTLA-4 engagement using a bispecific antibody to induce tissue-specific tolerance was investigated by using an anti-CTLA-4 antibody that was coupled to an antibody specific for the thyrotropin receptor. After in vivo administration, this bispecific antibody (BiAb) accumulated in the thyroid and prevented development of experimental autoimmune thyroiditis (EAT) in mice immunized with mouse thyroglobulin (mTg). Lymphocytes from BiAb-treated mice showed a significant reduction in their ability to proliferate, and to produce IL-2, IFN-γ and tumor necrosis factor (TNF)-α, in response to mTg re-stimulation compared to lymphocytes from untreated mice. Moreover, BiAb-treated mice showed suppressed anti-mTg antibody response, lymphocytic infiltration of the thyroid and follicular destruction. The BiAb targeted to the thyroid most likely facilitated engagement of CTLA-4, resulting in an increase in the number of CD4+CD25+ T cells. These regulatory T cells suppressed in vitro mTg-specific T cell responses, which were associated with an enhanced transforming growth factor (TGF)-β1 production. Neutralization of TGF-β1 increased mTg-specific in vitro proliferation of, and IL-2 production by, T cells from BiAb -treated mice. Engagement of CTLA-4 expressed on activated autoreactive T cells in close proximity to the thyroid increases the number of regulatory T cells and their ability to produce TGF-β1, with a concomitant reduction in IFN-γ and TNF-α, resulting in suppression of EAT.

Figure 8:
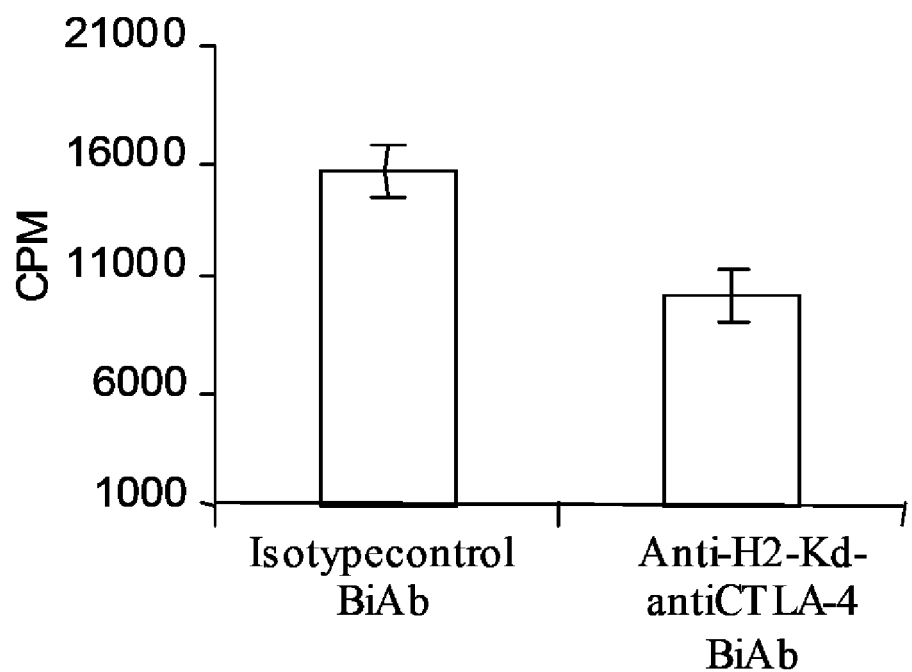
FIG. 8 shows in vitro inhibition of alloresponse to islets from Balb/c mice and used as single cell suspension prepared by trypsin digestion; islet cells were coated with either isotype control BiAb or anti-H2-Kd-anti-CTLA-4 BiAb and incubated with spleen cells from mice that were pre-immunized with H2Kd alloantigen; T cell proliferation response was measured by the 3H-thymidine incorporation method.
Figure 9:
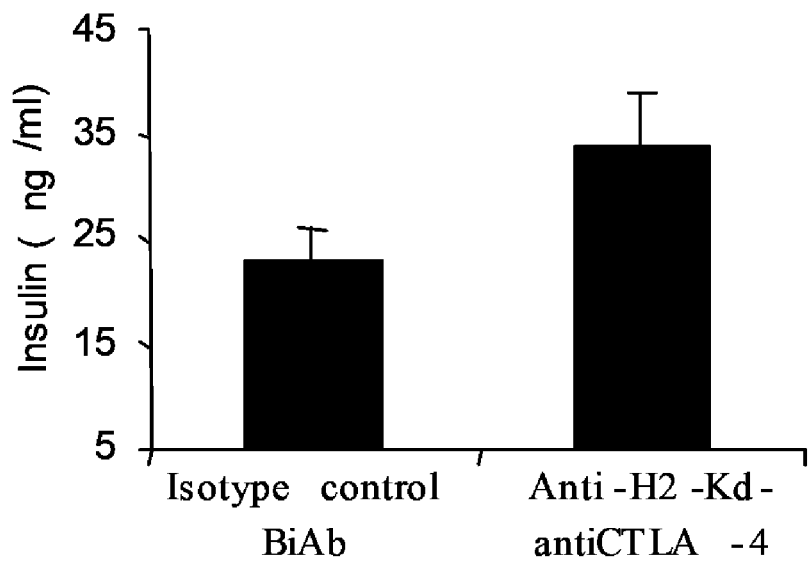
FIG. 9 shows on in vitro insulin production assay; islets were isolated from Balb/c mice and used as single cell suspension prepared by trypsin digestion; islet cells were coated with either isotype control BiAb or anti-H2Kd-anti-CTLA-4 BiAb and incubated with spleen cells from mice that are immune to H2-Kd alloantigen; supernatants from all the cultures were discarded after three days and fresh medium was added. Spent medium from days 3-5 cultures were collected and tested for insulin levels using an ELISA kit for murine insulin.

Allogenic cells coated with anti-CTLA-4 antibody induced immune hyporesponsiveness through suppression of pro-inflammatory cytokines IFN-γ and IL-2, and upregulation of the regulatory cytokines IL-10, TGF-β1 and IL-4, presumably through the engagement of CTLA-4 on activated T cells. While re-challenge with alloantigen failed to break the unresponsiveness, a transient recovery from tolerance was observed in the presence of high concentrations of exogenous IL-2, saturating concentrations of neutralizing anti-TGF-β1 and anti-IL-10 antibodies, blocking anti-CTLA-4 antibody and upon depletion of CD4+CD25+ Treg cells. The CD4+CD25+CTLA-4$^{high}$ Treg cells from tolerant mice suppressed the effector function of CD25− T cells from antigen primed mice. Adoptive transfer of these Treg cells into antigen primed mice resulted in a significantly reduced alloantigen specific response. Further characterization demonstrated that the Treg cells with memory phenotype (CD62L−) were more potent in suppressing the alloantigen specific T cell response. These results indicate that the targeted engagement of CTLA-4 has therapeutic potential for the prevention of transplant rejection. Coating BiAb onto pancreatic islets can suppress T-cell response to islets (e.g., FIGS. 8 and 9).

FACS analysis for CD4+/CD25+ T cells was performed: Mice (H2$^K$) were immunized with allogeneic (H2$^d$) mM12 cells or mM12$^{(4)}$ cells along with BiAb. Spleen and lymph node cells were collected, stained with FITC conjugated mouse CD4 antibody or PE-labeled anti mouse CD25 antibody; the CD4+ cell population was gated for the analysis. The percentage of CD25+ cells and the range of percentage of CD4+/CD25+ cells in 5 individual mice from each group were determined.

The inhibition of in vivo alloresponse was analyzed. CBA/J (H2$^k$) mice were immunized with mM12 cells in the presence of BiAb; group 1 received mM12 cells and BiAb on days 0 and 10, and group 2 received mM12 cells on days 0 and 10 but BiAb only on day 10. Spleen cells from naïve mice or mice immunized with mM12 cells alone or mM12 cells with BiAb were stimulated (0.6×10$^6$ spleen cells) in triplicate wells with M12 cells (0.5×10$^5$/well) for 5 days. Lymphocytes were collected, washed, counted and restimulated with M12 cells or ConA for 48 hr for T cell proliferation assay; and spent medium was tested for IL-2 by ELISA.

Figure 3:
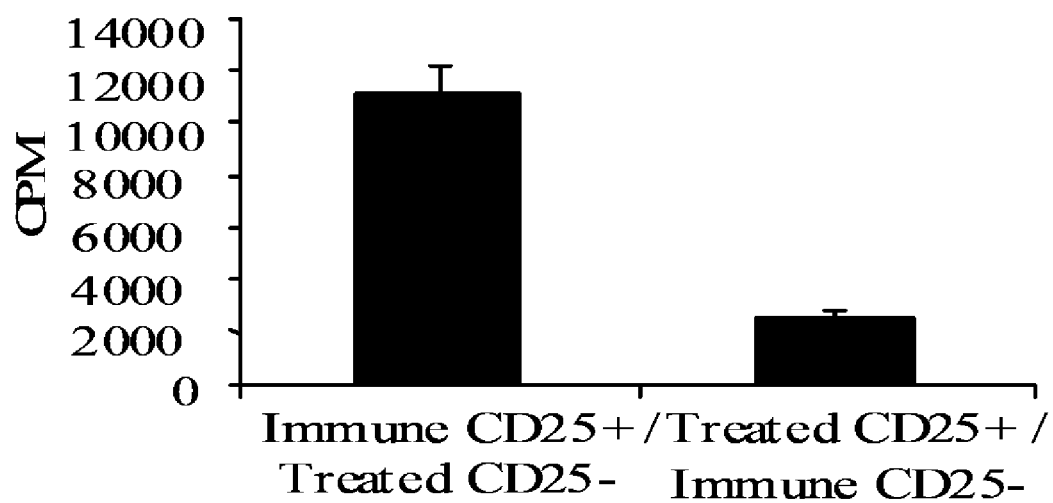
FIG. 3 shows inhibition of T cell proliferation by CD4+/CD25+ T cells: CD4+/CD25+ cells isolated from $H2^K$ mice immunized with mM12($H2^d$) cells were cultured along with splenocytes devoid of CD4+/CD25+ cells from mice immunized with mM12 cells along with bispecific antibody and vice versa. For the allo-proliferation, mitomycin C treated mM12 cells were added to the culture and the proliferation was measured by standard $^3$H-thymidine incorporation.
Figure 4:
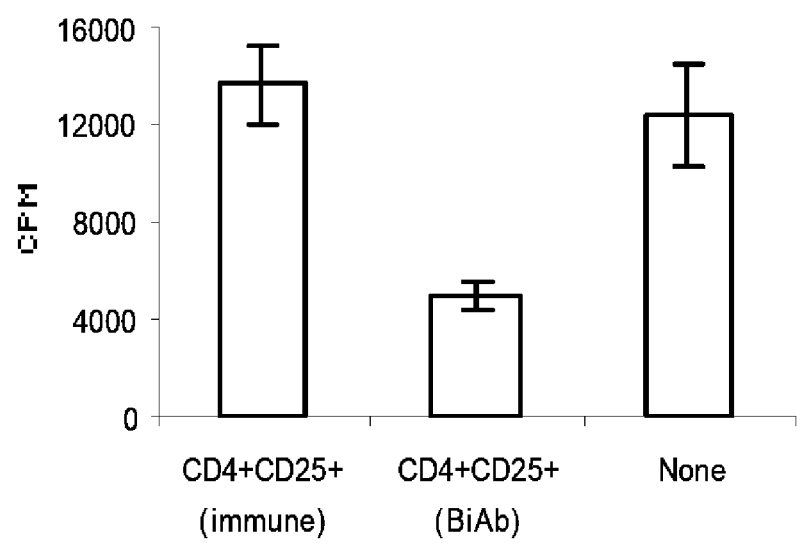
FIG. 4 relates adoptive transfer of CD4+/CD25+ T cells, ex vivo T cell proliferative response to M12 (H2d) cells in mice (H2K) that were primed with M12 cells and adoptively transferred with CD4+/CD25+ cells isolated from mice immunized with mM12 cells and treated with BiAb (BiAb) or untreated controls (immune) or that received no cells (none). Proliferation was measured by standard $^3$H-thymidine incorporation.
Figure 5:
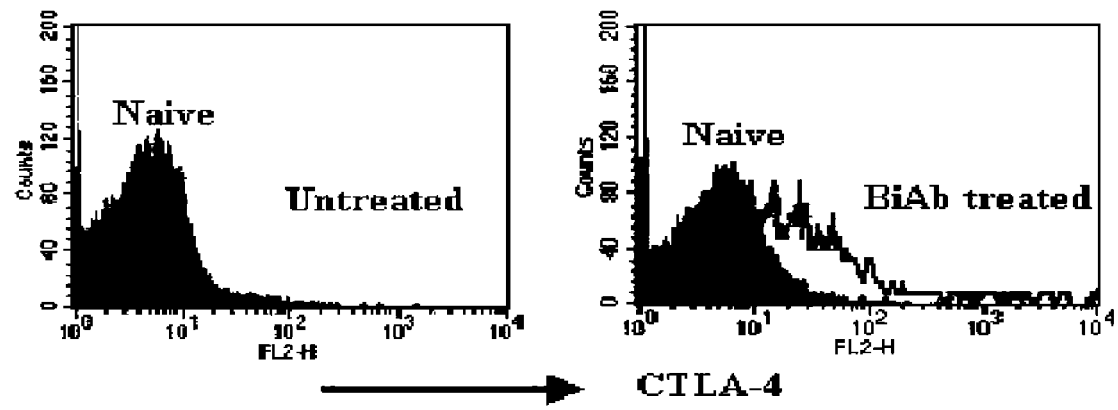
FIG. 5 presents FACS analysis of CD4+/CD25+ cells isolated from naive mice (naïve) mice immunized with mM12 ($H2^d$) cells alone (untreated) or mM12 along with bispecific antibody (BiAb treated) for the expression of CTLA-4.

Data presented herein demonstrate that bispecific antibody (target specific antibody+anti-CTLA-4 antibody) induced tolerance is associated with increased regulatory T cell generation, and demonstrates the effect of these regulatory T cells on effector T cells (e.g., FIGS. 3-5). These results also show that BiAb induced target specific T cell tolerance is associated with specific immunoregulatory T cells. This has been demonstrated through the ability of BiAb treated animals to retain their ability to respond to other antigens not expressed on the BiAb coated cells.

EXAMPLE 3

T Cell Tolerance is Induced upon Targeted CTLA-4 Engagement

Figure 10:
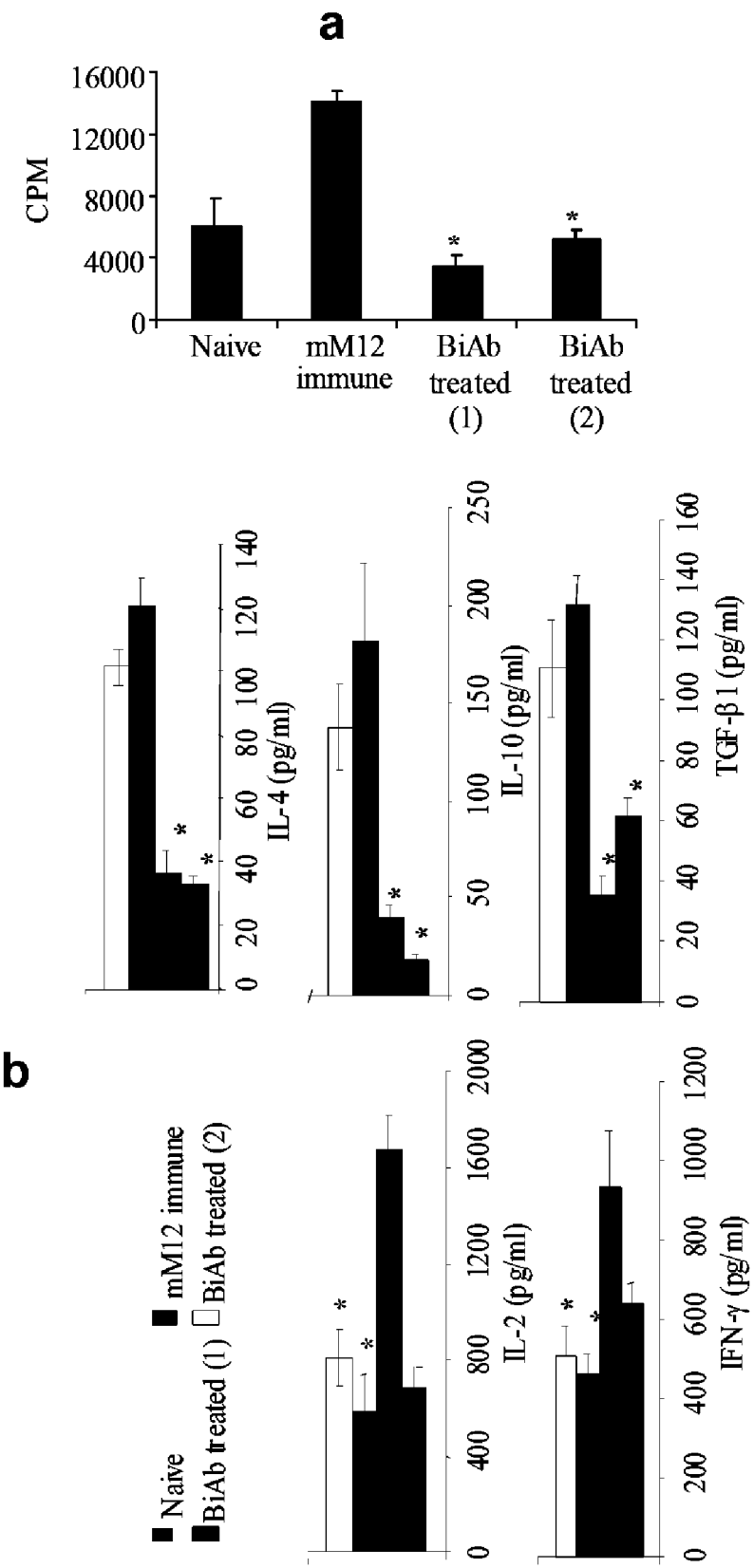
FIG. 10 shows inhibition of in vivo alloresponse; CBA/J ($H2^k$) mice were immunized with mM12 cells; BiAb treated group 1 was inoculated on days 0 and 10 with anti-CTLA-4 antibody (tBiAb) coated mM12 cells and group 2 received isotype control antibody (cBiAb) coated mM12 cells on days 0 and tBiAb coated mM12 cells on day 10. Spleen cells ($0.5\times10^6$ cells/well) from naïve mice (naïve) or mice immunized with cBiAb coated mM12 cells (mM12 immune) or with tBiAb coated mM12 (BiAb treated 1 and 2) were stimulated in triplicate wells with mitomycin C treated M12 cells ($0.5\times10^5$ well) for T cell proliferation assay; (a) after 48 hrs, these cells were pulsed with $^3$H-thymidne for another 18 hrs and counted in a microβ scintillation counter; (b) spent media were collected after 48 hr from the above cultures and tested for the cytokine response using paired monoclonal antibodies in an ELISA. Results are expressed as mean±SD of triplicate values obtained from 5 individual mice. This experiment was repeated three times with similar results. The p value (statistical significance) was calculated by comparing each value for the treated group with the corresponding value of the mM12 immune group. *, Statistically significant value for treated mice.

To further characterize the immunosuppression induced through the BiAb therapy, control antibody or CTLA-4 antibody coated allogenic mM12 cells were injected into CBA/J mice. Mice in one group (BiAb treated group 2) received anti-CTLA-4 coated mM12 cells only during the challenge immunization to test if the T cell response can be controlled during the secondary immune response. As shown in FIG. 10, spleen cells from mice immunized with control antibody coated mM12 cells showed strong T cell proliferative, IL-2 and IFN-γ responses upon ex vivo restimulation with mM12 cells, but mice immunized both times with anti-CTLA-4 antibody coated mM12 cells or only during the second immunization showed significantly reduced T cell proliferation, IL-2 and IFN-γ responses. The alloimmune suppression induced upon CTLA-4 engagement was associated with increased production of IL-4, IL-10 and TGF-β1 (FIG. 10b). Spleen cells from mice that received anti-CTLA-4 antibody coated mM12 cells showed about 3-4 fold higher levels of these cytokines compared to spleen cells from mice that received control antibody coated mM12 cells. Production of low levels of pro-inflammatory cytokines such as IFN-γ and IL-2 along with an increased production of regulatory cytokines, TGF-β1, IL-10 and IL-4 upon CTLA-4 engagement appear to play an important role in suppressing the allo-response in mice that received anti-CTLA-4 antibody coated allogeneic cells.

EXAMPLE 4

Immune Suppression Induced Upon CTLA-4 Engagement is Persistent

Figure 6:
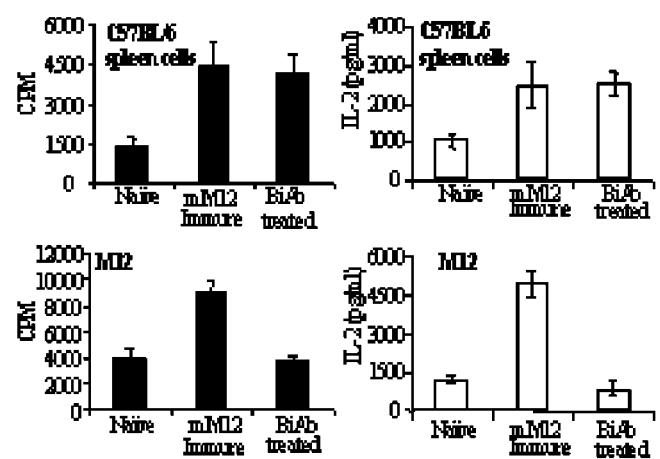
FIG. 6 presents analysis of allotolerance specificity: CBA/J ($H2^k$); mice were immunized with mM12 ($H2^d$) cells in the presence of surface bound anti-TSHR-anti-CTLA-4 BiAb (test BiAb); naïve mice received neither mM12 cells nor BiAb; the mM12 immune group received mM12 cells coated with isotype control BiAb on days 0 and 10; and the BiAb treated group received test BiAb coated mM12 cells on days 0 and 10; mice in mM12 and BiAb treated groups received an intraperitoneal injection of C57BL/6 spleen cells ($1\times10^7$ cells) on day 20; spleen cells from all three groups were stimulated ($0.6\times10^6$ spleen cells) in triplicate wells with either mitomycin treated C57BL6 (H2-kb) spleen cells ($2\times10^5$) or M12 cells ($0.5\times10^5$/well) for 48 hrs. T cell proliferative response (solid bars) was measured by standard 3H-thymidine incorporation (18 hrs) method; spent media collected after 48 hrs from these cultures were tested for IL-2 response by ELISA (open bars).
Figure 7:
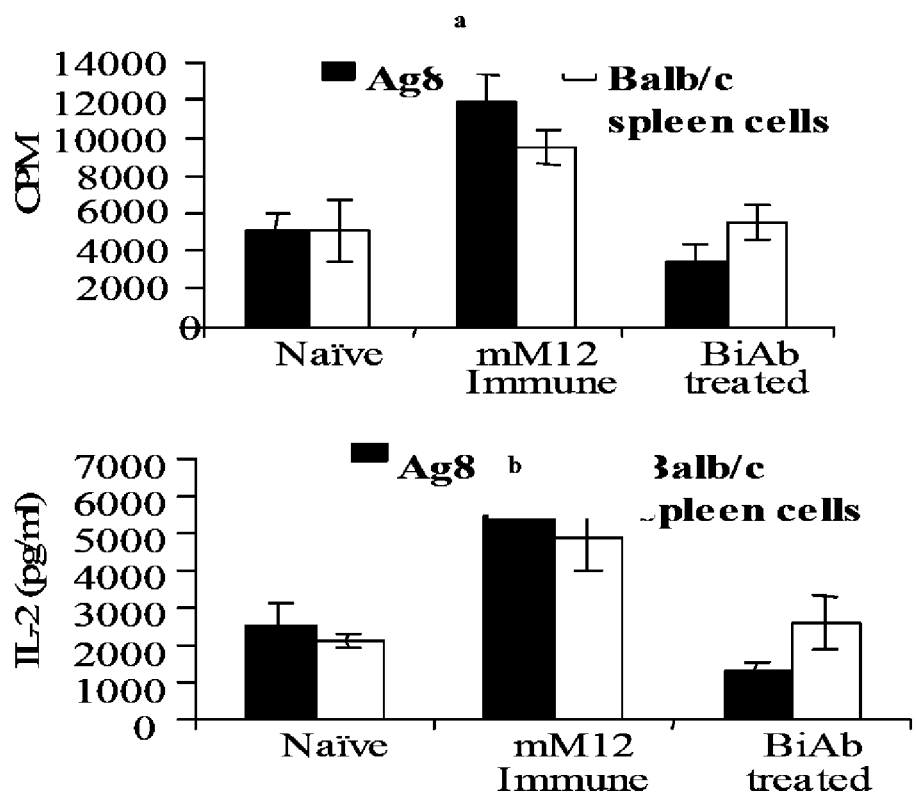
FIG. 7 presents an analysis of the effectiveness of allotolerance: CBA/J ($H2^k$) mice were immunized with BiAb coated mM12 cells as described in FIG. 6. Mice in mM12 and BiAb treated groups received an i.p. injection of Ag8 ($H2^d$) cells ($2\times10^6$) or Balb/c spleen cells ($1\times10^7$) on day 20. Spleen cells from these mice ($0.6\times10^6$)) in triplicate wells were stimulated with mytomycin treated Ag8 cells ($0.5\times10^5$/well) (solid bars) or Balb/c spleen cells ($2\times105$ cells/well) (open bars) for 48 hr.; (a) proliferative response was measured by standard 3H-thymidine incorporation (18 hrs) method; (b) spent medium was tested for IL-2 by ELISA.

FIGS. 6 and 7 show that immune tolerance induced BiAb is persistent and specific to the target cells. The tolerance induced to one target has no effect on the immune system's ability to become tolerant to another target.

Figure 11:
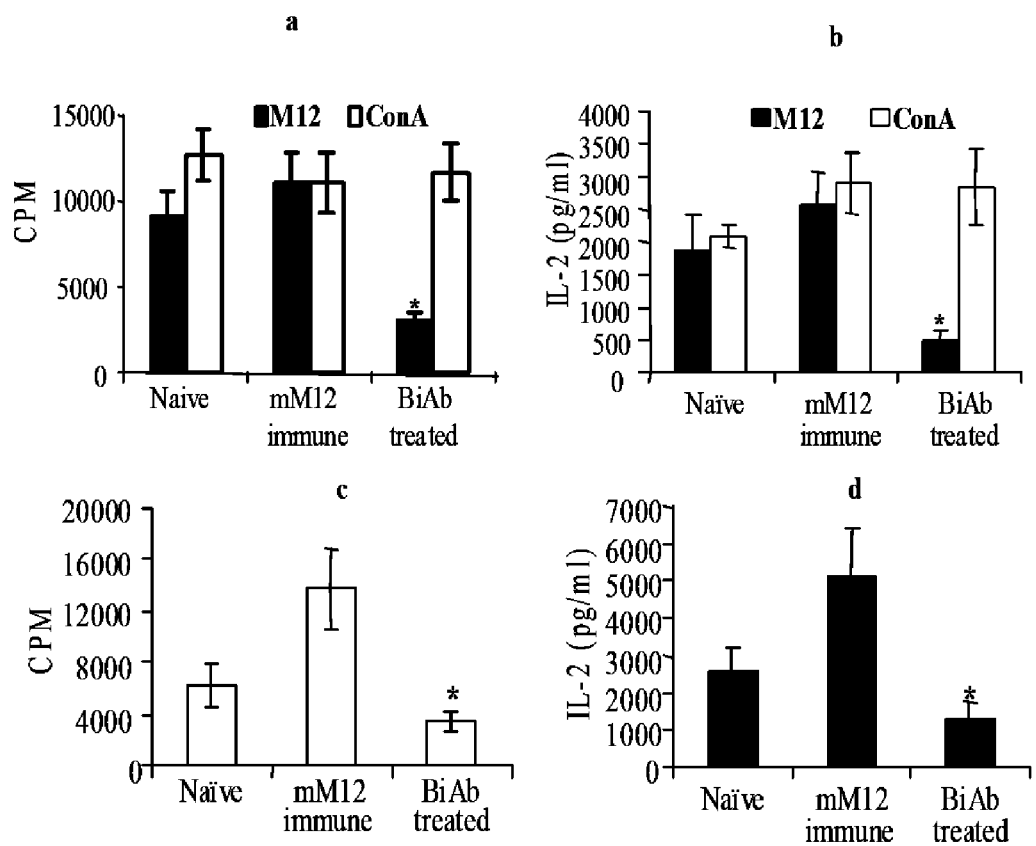
FIG. 11 demonstrates the lasting effect of tolerance induced upon CTLA-4 engagement; CBA/J ($H_2^k$) mice were immunized with BiAb coated mM12 cells on days 0 and 10; these mice were divided into two sets and sacrificed on either day 20 or 70; on day 20, spleen cells from naïve mice (naïve) or mice immunized with cBiAb coated (mM12 immune) or tBiAb coated (BiAb treated) mM12 cells were stimulated in triplicate wells ($0.5 \times 10^6$ spleen cells/well) with mitomycin C treated M12 cells ($0.5 \times 10^5$/well) for up to 5 days; (a) lymphocytes were washed, counted and restimulated with M12 cells or ConA for 48 hr for T cell proliferation assay by $^3$H-thymine incorporation method; (b) spent media collected after 48 hr were tested for IL-2 by ELISA; (c) and (d) on day 60, the second set of mM12 immune as well as BiAb treated mice were challenged with M12 cells, sacrificed on day 70 along with naïve mice and tested for T cell proliferative and IL-2 responses to M12 cells. Results are expressed as mean±SD of triplicate values obtained from 5 individual mice. The p value (statistical significance) was calculated by comparing treated group value with the corresponding value for the control (mM12 immune) group. *, Statistically significant value for treated mice.

To test the persistence of antigen specific unresponsiveness, spleen cells were harvested from mice 10 days after receiving their last BiAb treatment. These spleen cells were stimulated with M12 cells in vitro for 5 days. Cells were collected from these cultures and tested for their ability to respond to restimulation by M12 cells. Spleen cells from tolerant mice showed no sign of recovery from tolerance upon ex vivo re-challenge and failed to proliferate or produce significant amounts of IL-2 in response to tertiary stimulation with M12 cells (FIG. 11a and b). However, cells from both test and control groups responded to mitogenic stimulation (ConA) clearly indicating that the cells were viable and capable of undergoing proliferation. These results suggest that tolerance to alloantigen induced upon CTLA-4 engagement is not readily reversible with ex vivo alloantigen challenge. Next, to test if the tolerance induced upon CTLA-4 engagement can be reversed by in vivo challenge with the alloantigen and whether it is long lasting, both control (mM12 immune) and test (BiAb treated) mice were rested for 50 days, challenged with M12 cells on day 60 and spleen cells from these mice were tested for their response to M12 restimulation ex vivo. As shown in FIG. 11b, spleen cells from tolerant (BiAb treated) mice showed no increase in their response to M12 cells, indicating that the tolerance induced upon CTLA-4 engagement is maintained even after in vivo challenge with the allo-antigen.

EXAMPLE 5

Tolerance Induced Upon Targeted CTLA-4 Engagement is Target Specific

Figure 12:
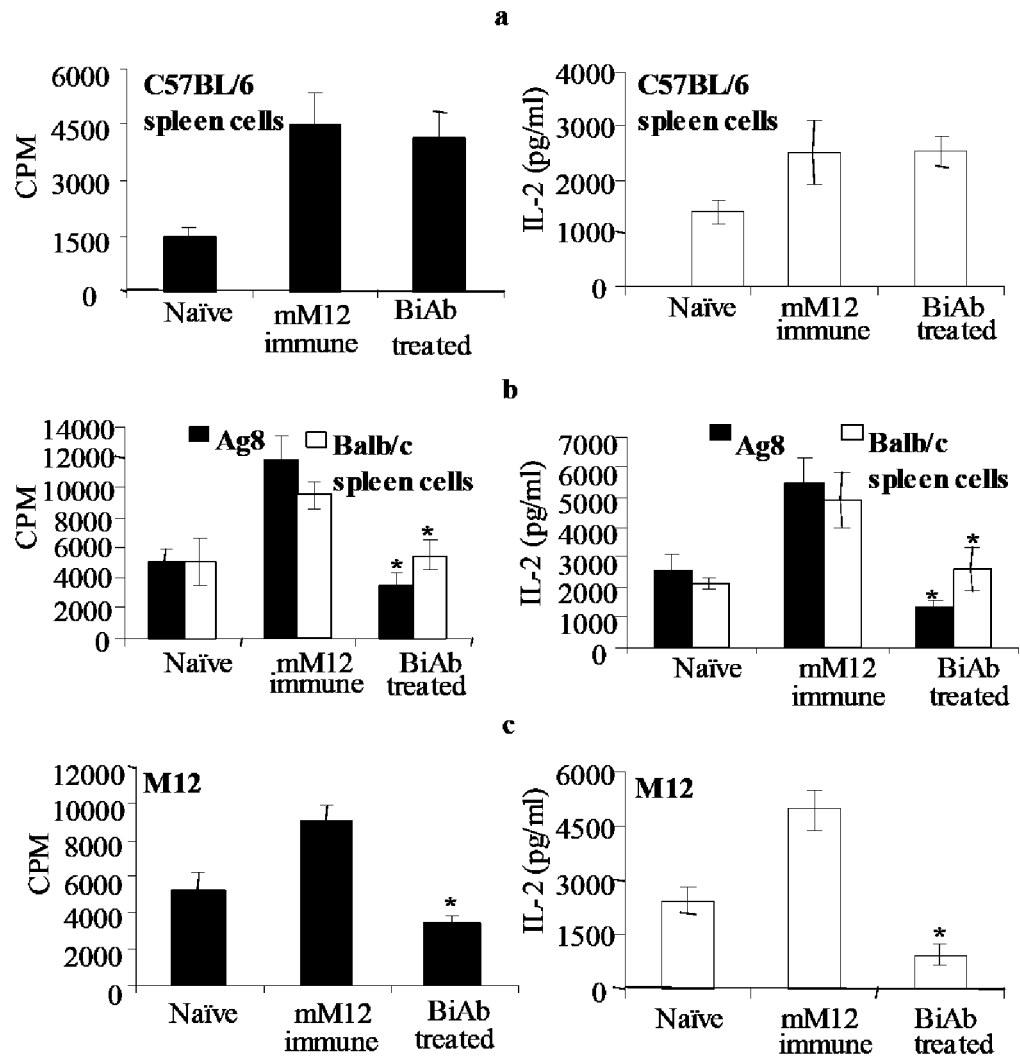
FIG. 12 presents analysis of allo-tolerance specificity; CBA/J ($H2^k$) mice were immunized with mM12 ($H2^d$) cells in the presence of surface bound control or test BiAb; naïve mice received neither mM12 cells nor BiAb; the mM12 immune group received mM12 cells coated with cBiAb on days 0 and 10 and the BiAb treated group received tBiAb coated mM12 cells on days 0 and 10; mice in mM12 immune and BiAb treated groups received C57BL/6 spleen cells ($5 \times 10^6$ cells) on day 20; spleen cells collected from all three groups on day 30 were stimulated in triplicate wells ($0.5 \times 10^6$ cells/well) with either mitomycin C treated (a) spleen cells from C57BL/6 ($H2^b$) ($1 \times 10^5$/well) or (b) Balb/c ($H2^d$) ($1 \times 10^5$/well) mice or Ag8 B cells ($H2^d$) ($0.5 \times 10^5$/well) or (c) M12 cells ($H2^d$) ($0.5 \times 10^5$/well); T cell proliferative response (left panel) was measured by standard $^3$H-thymidine incorporation (18 hrs) method. Spent media collected after 48 hrs from these cultures were tested for IL-2 by ELISA (right panel). Results are expressed as mean±SD of triplicate values obtained from 3 individual mice. This experiment was repeated with similar results. The p value (statistical significance) was calculated by comparing values for the treated group with the corresponding values for the mM12 immune group. *, Statistically significant value for treated mice.

The specificity of suppression of anti-H2d immune response upon CTLA-4 engagement was tested by immunizing mice that were already immunized with BiAb coated mM12 cells with (a) spleen cells from a different mouse strain (C57BL/6 mice, H2b), (b) spleen cells (Balb/c mice, $H2^d$) and a cell-line(Ag8, $H2^d$) on day 20; on day 30, these mice were tested for T cell proliferation and IL-2 production in response to restimulation by spleen cells from C57BL/6 and Balb/c mice, Ag8 and M12 cells. Mice immunized with anti-CTLA-4 antibody coated mM12 cells as well as mice immunized with the control antibody coated mM12 cells showed the same levels of T cell proliferative and IL-2 responses to C57BL/6 spleen cells (FIG. 12 a); however, the pattern of responses to Balb/c spleen and Ag8 cells was more or less similar to that noted when stimulated with mM12 cells (FIG. 12b and c). These results suggest that T tolerance induced upon CTLA-4 engagement during the immune response to $H2^d$ alloantigen is target specific and effective against cells bearing the same antigen (i.e. $H2^d$) but not other antigens (i.e. $H2^b$).

EXAMPLE 6

CD4+CD25+ T Cells are Selectively Expanded in Tolerant Mice

To see whether the tolerance induction was associated with changes in $CD4^+CD25^+$ T cells, naïve, control and tolerant mice were sacrificed on day 20, lymph node and spleen cells from mice were analyzed by flow cytometry for the CD4+ CD25+ population; a significant increase was observed in the percentage of $CD4^+CD25$+ T cells in tBiAb treated (tolerant) mice in both spleen and LNs, but not in the control mice.

$CD4^+CD25^+$ regulatory T cells were induced upon targeted CTLA-4 engagement; CBA/J mice ($H2^k$) were immunized with allogenic ($H2^d$) mM12 cells along with cBiAb or tBiAb. Spleen and lymph node cells were collected from these mice along with naïve mice, stained with FITC conjugated anti-mouse CD4 antibody and PE-labeled anti-mouse CD25 antibody for FACS analysis. $CD4^+$ cell population was gated. The percentage of $CD25^+$ cells and the range of percentages of $CD4^+CD25^+$ cells in 5 individual mice from each group were determined. Expression of CTLA-4 on $CD4^+$ $CD25^+$ cells isolated from naïve mice (naïve), mice immunized with cBiAb coated mM12 ($H_2^d$) (immune) or tBiAb coated mM12 cells were stained with anti-CTLA-4-PE antibody.

To test if the increase in the percentage of $CD4^+CD25^+$ T cells in lymphoid cells from tolerant mice was simply due to the decrease in $CD4^+CD25^-$ T cells, the percentage of both $CD4^+CD25^+$ and $CD4^+ CD25^-$ T cells was measured within the CD4+ T cell population as well as the absolute numbers of $CD4^+CD25^+$ and $CD4^+CD25^-$ T cells in the spleens. There was considerable increase in $CD4^+CD25^+$ T cells within the $CD4^+$ T cells in tolerant mice relative to controls; however, the number of CD4+CD25– T cells within the T cell population was not significantly different in treated and untreated mice. There was a significant increase in the absolute numbers of $CD4^+CD25^+$ T cells in spleens from BiAb treated mice as compared with those from control mice. For example, while control mice showed an average of $1.74 \times 10^7$ CD4+CD25– cells and $1.62 \times 10^6$ CD25+ T cells per spleen, tolerant mice showed an average of $1.76 \times 10^7$ CD4+CD25– cells and $2.5 \times 10^6$ CD25+ T cells. A similar increase in CD25+ T cells was also observed in the lymph nodes of tolerant mice.

It has been shown that CTLA-4 is constitutively expressed on $CD4^+CD25^+$ T cells and involved in mediating the regulatory activity of $CD4^+CD25^+$ T cells in vitro and in vivo. CTLA-4 expression on $CD4^+CD25^+$ T cells was determined. $CD4^+CD25^+$ T cells from tolerant mice showed an increased expression of CTLA-4 compared to $CD4^+CD25^+$ cells from control or naïve mice.

EXAMPLE 7

T Cell Phenotypes in BiAb Treated Mice Upon Ex Vivo Challenge

To test the phenotypic changes of spleen cells from BiAb treated mice, spleen cells were incubated with target (M12) cells and tested for various markers at different time points.

Anti-$H2^d$ response of spleen cells from BiAb treated mice was determined. CBA/J mice ($H2^k$) were immunized with allogenic (H2$^d$) mM12 cells along with cBiAb or tBiAb. Spleen cells collected from naïve, mM12 immune or BiAb treated mice and incubated with mytomycin C treated M12 cells were tested for various molecules by FACS analysis. Cells were stained with FITC labeled anti-mouse CD3antibody and with PE-labeled anti-mouse CD69 antibody after 24 hr, anti-mouse IFN-γ, IL-4, IL-10 and TGF-β1 antibodies after 36 hr, anti-CD62L antibody after 5 days. On day 5, cells were washed and further incubated for 3 days to test for regulatory T cells using FITC labeled anti-mouse CD4 and PE-labeled anti-mouse CD25 antibodies; an aliquot of cells harvested from mice upon sacrifice were stained with CFSE prior to incubation with M12 cells and tested for CFSE dilution on day 7 after staining with PE-labeled anti-mouse CD4 or CD8 antibodies. CD3$^+$, CD4$^+$ or CD8+ cell populations were gated and these experiments were repeated three times with similar results.

The number of cells expressing the early activation marker CD69 was significantly less in spleen cells from BiAb treated mice after 24 hrs of stimulation compared to control immune mice. The numbers of various cytokine secreting cells were determined by intracellular staining after 36 hr stimulation. While the number of IFN-γ secreting T cells were significantly higher in mM12 immune mice compared to tolerant mice, more IL-4, IL-10 and TGF-β1 producing cells were observed in tolerant mice. Expression of memory marker CD62L was tested after 5 days of stimulation. The number of T cells expressing this memory marker was significantly lower in CD3+ cells from BiAb treated mice compared to controls. To test the regulatory T cell phenotype, cells from similar cultures were washed thoroughly, rested for 3 days, and analyzed for CD25 expression. The number of CD4+ cells expressing CD25 in spleen cells from tolerant mice was almost twice that of control immune mice.

The proliferative response to M12 cells by both CD4+ and CD8+ T cells from tolerant and control mice were monitored ex vivo by the CFSE dilution assay. CFSE stained spleen cells were incubated for 7 days with M12 cells and analyzed for CFSE dilution after staining with PE-labeled anti-CD4 or CD8 antibodies. The proliferative responses of both CD4+ and CD8+ T cells were significantly lower in spleen cells from tolerant mice compared to immune controls. Although, both CD4+ and CD8+ T cells from naïve mice showed a prolonged cell division, the number of divisions gone through by these cells from both tolerant and naive mice appeared to be more or less the same suggesting that all the allo-antigen reactive T cells from tolerant mice may not be tolerized and antigen reactive effector cells may still be present in tolerized mice.

EXAMPLE 8

Exogenous IL-2 Partially Reversed the Unresponsiveness to Alloantigen but not Tolerance To test whether exogenous IL-2 can reverse the tolerance induced upon CTLA-4 engagement, M12 cells and varying amounts of recombinant mouse IL-2 (rmIL-2) were added to spleen cells from different mice. FIG. 17 shows the proliferative response of spleen cells after antigenic restimulation either in the absence or presence of exogenously added rmIL-2 and the response to rmIL-2 alone. Although addition of small amounts of rmIL-2 did not induce a significant proliferation of T cells from tolerized mice, a partial recovery (up to 60% compared to that of control mice) was observed in the presence of rmIL-2 at higher concentrations. Further, the hyporesponsive state was reversed only in the presence of both IL-2 and alloantigen, but not with alloantigen or IL-2 alone suggesting that hyporesponsiveness can be reversed only if the antigen and excessive levels of IL-2 are present at the same time.

The roles of cytokines and CTLA-4 in CTLA-4 engagement induced tolerance were determined. Spleen cells collected from tolerant or control mice were incubated alone or with M12 cells (1:10 target: effector ratio). In two cultures of tolerant cells, varying concentrations of rmIL-2 were added and incubated for up to 5 days. On day 2, one set of cultures was pulsed with $^3$H-thymidine for 18 hr to test for T cell proliferation On day 5, remaining cells were washed, rested for 48 hr, equal numbers of viable cells were further incubated with M12 cells in the absence of rmIL-2 for 48 hr and tested for T cell proliferation by $^3$H-thymidine incorporation method. Aliquots of cells were stained with CFSE prior to incubation with M12 cells, supplemented with saturating concentrations of neutralizing anti-mouse IL-4, IL-10, TGF-β1 or the F(ab) fragment of anti-mouse CTLA-4 antibody. Cells were tested for CFSE dilution on day 7 after staining with PE-labeled anti-mouse CD3 antibody. This experiment was repeated with similar results.

To assess the tertiary response to alloantigen by T cells from tolerant mice, effector cells from the above culture were collected on day 5, washed, rested and incubated with fresh target M12 cells. Interestingly, tolerant T cells, which had proliferated in response to IL-2 and alloantigen, were still nonresponsive during a subsequent encounter with alloantigen in a tertiary stimulation, indicating that these cells continue to maintain tolerance and that the reversal of tolerance (as measured by proliferation) occurs only in the presence of high levels of IL-2 and alloantigen.

EXAMPLE 9

IL-10 and TGF-β1 Play an Important Role in the Hyporesponsiveness of T Cells from Tolerant Mice Upon tolerance induction by targeted CTLA-4 engagement, there was an increase in IL-4, IL-10 and TGF-β1 along with a decrease in pro-inflammatory cytokines such as IFN-γ. To determine whether the inhibitory effect induced by CTLA-4 engagement is dependent on these inhibitory cytokines, neutralizing antibodies against them were added to ex vivo cell cultures. Although blockade of IL-4 did not show any significant effect on the proliferative response of tolerant cells to M12 stimulation, neutralization of IL-10 at saturating concentration of antibody resulted in partial recovery (compared to control spleen cells in the absence of neutralizing antibodies) from hyporesponsiveness. However, neutralizing antibody to TGF-β1 alone or in combination with anti-IL-10 antibody resulted in almost complete recovery of T cells from hyporesponsiveness. Cells that could proliferate in the presence of neutralizing antibodies resorted to unresponsiveness after the antibodies were removed and fresh target cells were used in a tertiary stimulation culture.

EXAMPLE 10

CTLA-4 on CD4+CD25+ T Cells is Important in Maintaining Tolerance

CD4+CD25+ T cells from tolerant mice expressed increased levels of CTLA-4 on their surface. To test the role of increased CTLA-4 expression on tolerance, a blocking F(ab) fragment of the anti-CTLA-4 antibody was added at various concentrations. Addition of anti-CTLA-4 F(ab) at saturating concentrations resulted in almost complete recovery of T cells from hyporesponsiveness suggesting that direct engagement of CTLA-4 by B7 molecules on target cells may be necessary to initiate hyporesponsiveness to alloantigen.

EXAMPLE 11

GM-CSF Induced DCs Maintain Semi-matured Phenotype

To determine the effects of GM-CSF treatment on the maturation of DCs, the expression of MHC class II and co-stimulatory molecules were analyzed, as well as the production of pro-inflammatory cytokines from DCs isolated from GM-CSF treated and untreated mice before and after mTg immunization.

The effects of GM-CSF treatment on dendritic cell maturation were determined. CBA/J mice were left untreated or treated with GM-CSF for 5 consecutive days starting on days 1 and 15. In addition, mice were immunized with mTg emulsified in CFA on days 6 and 20. Mice were sacrificed before (days 6 and 20) and after (days 8 and 22) first and second mTg immunization to obtain spleens. Splenocytes isolated from mice sacrificed on day 8 were stained with FITC-anti-CDI Ic and with either PE-anti-MHC II or PE-anti-CD8a & analyzed by FACS. Same cells were stained with FITC-anti-CD11c and with either PE-anti-B7.1, PE-anti-B7.2, or PE-anti-CD40 & analyzed by FACS. DCs were isolated from spleens before or after mTg immunization using magnetic column separation. mRNA was isolated and used in a multiplex RT-PCR assay to detect cytokine transcripts.

Spleens from mice treated with GM-CSF showed increased numbers of $CD11c^+$ cells (7.51%) as compared to untreated controls (3.61%). Despite an increase in the number of dendritic cells, expression levels of MHC class II, B7.1, B7.2 and CD40 were comparable in both GM-CSF treated and untreated mice following immunization with mTg. However, pro-inflammatory cytokines such as TNF-$\alpha$, IL-12 and IL-1$\alpha$, evaluated by RT-PCR, were significantly higher in DCs from untreated mTg immunized mice as compared to DCs from GM-CSF treated mTg immunized mice. These data demonstrate that DCs from GM-CSF treated, but not untreated mice, maintain a semi-mature status following mTg immunization.

Figure 19:
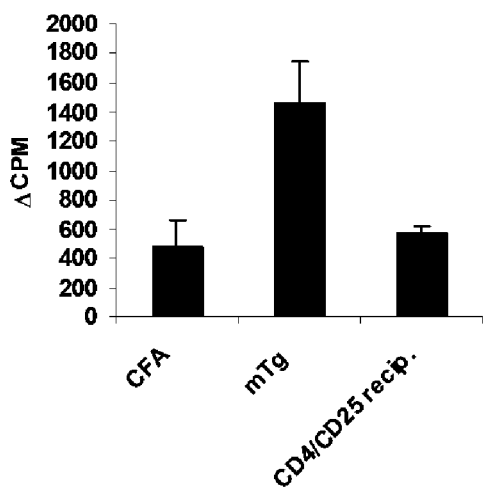
FIG. 19 shows adoptive transfer of CD4$^+$CD25$^+$ T cells from GM-CSF treated mice. CD4$^+$CD25$^+$ T cells were purified from mice treated with GM-CSF and immunized with mTg as described in Material and Methods. Purified CD4$^+$CD25$^+$ T cells were adoptively transferred into mTg immunized mice ($1 \times 10^6$ cells/mouse) and sacrificed on day 18 post-transfer to assess immune response to mTg as compared to controls. (A) Splenocytes were cultured in the presence or absence of mTg. Proliferative response to mTg was measured by $^3$H incorporation assay. ΔCPMs (mTg stimulated CPM—(non-stimulated) background CPM) are plotted. Background CPM were less than 200 in this assay. Spent medium collected at 36 hrs from the above cultures were tested for (B) IFN-γ, (C) IL-4, and (D) IL-10 by ELISA. Results are expressed as mean±SD of values obtained from triplicates of 3 individual mice. * Designates statistically significant difference relative to mTg control mice.
Figure 19:
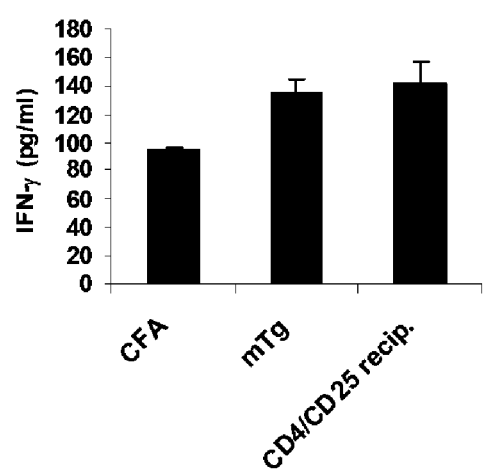
Figure 19:
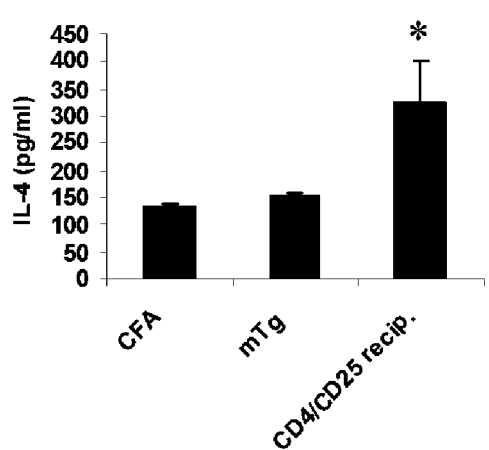
Figure 19:
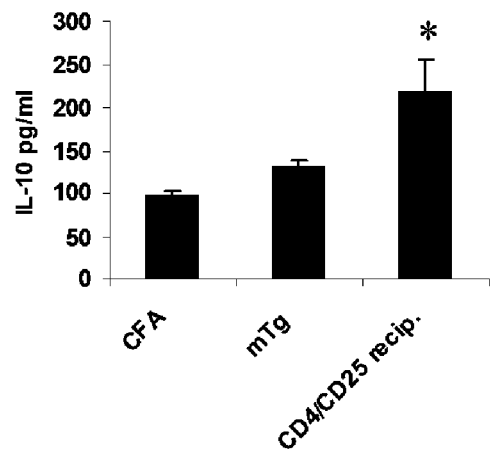

$CD4^+CD25^+$ T cells from GM-CSF treated mice suppress anti-mTg response in viv. To determine whether $CD4^+CD25^+$ T cells from GM-CSF treated mice can suppress mTg specific autoimmune responses in vivo, purified $CD4^+CD25^+$ T cells from GM-CSF treated and mTg primed mice were adoptively transferred to untreated mice that were primed with mTg. As shown in FIG. 19A, mice receiving $CD4^+CD25^+$ T cells from GM-CSF treated mice showed significantly lower mTg-specific proliferation as compared to mTg control mice ($p=0.021$). Analysis of mTg-induced cytokine production by spleen cells from different groups of mice showed similar levels of IFN-$\gamma$ in both $CD4^+CD25^+$ T cell recipient and non-recipient mTg control mice (FIG. 19B). In contrast, cells from recipient mice produced significantly higher amounts of IL-4 ($p=0.045$) and IL-10p=0.035) relative to non-recipient mTg primed mice (FIGS. 19C & D respectively).

IL-10 produced by CD4+CD25+ T cells suppresses mTg specific T cell response. To determine whether IL-10 produced by GM-CSF induced $CD4^+CD25^+$ T cells was responsible for suppressing mTg specific T cell responses, T cells from untreated mTg primed mice were co-cultured with $CD4^+CD25^+$ T cells from mTg primed and GM-CSF treated mice in the presence of an anti-IL-10 receptor ($\alpha$IL-10R) mAbs or isotype control.

Roles of IL-10 in $CD4^+CD25^+$ T cell-induced suppression of mTg specific T cell proliferation were analyzed. CBA/J mice were treated with or without GM-CSF for 5 consecutive days starting on days 1 and 15 and immunized with mTg emulsified in CFA on days 6 and 20. Mice were sacrificed on day 35 to obtain lymph node and spleen cells. $CD4^+CD25^+$ T cells from GM-CSF treated mice and T cells (effector cells) from untreated mice were purified from pooled spleen and lymph node cells using the magnetic separation method. Effector T cells were stained with CFSE, co-cultured with isolated $CD4^+CD25^+$ T cells (5:1 effector:Treg ratio) and stimulated with mTg in the presence of saturating concentrations of $\alpha$IL-10R or isotype control mAb. Either T cell depleted spleen cells or enriched DCs from naïve mice were used as APCs. Proliferative response to mTg was assessed by CFSE dilution as determined by FACS on day 7. Histograms shown are gated on $CD4^+$ T cell population.

T cell depleted spleen cells or isolated DCs from naïve mice were used as feeder cells. mTg primed T cells cultured with $CD4^+CD25^+$ T cells from mTg primed and GM-CSF treated mice in the presence of isotype control Ab showed reduced mTg specific T cell proliferation relative to controls as indicated by reduced CFSE dilution (0.72% and 8.18% relative to 2.42% and 11.46% respectively). However the response was restored to the control levels or higher in the presence of $\alpha$IL-10R mAb (i.e. 2.15% and 16.62%). IL-10 produced by $CD4^+CD25^+$ T cells is required to suppress mTg specific proliferation.

Treatment with $\alpha$IL-10R mAb abolishes GM-CSF induced suppression of EAT. The role of IL-10 in GM-CSF-induced suppression of EAT was investigated GM-CSF treated mice were treated with $\alpha$IL-10R mAb, and sacrificed on day 45 along with control mice to obtain lymph nodes and spleen cells. Splenocytes were stained with CFSE and stimulated with mTg for 7 days. Proliferative response to mTg was assessed by CFSE dilution as determined by FACS. Histograms shown are gated on $CD4^+$ T cell population. Splenocytes were stained with FITC labeled anti-mouse CD4 and PE-labeled anti-mouse CD25 antibodies and analyzed using FACS.

The effects of IL-10 were blocked by the administration of saturating concentrations of $\alpha$IL-10R mAb to GM-CSF treated mice at various times during disease induction. Regardless of the time of administration, almost all animals that received $\alpha$IL-10R mAb, with the exception of some mice treated with $\alpha$IL-10R mAb immediately following GM-CSF treatment (i.e. GM-CSF/$\alpha$IL-10R #2), showed increased mTg-specific proliferation relative to mice that received GM-CSF and isotype control mAb. A significant increase in proliferation was seen in mice receiving $\alpha$IL-10R mAb 5 days after GM-CSF treatment (i.e. GM-CSF/$\alpha$IL-10R #3) or throughout the course of the disease (i.e. GM-CSF/$\alpha$IL-10R #1) ($p=0.001$ and $p=0.005$ respectively). An increase in the frequency of $CD4^+CD25^+$ T cells was observed in all GM-CSF treated mice regardless of the time of administration of $\alpha$IL-10R mAb suggesting that blocking IL-10 had no effect on the expansion of these cells by GM-CSF induced DCs.

As shown in Table I, thyroids from $\alpha$IL-10R mAb groups of mice, with the exception of some mice treated with $\alpha$IL-10R mAb immediately following GM-CSF treatment (i.e. GM-CSF/$\alpha$IL-10R #2), showed more severe lymphocytic infiltration compared to thyroids from GM-CSF/isotype control group of mice. IL-10 is the primary mediator of GM-CSF induced disease suppression.

Effect of GM-CSF treatment on thyroid microenvironment. The effects of GM-CSF on the target organ were investigated by the cell type and cytokine production in the thyroids of treated mice. The effects of GM-CSF treatment on thyroid microenvironment were studied. CFA control, mTg control, and GM-CSF/mTg groups of mice (described under Materials and Methods) were used. Three mice were sacrificed on day 21 to obtain thyroids. Lymphocytes obtained from thyroids were stained with FITC labeled anti-mouse CD4 and PE-labeled anti-mouse CD25 antibodies and analyzed by FACS. Results shown are representative of three independent experiments of 3 mice per group. Total cells obtained from collagenase treated thyroids were maintained in ex vivo for 24 hr, and supernatants were tested for IL-10 and IFN-γ by multiplex cytokine assay. Results shown are representative of two independent experiments. Mean values of 100 data points are shown. Thyrocytes were isolated from thyroid single cell suspensions, mRNA was obtained, and subjected to RT-PCR to detect Fas, FasL and caspase 8 using specific set of primers. β-actin was included as internal control. Control lane represents RT-PCR using positive control mRNA and specific primers. GM-CSF treatment resulted in the expansion of CD8a$^-$ DCs in the periphery; however, this expansion was not reflected within the thyroid. In contrast, there was an increase in the percentage of CD4$^+$CD25$^+$ T cells in the thyroids of GM-CSF treated mice relative to untreated mice (24.57% and 20.06% respectively). Previous studies had shown that MCP-1 preferentially attracts CD4$^+$CD25$^+$ T cells to the thyroid whereas RANTES preferentially attracts CD4$^+$ effector T cells. The levels of these two chemokines were tested. MCP-1 production was comparable among all experimental groups whereas RANTES was undetectable, suggesting these chemokines could not account for the observed increase in CD4$^+$CD25$^+$ T cell frequency in GM-CSF treated thyroids.

Cytokine production by thyrocytes and thyroid resident lymphocytes was quantified. Although a slight increase in IL-10 production with a very small decrease in IFN-γ production was observed in GM-CSF treated mice relative to mTg control mice, these differences were not significant.

Thyrocyte destruction in HT is likely due to Fas mediated apoptosis through increased caspase expression. The expression levels of Fas and Fas ligand (FasL), and caspase 8 on thyrocytes by RT-PCR were tested. Although a slight increase in Fas expression in GM-CSF treated mice was observed as compared to CFA and mTg control mice, there was no detectable FasL expression in any of the groups. Furthermore, there was no substantial difference in the expression levels of caspase 8 between the different groups of mice.

Mechanisms by which GM-CSF treatment can cause suppression of EAT were investigated. GM-CSF can expand DCs and maintain them in a semi-matured status in vivo, promote expansion of CD4$^+$CD25$^+$ T cells, and induce higher levels of IL-10 production required for EAT suppression. These results further extend the results that GM-CSF treatment can expand CD8a$^-$ DCs and CD4$^+$CD25$^+$ regulatory T cells, and suppress EAT.

Although DC function is traditionally associated with the induction of primary T cell responses, there is increasing evidence that they play a critical role in peripheral tolerance. DCs pass through several stages of maturation, and earlier studies have shown that semi-matured DCs play a critical role in the induction and expansion of regulatory T cells. Since GM-CSF treatment led to an increase in the frequency of CD4$^+$CD25$^+$ T cells with regulatory properties, whether GM-CSF exerted its effects by affecting DC maturation was tested. DCs from GM-CSF treated mice displayed a semi-mature phenotype as indicated by high levels of expression of MHC class II and B7 molecules but low levels of expression of pro-inflammatory cytokines relative to untreated mTg control mice. This suggested that GM-CSF treatment most likely induced and/or promoted tolerance through the expansion of semi-matured DCs that are known to aid in the generation of regulatory T cells.

DCs generated by culturing bone marrow precursor cells in low concentrations of GM-CSF are maturation resistant, and inoculation of these DCs pulsed with allo-peptides could prolong allograft survival in vivo. One of the major properties of such DCs is their ability to induce generation of IL-10 producing type 1 regulatory T (Tr1) cells that do not express significant levels of CD25 unless they are activated. However, it was shown that immature and other tolerogenic DCs can help expand IL-10 producing CD4$^+$CD25$^+$ regulatory T cells, which may play an important role in the induction and differentiation of Tr1 cells.

Although several types of regulatory T cells have been described, each with a specific surface phenotype and a cytokine profile, naturally occurring CD4$^+$CD25$^+$ regulatory T cells, which constitute 5-10% of peripheral CD4$^+$ T cells, are the predominant suppressors of autoreactive T cells that escape central tolerance. CD4$^+$CD25$^+$ T cells from GM-CSF treated mice could suppress mTg specific proliferative response of effector T cells in vitro was demonstrated. However, CD4$^+$CD25$^+$ T cells from untreated, but mTg primed mice, failed to show similar suppression of mTg specific responses. Depletion of CD4$^+$CD25$^+$ T cells from in vitro cultures of lymphocytes from GM-CSF treated mice restored mTg specific proliferation. This showed that effector T cells were generated in GM-CSF treated mice like they were in untreated mTg primed mice, but their function was suppressed by CD4$^+$CD25$^+$ T cells that were induced/expanded in GM-CSF treated mice. Adoptive transfer of CD4$^+$CD25$^+$ T cells from GM-CSF treated mice into mTg primed mice resulted in a significant suppression of mTg specific proliferation compared to mTg primed non-recipients. The suppressive property suggested that the population was primarily composed of CD4$^+$CD25$^+$ regulatory T cells. Furthermore, lymphocytes from recipient mice, upon in vitro stimulation with mTg, produced higher levels of IL-10 and IL-4 as compared to mTg primed controls. This indicated that adoptively transferred CD4$^+$CD25$^+$ T cells exerted suppressive effects on recipient effector T cells as seen in GM-CSF treated donor mice.

In order to explore the mechanism of suppression of mTg specific responses by GM-CSF induced CD4$^+$CD25$^+$ T cells, additional studies were carried out. The role of IL-10 both in the expansion and function of CD4$^+$CD25$^+$ T cells in GM-CSF treated mice was tested. Blockade of IL-10 function in vivo using αIL-10R antibody reversed the suppressive effects of CD4$^+$CD25$^+$ T cells from GM-CSF treated mice on mTg specific T cell responses in vitro, and suggested a critical role for this cytokine in GM-CSF induced suppression of EAT. Blockade of IL-10 function in vivo abolished the disease suppressive effects of GM-CSF and allowed development of EAT. Initiation of treatment with αIL-10R antibody at different time points during disease development indicated that IL-10 is required for the induction and/or expansion of CD4$^+$CD25$^+$ T cells in vivo, and whether it is required for merely suppressing autoreactive effector T cell function resulting in consequent suppression of EAT. Irrespective of the time of treatment, blocking IL-10 abolished the EAT suppressive capacity in a majority of mice. Interestingly, the number of CD4$^+$CD25$^+$ T cells was higher in all GM-CSF treated mice, compared to untreated mice, irrespective of αIL-10R antibody treatment. IL-10 is not essential for the expansion of CD4$^+$CD25$^+$ T cells. However, IL-10 produced by these regulatory T cells is critical for the suppression of effector T cells.

TABLE I

Effect of anti-IL-10R Ab on GM-CSF induced EAT suppression

| Group | 0 | 1+ | 2+ | 3+ | 4+ | p value |
|---|---|---|---|---|---|---|
| CFA control | 4 | 0 | 0 | 0 | 0 | |
| mTg control | 0 | 1 | 3 | 1 | 0 | |
| GM-CSF/isotype | 0 | 5 | 0 | 0 | 0 | |
| GM-CSF/αIL-10R #1 | 0 | 0 | 4 | 1 | 0 | 0.002 |
| GM-CSF/αIL-10R #2 | 0 | 2 | 2 | 0 | 0 | 0.09 |
| GM-CSF/αIL-10R #3 | 0 | 0 | 3 | 1 | 1 | 0.008 |

Mice were treated with GM-CSF, immunized with mTg, and further treated with anti-IL-10R mAb or isotype control Ab as described under Materials and Methods. These mice were sacrificed along with control mice on day 45, thyroids collected from mice, at the time of sacrifice, were fixed in formalin, embedded in paraffin, and sectioned for histological H&E staining. Thyroiditis cellular infiltration index was determined as described in Material and Methods. P values were calculated by comparing αIL-10R mAb treated mice with isotype control mice.

IL-10 is a key regulator of inflammation and it can inhibit both Th1 and Th2 type of immune responses through the suppression of pro-inflammatory cytokines and T cell proliferative responses. One of the major mechanisms of IL-10 mediated suppression of T cells is through selective inhibition of the CD28 co-stimulatory pathway. However, in thyroiditis, alternative mechanisms of action of IL-10 have been proposed. Injection of cDNA expression vectors encoding IL-10 into the thyroid can significantly inhibit lymphocyte infiltration and development of EAT, and prevent progression of the disease. This suppressive effect of IL-10 is mediated either through enhancement of Fas-ligand expression on thyrocytes and induction of activation-induced cell death of thyroid infiltrating T lymphocytes, or potent up-regulation of anti-apoptotic molecules such as cFLIP and Bcl-xL, which can prevent CD95-induced apoptosis of thyrocytes. Conversely, direct injection of IL-1 and TNF-α into the thyroids of mTg primed mice induced thyrocyte apoptosis, and indicated that pro-inflammatory cytokines play a critical role in thyroid destruction. This raised the possibility that IL-10 might be mediating its effects through suppression of pro-inflammatory cytokine production.

To see whether the increased IL-10 response in GM-CSF treated mice had any effect on thyroid microenvironment, the levels of expression of various pro-apoptotic molecules in the thyroids of GM-CSF treated mice were tested. Although there was an increase in the frequency of CD4$^+$CD25$^+$ T cells and IL-10 production in the thyroids of GM-CSF treated mice, there was no significant difference in the expression of pro-apoptotic molecules between the thyroids of GM-CSF treated and untreated mTg control mice. GM-CSF mediated suppression of EAT is primarily due to the direct effects of IL-10 on mTg specific effector T cells.

In summary, GM-CSF induced expansion of semi-matured DCs, and thyroglobulin peptide presentation by these DCs led to the expansion of CD4$^+$CD25$^+$ regulatory T cells. IL-10 produced by these regulatory T cells inhibited autoimmune effector functions of mTg specific T cells with consequent suppression of EAT. These results show the therapeutic potential of GM-CSF in EAT and other autoimmune diseases with pathogenesis similar to that of EAT.

EXAMPLE 12

Tolerance Induction through CTLA-4 Engagement

CTLA-4 (CD152) is actively involved in down-regulating T cell activation and maintaining lymphocyte homeostasis. Targeted engagement of CTLA-4 can down-modulate T cell response and suppress allo- and autoimmune responses. Targeted CTLA-4 engagement can induce immune tolerance to a specific target through selective induction of an Ag-specific CD4$^+$CD25$^+$CTLA-4$^{high}$ regulatory T cell (Treg cell) population. Allogenic cells coated with anti-CTLA-4 Ab induced immune hyporesponsiveness through suppression of proinflammatory cytokines IFN-γ and IL-2, and up-regulation of the regulatory cytokines IL-10, TGF-β1, and IL-4, presumably through the engagement of CTLA-4 on activated T cells. Although rechallenge with alloantigen failed to break the unresponsiveness, a transient recovery from tolerance was observed in the presence of high concentrations of exogenous IL-2, saturating concentrations of neutralizing anti-TGF-β1 and anti-IL-10 Abs, and blocking anti-CTLA-4 Ab, and upon depletion of CD4$^+$CD25$^+$ Treg cells. The CD4$^+$CD25$^+$ CTLA-4$^{high}$ Treg cells from tolerant mice suppressed the effector function of CD25$^-$ T cells from Ag-primed mice. Adoptive transfer of these Treg cells into Ag-primed mice resulted in a significantly reduced alloantigen-specific response. Further characterization demonstrated that the Treg cells with memory phenotype (CD62L$^-$) were more potent in suppressing the alloantigen-specific T cell response. The targeted engagement of CTLA-4 has therapeutic potential for the prevention of transplant rejection.

Alloantigen-specific T cell tolerance is one of the main goals in preventing graft rejection. Although the search for more directed therapies that target alloreactive T cells in an Ag-specific fashion continues, nonspecific immunosuppressive drugs dominate the current therapeutic strategies. Induction of T cell hyporesponsiveness or tolerance holds potential in promoting long-lasting graft survival without the need for chronic immunosuppressive drugs.

Activation of mature T lymphocytes is a multistep process requiring both Ag-specific triggering of the TCR complex and costimulation mediated through the CD28-B7.1/B7.2 pathway. The CD28 ligands, CD80 (B7.1) and CD86 (B7.2), are found on APCs, and their ligation to CD28 on T cells leads to IL-2 up-regulation and progression through the cell cycle. CTLA-4 is a critical inhibitor of T cell activation as evidenced by the lethal lymphoproliferationseen in CTLA-4 knockout mice. The B7/CD28 pathway plays a primary role in T cell homeostasis, and manipulating this pathway has emerged as a powerful strategy to modulate the immune response with clinical applications. The inhibition of the costimulatory pathway in the presence of antigenic stimulation may result in T cell anergy. This has been successfully used in animal models to prevent allograft rejection by blocking CD86 and/ or CD80, thereby leading to prolonged graft survival. Engagement of CTLA-4, concomitant with Ag stimulation, can suppress T cell function or result in T cell hyporesponsiveness. This observation supports the earlier view that engagement of CTLA-4 concomitant with TCR-MHC Ag complex interaction can result in inhibition of T cell activation despite simultaneous costimulation through CD28. CTLA-4-Ig that can prevent or suppress transplant rejection and autoimmune conditions by blocking costimulation has notbeen shown to promote generation of regulatory T cells (Treg cells). CD28/B7 costimulationis necessary for generation and maintenance of Ag-specific Treg cells.

Engagement of CTLA-4 on alloreactive T cells that are in contact with their target could down-modulate the T cell response. Targeted CTLA-4 engagement can down-modulate autoreactive T cells in a model of autoimmune thyroiditis. This approach induced thyroid Ag-specific tolerance that resulted in disease suppression.

The mechanism of Ag-specific tolerance induction upon CTLA-4 engagement during alloantigen recognition is analyzed herein. In this tolerance induction system, thyroid-stimulating hormone (TSH) receptor-expressing M12 ($H2^d$) cells (mM12 cells) were used as an alloantigen source for stimulating $H2^k$ mice as described herein. A bispecific Ab (BiAb) with specificities for TSHR and CTLA-4, in which the anti-TSHR portion of the BiAb can bind to the TSHR-expressing allogeneic mM12 cells, leaving the anti-CTLA-4 portion to engage CTLA-4 expressed on the attacking T cells. Tolerance induction can be attained even during the secondary immune response, but also that alloantigen rechallenge had no effect on this tolerant state. Furthermore, this tolerance induction was associated with selective expansion of a subpopulation of $CD4^+CD25^+$ Treg cells that could down-modulate the alloresponse of T cells from nontolerant mice. The results are as follows.

Figure 20:
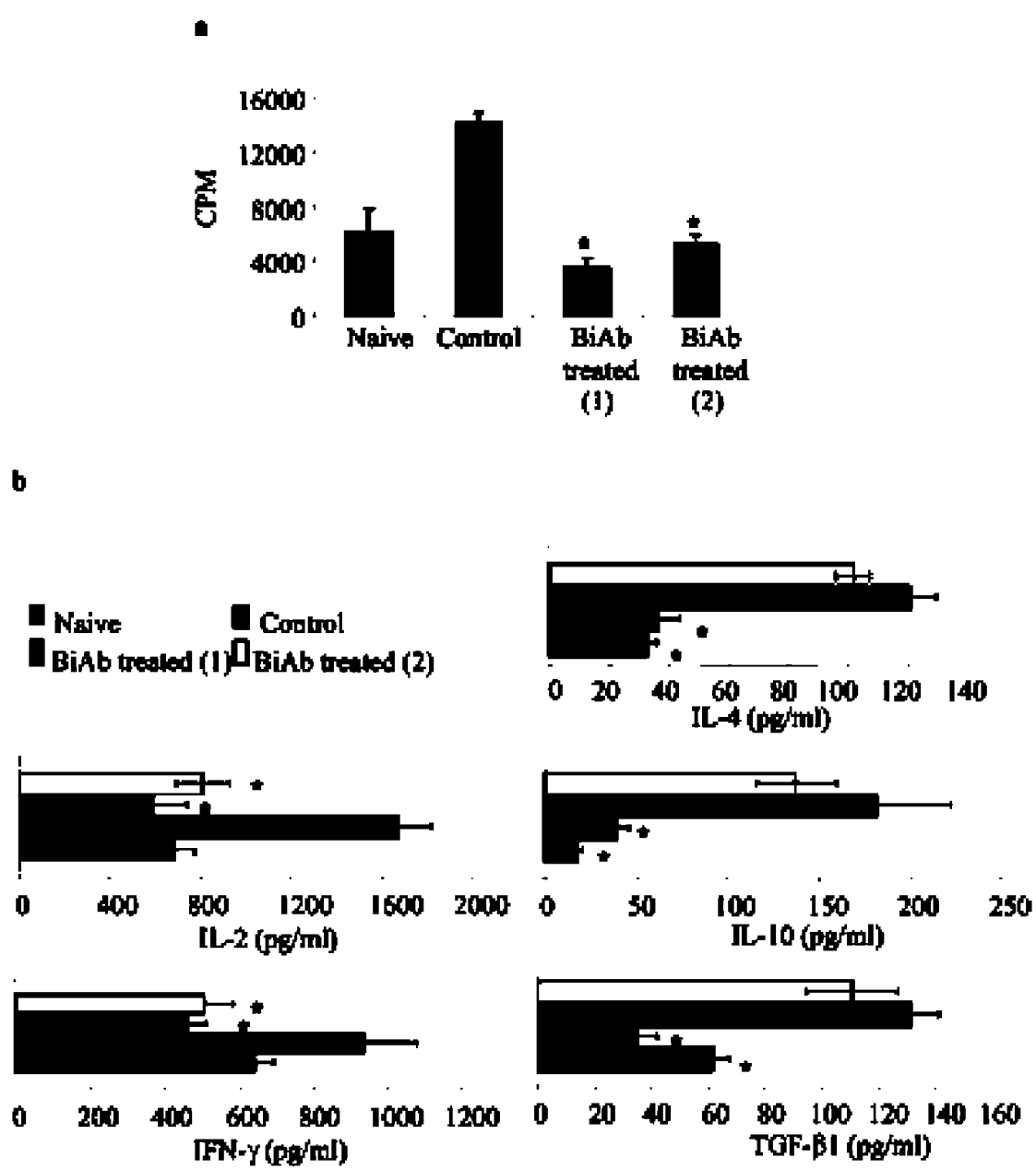
FIG. 20 shows inhibition of in vivo alloresponse. CBA/J ($H2^k$) mice were immunized with mM12 cells as described in Materials and Methods. BiAb-treated group 1 was inoculated on days 0 and 10 with anti-CTLA-4 Ab (tBiAb)-coated mM12 cells, and group 2 received isotype control Ab (cBiAb)-coated mM12 cells on days 0 and tBiAb-coated mM12 cells on day 10. Spleen cells ($0.5 \times 10^6$ cells/well) from naive mice (naive) or mice immunized with cBiAb-coated mM12 cells (control) or with tBiAb-coated mM12 (BiAb treated 1 and 2) were stimulated in triplicate wells with mitomycin C-treated M12 cells ($0.5 \times 10^5$ well) for the T cell proliferation assay. a, After 48 h, these cells were pulsed with [$^3$H]thymidine for another 18 h and counted in a microbeta scintillation counter. b, Spent media were collected after 48 h from the above cultures and tested for the cytokine response using paired mAbs in an ELISA. Background counts per minute (<200) and cytokine (<10 pg/ml) values in spleen cell cultures containing no M12 cells were subtracted from respective test values. Results are expressed as mean±SD of triplicate values obtained from five individual mice. This experiment was repeated three times with similar results.

Engagement of CTLA-4 upon allorecognition suppresses alloimmune response. To address whether targeted CTLA-4 engagement will inhibit an in vivo allogeneic T cell response, control Ab (cBiAb)- or CTLA-4 Ab (tBiAb)-coated allogeneic mM12 cells were injected into CBA/J mice. Mice in one group (BiAb-treated group 2) received tBiAb-coated mM12 cells only during the challenge immunization to test whether the T cell response can be turned down during the secondary immune response. As shown in FIG. 20, spleen cells from control mice showed strong T cell-proliferative, IL-2, and IFN-γ responses upon ex vivo restimulation with mM12 cells. Treated mice, immunized either both times or only during the second immunization with BiAb-coated mM12 cells, however, showed significantly reduced T cell proliferation, IL-2, and IFN-γ responses. Alloimmune suppression induced upon CTLA-4 engagement was associated with increased production of IL-4, IL-I10, and TGF-β1 (FIG. 20b). Spleen cells from mice that received BiAb-coated mM12 cells showed ~3- to 4-fold higher levels of these cytokines compared with spleen cells from mice that received control Ab-coated mM12 cells.

Alloimmune suppression induced upon CTLA-4 engagement is persistent. To test whether restimulation of lymphocytes from BiAb-treated mice in vitro can break tolerance, spleen cells were stimulated with M12 cells in vitro for 5 days. Cells were collected from these cultures and tested for their ability to respond to a further restimulation by M12 cells. These cells showed no sign of recovery from tolerance upon ex vivo rechallenge and failed to proliferate or produce significant amounts of IL-2 in response to tertiary stimulation with M12 cells (FIG. 21, a and b). However, cells from both test and control groups of mice responded to mitogenic stimulation (Con A), clearly indicating that the cells were viable and able to proliferate. These results suggest that tolerance to alloantigen induced upon targeted CTLA-4 engagement is not readily reversible with ex vivo alloantigen challenge.

The duration and reversibility of the CTLA-4 engagement-induced tolerance in vivo was tested. Control and BiAb-treated mice were rested for 50 days and challenged with M12 cells, and spleen cells from these mice were tested for their ability to respond to M12 restimulation ex vivo. As shown in FIG. 21, c and d, spleen cells from tolerant (BiAb-treated) mice showed no increase in their response to M12 cells, suggesting that the tolerance induced upon CTLA-4 engagement is maintained even after in vivo challenge with the alloantigen.

Tolerance induced upon targeted CTLA-4 engagement is target specific. The specificity of suppression of the anti-$H2^d$ immune response upon CTLA-4 engagement was tested by challenging BiAb-treated CBA/J ($H2^k$) mice with different cells. On day 20 after treatment, these mice received either spleen cells from a different mouse strain (C57BL/6 mice, $H2^b$), or spleen cells from BALB/c mice or Ag8 cell line, both syngeneic to M12 cells ($H2^d$). On day 30, these mice were tested for T cell proliferation and IL-2 production in response to restimulation by spleen cells from C57BL/6 and BALB/c mice, Ag8 and M12 cells. Control as well as BiAb-treated mice showed the same levels of T cell-proliferative and IL-2 responses to C57BL/6 spleen cells (FIG. 22a). However, the pattern of responses to BALB/c spleen and Ag8 cells was more or less similar to that noted when stimulated with M12 cells (FIG. 22, b and c). T cell tolerance induced upon CTLA-4 engagement during the immune response to $H2^d$ alloantigen is target specific and effective against cells bearing the same Ag (i.e., $H2^d$) but not other Ags (i.e., $H2^b$).

$CD4^+CD25^+$ T cells are selectively expanded in tolerant mice. Whether the tolerance induction was associated with changes in $CD4^+CD25^+$ T cells was tested. Naive, control, and BiAb-treated mice were sacrificed on day 20, and lymph node and spleen cells were analyzed by flow cytometry for the $CD4^+CD25^+$ population.

$CD4^+CD25^+$ Treg cells are induced upon targeted CTLA-4 engagement. CBA/J mice ($H2^k$) were immunized with allogeneic ($H2^d$) mM12 cells along with cBiAb or tBiAb. Spleen and lymph node cells were collected from these mice along with naive mice, and stained with FITC-conjugated anti-mouse CD4 Ab and PE-labeled anti-mouse CD25 Ab for FACS analysis. The $CD4^+$ cell population was gated. The percentage of $CD25^+$ cells and the range of percentages of $CD4^+CD25^+$ cells in five individual mice from each group were determined. Expression of CTLA-4 on $CD4^+CD25^+$ cells isolated from naive mice (naive), mice immunized with cBiAb-coated mM12 ($H2^d$) (control), or tBiAb-coated mM12 cells (BiAb-treated) was tested by FACS analysis after staining with anti-CTLA-4-PE Ab.

A significant increase in the percentage of $CD4^+CD25^+$ T cells was observed in BiAb-treated (tolerant) mice in both spleen and lymph nodes, but not in the control mice. To test whether the increase in the percentage of $CD4^+CD25^+$ T cells in lymphoid cells from tolerant mice was simply due to the decrease in $CD4^+CD25^-$ T cells, the percentage of both $CD4^+CD25^+$ and $CD4^+CD25^-$ T cells was measured within the $CD4^+$ T cell population as well as absolute numbers of $CD4^+CD25^+$ and $CD4^+CD25^-$ T cells in the spleens. There was a significant increase ($p<0.034$) in $CD4^+CD25^+$ T cells within the $CD4^+$ T cells in tolerant mice relative to controls. However, the number of $CD4^+CD25^-$ T cells within the T cell population was not significantly different in treated and untreated mice. A significant increase ($p<0.021$) in the absolute numbers of $CD4^+CD25^+$ T cells in spleens was observed from BiAb-treated mice compared with those from control mice. For example, while control mice showed an average of $1.74 \times 10^7$ $CD4^+CD25^-$ cells and $1.62 \times 10^6$ $CD4^+CD25^+$ T cells per spleen, tolerant mice showed an average of $1.76 \times 10^7$ $CD4^+CD25^-$ cells and $2.5 \times 10^6$ $CD25^+$ T cells. A similar increase in $CD25^+$ T cells was also observed in the lymph nodes of tolerant mice.

CTLA-4 is constitutively expressed on $CD4^+CD25^+$ T cells and involved in mediating its regulatory activity in vitro and in vivo. $CD4^+CD25^+$ T cells from tolerant mice showed an increased expression of CTLA-4 compared with CD4$^+$CD25$^+$ cells from control or naive mice. However, CD4$^+$CD25$^-$ T cells from all three groups showed little or no surface CTLA-4 expression.

T cell phenotypes in BiAb-treated mice upon ex vivo challenge As a first step toward understanding the mechanism of T cell hyporesponsiveness to allogeneic target and Treg cell generation in BiAb-treated mice, the phenotypic changes of T cells from BiAb-treated mice were tested upon ex vivo challenge with target (M12) cells.

Spleen cells were incubated with M12 cells and tested for various markers at different time points. The number of cells expressing the early activation marker CD69 was significantly less in spleen cells from BiAb-treated mice after 24 h of stimulation compared with control immune mice. T cells secreting various cytokines were detected by intracellular staining after 36-h stimulation. While the number of IFN-γ-secreting T cells was significantly higher in mM12 immune mice compared with tolerant mice, an increase in IL-4-, IL-10-, and TGF-β1-producing cells was observed in tolerant mice. Because low levels or no expression of CD62L is correlated with the memory phenotype, its expression after 5 days of stimulation was tested. The number of T cells expressing low levels of CD62L was significantly lower in CD3$^+$ cells from BiAb-treated mice compared with controls. To test the Treg cell phenotype, cells from similar cultures were washed thoroughly, rested for 3 days, and analyzed for CD25 expression. The number of CD4$^+$ cells expressing CD25 in spleen cells from tolerant mice was almost twice that of control immune mice. CFSE-stained spleen cells were incubated for 7 days with M12 cells and analyzed for CFSE dilution. The proliferative responses of both CD4$^+$ and CD8$^+$ T cells were significantly lower in spleen cells from tolerant mice compared with immune controls. However, the number of divisions undergone by these cells from both tolerant and control mice appeared to be more or less the same.

Exogenous IL-2 partially reversed the unresponsiveness to alloantigen but not tolerance. To test whether exogenous IL-2 can reverse the tolerance induced upon CTLA-4 engagement, M12 cells and varying amounts of rmIL-2 were added to spleen cells from different mice. The role of cytokines and CTLA-4 in CTLA-4 engagement-induced tolerance were analyzed. Spleen cells collected from tolerant or immune mice were incubated alone or with M12 cells (1:10 target: effector ratio). Cultures of tolerant cells received varying concentrations of rmIL-2 and were incubated for up to 5 days. On day 2, one set of cultures was pulsed with [$^3$H]thymidine for 18 h to test for T cell proliferation. On day 5, the remaining cells were washed and rested for 48 h, and equal numbers of viable cells were further incubated with M12 cells in the absence of rmIL-2 for 48 h and tested for T cell proliferation by the [$^3$H]thymidine incorporation method. Aliquots of cells were stained with CFSE before incubation with M12 cells, supplemented with saturating concentrations of neutralizing anti-mouse IL-4, IL-10, TGF-β1, or the Fab of anti-mouse CTLA-4 Ab as described in Materials and Methods. Cells were tested for CFSE dilution on day 7 after staining with PE-labeled anti-mouse CD3 Ab. This experiment was repeated with similar results.

The proliferative response of spleen cells after antigenic restimulation either in the absence or presence of exogenously added rmIL-2 was observed. Although addition of small amounts of rmIL-2 did not induce a significant proliferation of T cells from tolerized mice, a partial recovery (up to 60% compared with that of control mice) was observed in the presence of rmIL-2 at higher concentrations. Furthermore, the hyporesponsive state was reversed only in the presence of both IL-2 and alloantigen, but not with either alloantigen or IL-2 alone, suggesting that hyporesponsiveness can be reversed only if the Ag and excessive levels of IL-2 are present at the same time.

To assess the tertiary response to alloantigen by T cells from tolerant mice, effector cells from the above culture were collected on day 5, washed, rested, and incubated with fresh target M12 cells. Tolerant T cells, which had proliferated in the presence of IL-2 and alloantigen, were nonresponsive during a subsequent encounter with alloantigen in a tertiary stimulation, indicating that these cells continue to remain tolerant and that the reversal of the proliferative response does occur only in the presence of high levels of IL-2 and alloantigen.

IL-10 and TGF-β1 play an important role in the hyporesponsiveness of T cells from tolerant mice. Upon tolerance induction by targeted CTLA-4 engagement, an increase in IL-4, IL-10, and TGF-β1 was observed, along with a decrease in proinflammatory cytokines such as IFN-γ. To determine whether the suppressive effect induced by CTLA-4 engagement is dependent on these inhibitory cytokines, neutralizing Abs against them were added to ex vivo cell cultures. Whereas blockade of IL-4 did not show any significant effect on the proliferative response of tolerant cells to M12 stimulation, neutralization of IL-10 resulted in partial recovery (compared with control spleen cells in the absence of neutralizing Abs) from hyporesponsiveness. However, neutralizing Ab to TGF-β1 alone or in combination with anti-IL-10 Ab resulted in almost complete recovery of T cells from hyporesponsiveness. As seen with exogenous IL-2, subsequent incubation of cells collected from these cultures with target cells in the absence of neutralizing Abs showed that reversal of proliferative response in the presence of cytokine-neutralizing Abs was also transient.

CTLA-4 on CD4$^+$CD25$^+$ T cells is important in maintaining tolerance. CD4$^+$CD25$^+$ T cells from tolerant mice expressed increased levels of CTLA-4 on their surface. To test the role of increased CTLA-4 expression on tolerance, Fab of a blocking anti-CTLA-4 Ab was added at various concentrations. Addition of anti-CTLA-4 Fab at saturating concentration resulted in almost complete recovery of T cells from hyporesponsiveness, suggesting that engagement of CTLA-4 on target cells may be necessary to initiate hyporesponsiveness to alloantigen.

Role of CD4$^+$CD25$^+$ T cells in targeted CTLA-4 engagement-induced tolerance. To see whether CD4$^+$CD25$^+$ Treg cells have a role in down-regulating alloantigen-specific T cell responses, CD4$^+$CD25$^+$ and CD25$^-$ T cells from both tolerant and control mice were isolated using magnetic cell separation systems.

The role of CD4$^+$CD25$^+$ T cells in CTLA-4 engagement-induced tolerance was determined. Spleen and lymph node cells collected from cBiAb- or tBiAb-coated mM12 cell-immunized mice were combined and then fractionated into CD25$^-$ and CD25$^+$ T cell populations. CD25$^-$ and CD25$^+$ (5×10$^5$ cells/well) cells were incubated individually or in combinations with M12 cells (0.5×10$^5$ cells/well) in 96-well plates or in 24 Transwell plates with 0.1-μm pore size inserts. After 48 h, cells were pulsed with [$^3$H]thymidine for 18 h to measure T cell proliferation. Spent media from the assay were tested for various cytokines using multiplex cytokine assay using Luminex technology.

CD4$^+$CD25$^+$-depleted CD3$^+$ cells from tolerant mice, but not control mice, showed a significantly enhanced proliferative response to M12 cells. Cultures devoid of CD25$^+$ cells from tolerized mice responded normally and showed little or no regulatory cytokine responses upon restimulation with alloantigen. Although both IL-10 and TGF-β1 responses were mainly restricted to CD25⁺ T cells, the major source of IL-4 was found to be CD25⁻ T cells. When CD4⁺CD25⁺ cells from tolerant mice were cocultured with CD25⁻ T cells from immune mice, the response to M12 cells was significantly suppressed. However, addition of CD4⁺CD25⁺ T cells from immune mice to CD25⁻ T cells from tolerant mice failed to suppress the T cell response to M12 cells.

Contact dependence is the predominant mechanism in maintaining tolerance. A Transwell chamber assay was performed to investigate whether the tolerance induction by CD4⁺CD25⁺ cells is mediated primarily by soluble factors or requires T-T cell contact. CD4⁺CD25⁺ T cells from tolerant mice suppressed the proliferation of lymphocytes from control mice. Separation of the two populations (CD4⁺CD25⁺ cells and CD25⁻ T cells) in Transwell chamber showed virtually the same effect noted when CD25⁺ cells were depleted. Furthermore, although CD25⁺ cells from tolerant mice induced unresponsiveness of CD25⁻ T cells, maintaining them in separate chambers with M12 cells did not show a similar suppression. However, the presence of M12 cells in both chambers resulted in ~30% reduction in the proliferation, suggesting that cytokine production by CD4⁺CD25⁺ T cells requires alloantigen stimulation, and that these cytokines have an effect, albeit low, on CD25⁻ cells that are in contact with alloantigen. Coculturing CD4⁺CD25⁺ and CD25⁻ T cells in the same chamber resulted in maximum suppression. Direct cell-cellcontacts (target-regulatory, target-effector, and regulatory-effector contacts) is required for optimal inhibition by CD4⁺CD25⁺ T cells from tolerant mice.

Tolerance induced upon CTLA-4 engagement can be adoptively transferred. M12 cells ($H_2^d$) and C57BL/6 mice ($H2^b$) spleen cell-primed mice were injected i.v. with CD4⁺CD25⁺ T cells from tolerant and control mice. These mice were challenged with M12 cells after 2 h, and 15 days later were sacrificed and tested for their ability to respond to target cells.

An adoptive transfer of CD4⁺CD25⁺ Treg cells was observed. Donor CBA/J mice ($H2^k$) were immunized with allogeneic ($H2^d$) mM12 cells along with cBiAb (control) or tBiAb (test). A total of 5×10⁶ CD4⁺CD25⁺ T cells isolated from control (control) and test (BiAb-treated) donor mice was transferred to the recipient mice separately 2 h before challenge immunization with M12 cells or C57BL/6 spleen cells on day 20. Spleen cells were collected from recipients along with control mice that received no T cells (none) on day 35 and tested for ex vivo T cell proliferative and IL-2 responses to M12 cells or C57BL/6 spleen cells.

Spleen cells from recipient mice that received CD4⁺CD25⁺ T cells from tolerant mice showed significantly reduced proliferative and IL-2 responses to M12 cells relative to spleen cells from non recipient and control CD4⁺CD25⁺ T cell recipients. Spleen cells from recipients were also challenged ex vivo with C57BL/6 spleen cells. CD4⁺CD25⁺ T cells from neither tolerant nor control mice had any effect on proliferative or IL-2 responses to C57BL/6 spleen cells and showed the target specificity of transferred tolerance.

CD4⁺CD25⁺ T cells with the memory phenotype are more potent in inducing hyporesponsiveness. To localize this regulatory effect to the memory or naive populations, CD4⁺CD25⁺ T cells from tolerant mice were further separated into CD62L⁺ and CD62L⁻ fractions and tested for their surface CTLA-4 expression, and their ability to produce IL-10 and TGF-β1, and to suppress T cell-proliferative responses.

The effectiveness of CD4⁺CD25⁺ Treg cell subpopulations in inducing hyporesponsiveness was determined. CBA/J ($H2^k$) mice were immunized with anti-CTLA-4 Ab (tBiAb)-coated mM12 ($H2^d$) cells. Spleen and lymph node cells collected upon termination of the experiment were pooled, and CD4⁺CD25⁺CD62L⁺ and CD4⁺CD25⁺CD62L⁻ cells were enriched using magnetic separation systems and tested for surface CTLA-4 expression by FACS analysis. These enriched populations were cultured in the presence of M12 cells for 36 h, and the spent media were tested for IL-10 and TGF-β1 levels by ELISA. CD4⁺CD25⁺ subpopulations were also cocultured with CD25⁻ T cells from control mice at varying regulatory:effector T cell ratios (a total of 0.6×10⁶ cells/well) in the presence of mitomycin C-treated M12 cells (0.5×10⁵/well). The proliferative response was measured by standard [³H]thymidine incorporation (18-h) method.

Relative to CD25⁺CD62L⁺ T cells, CD25⁺CD62L⁻ cells expressed higher levels of CTLA-4, and produced significantly higher amounts of IL-10 and TGF-β1 upon exposure to M12 cells. Both populations failed to produce significant amounts of IL-4, IL-2, and IFN-γ. Although both CD25⁺CD62L⁺ and CD25⁺CD62L⁻ Treg cells showed the potential to suppress the effector T cell responses to alloantigen, the CD25⁺ population with the memory phenotype (CD25⁺CD62L⁻) was more potent.

An effective alloantigen-specific tolerance was induced upon targeted engagement of CTLA-4 and investigated the putative mechanisms associated with this tolerance induction. T cell activation against allogeneic cells was down-regulated significantly only when mice were injected with the anti-CTLA-4 Ab (tBiAb)-coated allogeneic cells, but not with isotype control Ab (cBiAb)-coated cells. Relative to cBiAb-coated cells, tBiAb-coated cells induced significantly higher amounts of IL-10, IL-4, and TGF-β1, and lower levels of IL-2 and IFN-γ production. Moreover, in vitro or in vivo restimulation of T cells from mice injected with tBiAb-coated allogeneic cells failed to break the hyporesponsive state, suggesting that the suppression observed in these mice was not a temporary effect solely mediated by inhibitory cytokines, but was long-lasting and the Treg cells may play a critical role.

To test the specificity of tolerance generated upon targeted CTLA-4 engagement, stimulator cells carrying the same ($H2^d$) or a different ($H2^b$) alloantigen was used. The $H2^k$ mice showed tolerance to different cells bearing the $H2^d$ alloantigens but responded normally to cells bearing the $H2^b$ alloantigens. These results showed that only a subset of T cells with specificity toward a particular target Ag was tolerant, and the remaining cells were unaffected and were able to respond to unrelated alloantigens. T cells could be induced to recover from hyporesponsiveness by antigenic restimulation in the presence of a high dose of exogenous IL-2. However, this did not lead to a permanent reversal of the anergic state, because a subsequent antigenic restimulation of these IL-2-treated cells, in the absence of IL-2, still failed to show a significant response.

Treg cells mediate the persistent hyporesponsiveness to specific Ags after targeted CTLA-4 engagement. CTLA-4 engagement can induce lower IL-2 and higher IL-10 and TGF-β1 production, conditions conducive to the development of Treg cells. CTLA-4 engagement in a tissue/target-specific manner could induce target autoantigen-specific immune tolerance. CTL response to alloantigen-bearing target cells is significantly diminished in mice that received BiAb-coated allogeneic cells. An increase in the number of CD4⁺CD25⁺ Treg cells in both spleen and lymph nodes of tolerant mice relative to the control and naive mice, without a proportionate reduction in CD4⁺CD25⁻ T cell numbers was observed.

Treg cells are often characterized by their constitutive expression of cell surface proteins such as CD25, CTLA-4, and glucocorticoid-induced TNFR family-related gene. However, these proteins are also expressed on activated T cells, and using these molecules as definite markers is not reliable, unless their ability to suppress effector T cell function is determined. The Forkhead transcription factor Foxp3 is specifically expressed in CD4$^+$CD25$^+$ Treg cells and is required for their development. Depletion of these cells can render animals more susceptible to autoimmune diseases. However, the precise mechanism of their induction and action in vivo has not been well defined. Unlike other T cell populations, CD4$^+$CD25$^+$ Treg cells constitutively express CTLA-4 on their surface. In this context CD4$^+$CD25$^+$ Treg cells from allotolerant mice expressed increased levels of CTLA-4 on their surface relative to CD4$^+$CD25$^+$ T cells from immune controls or naive mice. CTLA-4 is important in CD4$^+$CD25$^+$ Treg cell function, the role CTLA-4 plays in CD4$^+$CD25$^+$ Treg cell-mediated tolerance remains controversial. Treatment with Fab of anti-CTLA-4 could temporarily restore the immune response of effector T cells, similar to that noted after exogenous IL-2 treatment. This showed that CTLA-4 is essential for maintaining the tolerogenic function of Treg cells induced upon targeted CTLA-4 engagement.

The reversal of hyporesponsiveness upon CTLA-4 blockade suggests the engagement of constitutively expressed CTLA-4 on Treg cells. In fact studies have demonstrated using B7.1 and B7.2 knockout mice that CTLA-4 engagement by its ligands is necessary for the maintenance and homeostasis of naturally existing CD4$^+$CD25$^+$ Treg cells. In this context, M12 cells, the target cell line used, expresses both B7.1 and B7.2. In addition, contact with target cells is necessary for Treg cells to produce regulatory cytokines and maintain their Ag specificity through a mechanism involving TCR engagement. Alloreactive T cells exist in a hyporesponsive state in the tolerant mice that can be reversed upon removal of CD4$^+$CD25$^+$ Treg cells, or in the presence of excessive IL-2 or IL-10 and TGF-β1 neutralizing Abs. Ag-specific T cells are maintained in an anergic state, perhaps by IL-10 and TGF-β, but not deleted.

One of the major characteristics of Treg cells is their ability to produce IL-10 and TGF-β1, and the role that these cytokines play in Treg cell-induced suppression. Tolerized mice produced higher levels of IL-10 and TGF-β1, and that CD4$^+$CD25$^+$ T cells were the major source of these cytokines. Although T cells from tolerized mice produced higher amounts of IL-4, CD25$^-$ cells, and not the CD4$^+$CD25$^+$ Treg cells, were the source of this cytokine. Neutralization of IL-4 had no significant effect on T cell hyporesponsiveness, whereas neutralization of IL-10 and TGF-β1 restored, albeit transiently, the ability of effector T cells to respond to alloantigen. However, results from Transwell experiments suggested a lesser role for these cytokines when the Treg cells were not in direct contact with the effector cells. The effector cells (CD25$^-$) may need to simultaneously interact with the Treg cells (CD25$^+$) and the target cells (alloantigen). Alternatively, the presence of these cells in the same chamber might prevent dilution of cytokines released by the Treg cells and allow them to more readily bind and act on effector cells that are in close proximity.

CD4$^+$CD25$^+$ Treg cells may originate from naive or Ag-specific T cells. Ag-specific Treg cells can be generated from pre-existing Ag-nonspecific CD4$^+$CD25$^+$ populations as well as from Ag-specific effector T cells. Two major subsets of Treg cells have been reported. The first subset of naturally existing CD4$^+$CD25$^+$ T cells do not show Ag specificity and act through TGF-β1. The second subset of adaptive Treg cells, which can be induced ex vivo, develop as a consequence of activation of mature T cells by suboptimal Ag exposure and/or costimulation. Adaptive Treg cells mainly act through secreted factors such as IL-10. Distinct CD4$^+$CD25$^+$ T cell populations with different expression levels of surface molecules, cytokine secretion patterns, and mode of action may be activated depending on the method used for tolerance induction.

Signaling through CD28 and CTLA-4 controls two distinct forms of anergy in vitro. One form apparently results from TCR occupancy in the absence of CD28 costimulation and CTLA-4 signaling, and can be reversed by IL-2. The other form of anergy is associated with the failure to proliferate after activation, which occurs despite the presence of CD28 costimulatory signals and cannot be reversed by IL-2. The potential of the first form of anergy (lack of CD28 signaling) to induce a long-term tolerance has not been well established. However, CTLA-4 signaling concurrent with CD28 activation and TCR engagement arrests cells from further proliferation and allows them to acquire Ag specificity and, perhaps, differentiate into Treg cells.

The CD62L$^-$ Treg cells were more potent in suppressing the effector T cell response against M12 cells relative to CD62L$^+$ Treg cells. Moreover, the better inhibitory nature of CD62L$^-$ Treg cells correlated with their relatively higher surface expression of CTLA-4 and production of IL-10 and TGF-β1 upon exposure to alloantigen. This is contrary to earlier findings, which showed that both subsets are anergic but the CD62L$^+$ population is more potent on a per-cell basis, and can proliferate and maintain suppressive function far better than the CD62L$^-$ population or unseparated CD4$^+$CD25$^+$ Treg cells. These studies also demonstrated that the CD62L$^+$ subset can be expanded far more easily in culture and is more responsive to chemokine-driven migration to secondary lymphoid organs. This discrepancy could be due to the difference in strategies used for inducing tolerance. In the disclosure herein, CD4$^+$CD25$^+$ Treg cells are most likely Ag specific, and thus, the CD62L$^-$ subset might represent a memory phenotype.

In summary, Treg cells generated by targeted CTLA-4 engagement has therapeutic potential. Induction of alloantigen-specific T cell tolerance to transplants is performed.

Allografts such as pancreatic islets can be coated with anti-CTLA-4 Ab coupled to islet or MHC-specific Ab before transplantation. Alternaïvely, cells that are syngeneic to the MHC Ags of the transplant can be coated with an anti-CTLA-4 Ab coupled to the alloantigen-specific Ab and injected into the recipient to induce tolerance before transplantation.

EXAMPLE 13

Suppression of Experimental Autoimmune Myasthenia Gravis by Granulocyte-macrophage Colony-stimulating Factor is Associated with an Expansion of Foxp3+ Regulatory T Cells Dendritic cells (DCs) have the potential to activate or tolerize T cells in an Ag-specific manner. Although the precise mechanism that determines whether DCs exhibit tolerogenic or immunogenic functions has not been elucidated, growing evidence suggests that DC function is largely dependent on differentiation status, which can be manipulated using various growth factors. The effects of mobilization of specific DC subsets—using GM-CSF and fms-like tyrosine kinase receptor 3-ligand (Flt3-L)—on the susceptibility to induction of experimental autoimmune myasthenia gravis (EAMG) are described herein. GM-CSF or Flt3-L was administered to C57BL/6 mice before immunization with acetylcholine receptor (AChR) and the effect on the frequency and severity of EAMG development observed. Compared with AChR-immunized controls, mice treated with Flt3-L before immunization developed EAMG at an accelerated pace initially, but disease frequency and severity was comparable at the end of the observation period. In contrast, GM-CSF administered before immunization exerted a sustained suppressive effect against the induction of EAMG. This suppression was associated with lowered serum autoantibody levels, reduced T cell proliferative responses to ACHR, and an expansion in the population of FoxP3+ regulatory T cells. Manipulating DCs to expand regulatory T cells is useful for the control of autoimmune diseases such as myasthenia gravis MG.

Autoimmune myasthenia gravis (MG) is a T cell-dependent, Ab-mediated, organ-specific autoimmune disease. Autoantibodies targeted to the skeletal muscle acetylcholine receptor (AChR) impair neuromuscular transmission resulting in muscle weakness. Current therapies for MG produce nonspecific immune suppression, must usually be continued lifelong to maintain disease control, and are associated with significant chronic side effects and enhanced risk for infection and malignancy.

The ideal therapy for MG would eliminate or suppress the autoimmune response to the AChR specifically without otherwise affecting the immune system. The design of an Ag-specific treatment for MG should be attainable since the autoantigen and immunopathogenesis are relatively well-characterized. Available evidence indicates that the autoimmune T cell and Ab responses in MG are highly heterogeneous.

Dendritic cells (DCs) are the most potent APCs of the immune system, and are critically involved in the initiation of immune responses. DCs are involved in the earliest phase of an immune response and their interactions with T cells can profoundly affect subsequent immunity or tolerance. Thus, in addition to their role in activating lymphocytes, DCs also tolerize T cells to Ags, thereby minimizing autoreactive immune responses. The tolerogenic properties of DCs appear to be linked to their differentiation status, such that mature DCs promote immunity, while immature or "semimature" DCs promote tolerance. One of the relevant roles for tolerogenic DCs is the induction and maintenance of Ag-specific regulatory T cells (Tregs). The administration of hemopoietic growth factors has been shown to modulate DC phenotype and functional status. Specifically, the administration of GM-CSF was recently shown to suppress a T cell-mediated autoimmune disease, experimental autoimmune thyroiditis, while administration of fms-like tyrosine kinase receptor 3-ligand (Flt3-L) had opposite effects (10). The observed suppression associated with GM-CSF treatment was dependent upon the presence of IL10-producing CD4+CD25+ Tregs induced by tolerogenic DCs (11).

The effects of mobilization of different subsets of DCs using Flt3-L and GM-CSF on the induction of an Ab-mediated autoimmune disease, experimental autoimmune MG (EAMG) is described. Flt3-L accelerates EAMG development while GM-CSF effectively suppresses clinical disease induction. Significantly, the protective effect of GM-CSF was associated with a selective expansion of CD11c+/CD8a– DCs, reduced circulating anti-AChR Ab levels, T cell proliferative and Th1 cytokine responses, and an increase in the IL-10 response. In addition, GM-CSF treatment also resulted in an expansion of the population of FoxP3-expressing CD4+ T cells.

Mice. Eight-week-old female C57BL6/J mice were purchased from The Jackson Laboratory. Mice were housed in the Biologic Resources Laboratory facilities at the University of Illinois and provided food and water ad libitum. All mice were cared for in accordance with the guidelines set forth by the University of Illinois Animal Care and Use committee.

Purification of Torpedo AChR (tAChR) and induction of EAMG. tAChR was purified from the electric organs of *Torpedo californica* by affinity chromatography using a conjugate of neurotoxin coupled to agarose. Purity of the isolated product was tested by SDS-PAGE. The purified tAChR was used to induce EAMG and as Ag for in vitro testing of immune responses.

To induce EAMG, mice were immunized with 40 μg of tAChR emulsified in CFA in a total volume of 200 μl s.c. along the back and at the base of the tail. The mice were boosted with 20 μg of tAChR emulsified in IFA in 200 μl of volume injected in the flanks and tail base 20 and 50 days after the first immunization. Control mice received an equal volume of PBS in CFA or IFA.

Clinical scoring of EAMG. For clinical examination, mice were observed on a flat platform for a total of 2 min. They were then exercised by gently dragging them suspended by the base of the tail across a cage top grid repeatedly (20-30 times) as they attempted to grip the grid. They were then placed on a flat platform for 2 min and again observed for signs of EAMG. Clinical muscle weakness was graded as follows: grade 0, mouse with normal posture, muscle strength, and mobility at baseline and after exercise; grade 1, normal at rest but with muscle weakness characteristically shown by a hunchback posture, restricted mobility, and difficulty in raising the head after exercise; grade 2, grade 1 symptoms without exercise during observation period; grade 3, dehydrated and moribund with grade 2 weakness; and grade 4, dead.

Flt3-L and GM-CSF treatment. Recombinant mouse GM-CSF and Flt3-L were purchased from BioSource International and Cell Science, respectively. Mice were randomly divided into four groups of eight mice per group: 1) control; 2) tAChR; 3) tAChR+GM-CSF; and 4) tAChR+Flt3-L. Mice were treated with GMCSF (5 μg), Flt3-L (10 μg), and PBS as follows. For mice in groups 1 and 2, PBS was administered i.p. on days 1-9. For mice in group 3, GM-CSF was given i.p. on days 1-5, and PBS was injected IP on days 6-9. Mice in group 4 received Flt3-L administered IP on days 1-9. All mice, except for the control group, were immunized with tAChR (40 μg/mouse) emulsified in CFA on day 10 as described above; the control group received CFA alone. Treatment with GM-CSF, Flt3-L, or PBS was given in a comparable fashion beginning 9 days before each subsequent (booster) immunization as well.

Effects of GM-CSF and Flt3-L on the induction of EAMG. Mice were bled on days 0, 28, and 56. They were then sacrificed on day 70 and lymph nodes, spleens, forelimb, and diaphragm muscle samples were collected. Another set of mice (three mice per experimental group) were treated and immunized as described above, sacrificed 48 h after the completion of treatment, and spleens were collected for analyzing the DCs. Parallel to this experiment, three mice per group were sacrificed 14 days after the completion of the treatment regimen, and lymph nodes and spleens were collected for the analysis of AChR-specific T cell proliferation and cytokine production.

ELISA for anti-tAChR and anti-mouse AChR Ab isotypes. Affinity-purified tAChR (0.5 μg/nml) was used to coat 96-well microtiter plates (Corning Costar 96-well plate; eBioscience) with 0.1 M carbonate bicarbonate buffer (pH 9.6) overnight at 4° C. Affinity-purified mouse AChR purified from mouse carcasses was coated onto 96-well microtiter plates in a similar fashion. The plates were blocked with 10% FBS in PBS at room temperature for 30 min. Serum samples were diluted 1/3000 (for the detection of IgG2a, sera were diluted 1/1000) in blocking buffer were added and incubated at 37° C. for 90 min. After four washes, HRP-conjugated goat anti-mouse IgG, IgG1, IgG2a, or IgG2b (Caltag Laboratories) diluted 1/2000 in blocking buffer were added and incubated at 37° C. for 90 min. Subsequently, tetramethylbenzidine substrate solution (eBioscience) was added, and color was allowed to develop at room temperature in the dark for 15 min. The reaction was stopped by adding 2 M H2SO4, and absorbance values were measured at a wavelength of 450 nm using a Bio-Rad microplate reader (model 550), and the results were expressed as OD values.

AChR-specific Tcellproliferation. Mouse splenocytes were collected and seeded ($4 \times 10^5$ cells/well) in triplicate onto 96-well, flat-bottom microtiter plates in 0.2 ml of RPMI 1640/10% FBS with and without tAChR (5 μg/ml) stimulation. Con A (2 μg/ml) was used as a positive control. For analysis, cells were added to 10 μl of MTT reagents (American Type Culture Collection (ATCC)) after 48-72 h of cultures and incubated for 4 h until a purple precipitate was visible. Detergent Reagents (100 μl) (ATCC) were added, and the cultures were left at room temperature in the dark for 2 h. Absorbance was recorded at 570 nm using Bio-Rad microplate reader.

Measurement of cytokine production. Cytokine response was measured by intracellular cytokine staining and/or by a multiplex suspension assay system. Single-cell suspensions of splenocytes were resuspended at $5 \times 10^6$ cells/ml in RPMI 1640 (Invitrogen Life Technologies)/10% FBS medium and stimulated for 24 h with the tAChR protein (5 μg/ml). Brefeldin A 1× (eBioscience) was added during the last 4 h. Cells were then harvested, washed, and stained using FITC-conjugated anti-CD4 mnAb. Labeled cells were then fixed with fixation solutions (eBioscience) and incubated in the dark overnight at 4° C. Intracytoplasmic staining using PE-conjugated anti-TNF-a, anti-IFN-y, anti-IL-10, and anti-IL-4 Abs (eBioscience) was performed after adding permeabilization working buffer (eBioscience). Data were collected on a FACSCalibur (BD Biosciences), and analyzed using CellQuest software (BD Biosciences).

IL-10 and IFN-y levels were determined in cell-free culture supernatants of the above cultures. Cytokine levels in cell-free supernatants were assayed using multiplex beads immunoassays (BioSource International) and analyzed with a Luminex 100 instrument (Bio-Rad). The suggested minimal detection levels using this kit are 15 pg/ml for IL-10, and 1 pg/ml for IFN-y.

Flow cytometric analysis of DC and Treg phenotypic markers. Single-cell suspensions of spleen and lymph nodes were prepared from mice sacrificed 48 h after completion of the Flt3-L/GM-CSF/PBS treatment regimen for DC analysis. Cells were washed with PBS supplemented with 2% FBS and blocked with antiCD16/CD32 Fc-Block (BD Pharmingen) on ice for 30 min. FITC-conjugated anti-CD11c and PE-conjugated anti-I-Ab (MHC class II), anti-CD8a, anti-CD80, anti-CD86, and isotype control Abs (BD Pharmingen) were used in flow cytometry and analyzed using a FACSAnalyzer (BD Biosciences).

For Treg phenotype analysis, mice were sacrificed 14 days after the completion of the treatment regimen and at the end of the experiment, and splenocytes were isolated. FITC-conjugated anti-CD4 and PE-conjugated anti-CD25 (Caltag Laboratories) were used in flow cytometry and analyzed using a FACS analyzer (BD Biosciences). Mouse regulatory staining kit (w/PE Foxp3 FJK-16s, FITC CD4, and APC CD25) (eBioscience) Abs AQ: A were used for intracellular staining for Foxp3 expression. Purified rat IgG and hamster IgG were used as isotype controls (eBioscience).

RT-PCR. DCs were isolated from splenocytes using a CD11c isolation kit (Miltenyi Biotec). The resulting DC preparation was >90% pure. RNA was extracted using TRIzol and cDNA were synthesized using a ThermoScript RT-PCR System (Invitrogen Life Technologies). A multiplex RT-PCR kit (MaximBio) was used to detect cytokine transcripts. All samples were subjected to electrophoresis using a 2% agarose gel to confirm the specificity of the PCR, and relative quantification of the resulting bands assessed as the ratio of the cytokine transcript to the housekeeping gene, GAPDH. The above experiment was repeated three times to ensure reproducibility.

Confocal microscopy to detect IgG and C3 deposition at the forelimb muscle samples were obtained from mice in each of the four experimental groups (three mice per group). Muscle samples were frozen in liquid nitrogen and stored at −80° C. Sections (10 μM) were taken and allowed to air-dry, then fixed in cold acetone for 10 min. After washing with PBS, the sections were blocked with PBS/5% goat serum (Cappel; MP Biomedicals) for 1.5 h and then washed with PBS, three times for 15 min.

The slides were incubated with tetramethylrhodamine-conjugated anti-BTx (Molecular Probes) (1/500 dilution) for 1 h at room temperature to label the NMJ, then incubated with goat-anti-mouse IgG (Chemicon International), goat anti-mouse complement C3 (Cappel; MP Biomedicals) to colocalize IgG or complement deposits on the NMJ. Anti-IgG and anti-C3 Abs were FITC conjugated (1/500 dilution). The sections were washed with PBS, three times for 15 min and viewed using a fluorescence microscope (Zeiss LSM510 Laser scanning microscopy). Endplate areas were identified as regions of tetramethylrhodamine-conjugated anti-BTx staining. A minimum of 15 sites per muscle with two to three endplates per site were evaluated. The presence of IgG and C3 staining was ascertained visually, and the percentage of endplate regions with visible C3 or IgG staining was determined for each of the experimental groups. All sections were stained and processed in parallel to avoid interassay variations.

Electron microscopy. At the end of the experiment, mice from each of the four experimental groups (three mice per group) were anesthetized with 50 mg/kg sodium pentobarbital and sacrificed. The tibialis anterior muscle and diaphragm were removed and fixed using 2.5% glutaraldehyde in 0.1 M phosphate buffer (pH 7.4) in 4° C. The samples were sectioned and post fixed with 1% osmium tetroxide in 0.1 M phosphate buffer (pH 7.4), dehydrated through a graded ethanol series, and embedded in epoxy resin. Endplates were located in toluidine blue-stained 1-μm semithin sections from the central region of each muscle. Ultra-thin sections (Leica ultracut UCT; Leica Microsystems) from selected areas were contrasted with uranyl acetate and lead citrate and viewed with an electron microscope (JEM-1220 Electron Microscope; JEOL USA). At least five endplate regions with clearly defined nerve terminals and postsynaptic membranes were photographed and evaluated per muscle. Digital micrographs were taken with Gatan slowscan charge-coupled device camera. Endplates were graded visually as "normal" or "abnormal" by an evaluator who was not aware of the identity of the specimen. A "normal" endplate had the following features: readily visualized nerve terminal closely opposed to a postsynaptic membrane with a normal postsynaptic folded pattern. Postsynaptic membrane regions without an associated nerve terminal in the microscopic field were not included in the analysis. The criteria for an "abnormal" endplate required a readily visible simplification of the postsynaptic membrane structure with reduction or loss of the normal postsynaptic folding pattern in a photographed endplate region with a clearly defined nerve terminal and postsynaptic membrane.

Activation of DCs. To determine the effects of GM-CSF and Flt3-L treatment on DC phenotype, the expression of CD11c, MHC class II, and costimulatory molecules, as well as the production of proinflammatory cytokines from GM-CSF-treated, Flt3-L-treated, and untreated mice after tAChR immunization were analyzed. Effect of GM-CSF and Flt3-L treatment on DC phenotype was determined. B6 mice were treated with GM-CSF and Flt3-L before tAChR immunization. Mice were sacrificed 48 h after the last treatment. Splenocytes were collected and stained with FITC-labeled anti-mouse CD11c and with PE-labeled anti-mouse CD8a and analyzed by FACS. DCs were isolated from spleens using magnetic separation columns and used in a multiplex RT-PCR assay to detect cytokine transcripts.

Spleens from mice treated with GM-CSF and Flt3-L had relatively equal percentages of CD11c+ cells and comparable levels of expression of MHC class II, and CD80 compared with untreated tAChR-immunized mice and control (CFA) mice. GM-CSF-treated mice, however, showed an increase in CD8a-CD11c+ cells: 3.55% compared with 1.82% in the untreated group, and 2.05% in the Flt3-L-treated group. GM-CSF-treated mice also had F2 relatively higher levels of expression of CD86.

Statistical analysis. Mean, SD, SE, and statistical significance were calculated using SPSS software applications. Nonparametric Wilcoxon signed test was used for statistical analysis of clinical severity; Fisher's exact test was used for percentage of endplates with IgG/complement deposition and for clinical incidence. Student's t test was used for ELISA, proliferation assays, and flow cytometry. A value of $p<0.05$ was considered significant.

GM-CSF and Flt3-L modulate initial susceptibility to EAMG, and GM-CSF has a sustained suppressive effect on disease incidence and severity. Three groups of mice (eight mice per group) with tAChR on days 0, 20, and 50 were pretreated with GM-CSF, Flt3-L, or PBS before each immunization. Mouse strength was measured on an every other day basis beginning immediately after the first immunization. Mice treated with Flt3-L developed more frequent and more severe myasthenic weakness compared with tAChR-immunized, untreated controls. This effect persisted until −7 wk after the initial immunization, but then disease incidence and severity equalized in this group compared with the control animals. In contrast, mice treated with GM-CSF developed significantly less frequent and severe disease, compared with untreated, tAChR-immunized animals. This relative protection from disease induction persisted until the end of the observation period. By the end of the observation period, 10% of the GM-CSF treated animals had clinical disease compared with 90% in both the Flt3-L and the tAChR-immunized control groups. No animals in the GM-CSF group developed a clinical score more than one at any point during the nine-week observation period.

However, levels of proinflammatory cytokines, such as TNF-a, IL-12, and IL-1/3, evaluated by RT-PCR, were low in GM-CSF treated mice compared with untreated tAChR-immunized controls and Flt3-L-treated mice.

Serum anti-tAChR and anti-mouse AChR Abs. The effects of GM-CSF and Flt3-L treatment on the serum antiAChR Ab responses were monitored at different time points. The serum concentration of anti-tAChR FIG. 24A and anti-mouse AChR Abs by ELISA preimmunization was measured and day 28 and day 56 postimmunization. The titer of anti-tAChR and antimouse Abs did not correlate with disease severity. Treatment with Flt3-L did not significantly affect serum anti-tAChR or anti-mouse AChR Ab levels compared with untreated tAChR-immunized controls. In contrast, treatment with GM-CSF resulted in a decrease in total anti-tAChR IgG Ab response compared with untreated tAChR-immunized controls and had a particularly significant effect on lowering levels of antimouse AChR IgG. This decrease in total antimouse AChR IgG levels reflected a prominent decrease in complement-fixing IgG2b isotypes, while IgGi isotypes were relatively unaffected. These differences were evident on day 28 postimmunization and persisted relatively unchanged at day 56. The anti-IgG2a mAbs yielded a relatively small signal that also decreased in GM-CSF-treated animals, likely resulting from cross-reactivity with homologous IgG2c.

GM-CSF and Flt3-L exert differential effects on tAChR-specific T cell proliferative responses. Spleen cells from mice treated with Flt3-L showed a significantly higher ($p=0.007$) proliferative response to stimulation with tAChR, while spleen cells from mice treated with GM-CSF had a significantly lower ($p=0.0025$) proliferative response to tAChR F4 compared with immunized controls (FIG. 25). Comparable results were obtained using draining lymph node cells.

GM-CSF and Flt3-L treatment affect cytokine production by CD4+ lymphocytes. Cytokine production was analyzed by assessing intracellular cytokine expression profiles in splenic lymphocytes obtained from mice treated with the described growth factors and untreated mice 14 days after the initial immunization with tAChR (FIG. 26). The F5 percentages shown represent cytokine expression by isolated CD4+ cells. There were no significant differences in the amounts of IFN-y, TNF-a, IL-4, or IL-10 expressed by spleen cells from Flt3-L-treated and untreated tAChR-immunized mice. In contrast, spleen cells from GM-CSF-treated mice expressed lower amounts of IFN-y ($p<0.05$) and TNF-a ($p<0.05$) compared with control mice and higher amounts of IL-4 ($p<0.05$). Although the percentage of IL-10-producing cells in GM-CSF-treated mice was not significantly different compared with controls, analysis of cell-free culture supernatants showed significantly higher IL-10 production ($p<0.01$) by cells from GM-CSF-treated mice, as well as decreased production of IFN-y ($p<0.05$).

GM-CSF treatment induces an expansion of the population of CD4+CD25+ and FoxP3-expressing T cells. To determine whether treatment with GM-CSF and Flt3-L affects the relative numbers of Tregs, spleen cells for expression of known Treg surface markers by FACS were tested.

Effects of GM-CSF and Flt3-L on CD25+ and FoxP3+ T cells were tested. Mice were sacrificed at 14 days following treatment with GM-CSF, Flt3-L, and PBS. Splenocytes were isolated from animals and stained with FITC-labeled anti-mouse CD4, APC-labeled anti-mouse CD25, and PE-labeled anti-Foxp3. Gated CD4+ cells were analyzed. Significantly increased numbers of CD4+CD25+ cells were detected in mice treated with GM-CSF compared with untreated tAChR-immunized control animals ($p=0.004$). Gated CD4+ cells were used and the expression of CD25 or FoxP3 was analyzed. A statistically significant expansion in the percentage of FoxP3-expressing (both CD25+ and CD25−) cells was observed in GM-CSF-treated mice compared with untreated tAChR-immunized controls ($p<0.05$). The numbers of CD4+ CD25+ and FoxP3+ cells were not affected by treatment with Flt3-L and were comparable to those observed in untreated tAChR-immunized control mice.

The numbers of F6 CD4+CD25+ and FoxP3+ cells were not affected by treatment with Flt3-L and were comparable to those observed in untreated tAChR-immunized control mice. Significantly increased numbers of CD4+CD25+ cells were found in mice treated with GM-CSF compared with untreated tAChR-immunized control animals (p<0.05). An expansion was found in the percentage of both CD25+ and CD25− cells expressing the transcription factor FoxP3 in GM-CSF-treated mice compared with untreated tAChR-immunized controls, which was also statistically significant (p<0.05). Similar results were observed when animals at the end of the experiment as well as when the analysis was the analysis was performed on splenocytes isolated from the animals at the end of experiment as well as when the analysis was performed in lymph node cells, suggesting that these cells could have an important regulatory role in the GM-CSF-mediated suppression of the disease.

Deposition of IgG and C3 is reduced in the NMJs of GM-CSF-treated mice. To examine the effects of GM-CSF and Flt3-L treatment on the deposition of IgG and complement at the NMJ, immunofluorescence studies were performed on forelimb muscles isolated from mice in each experimental group. Endplates from Flt3-Ltreated and untreated tAChR-immunized controls showed strong staining for C3 and IgG which colocalized to endplate regions as defined by staining with tetramethylrhodamine-conjugated antiBTx, while GM-CSF-treated mice had little or no deposition of C3 or IgG in the majority of endplates regions assessed. Specifically, the percentages of visualized endplates showing immunoreactivity for C3 in each experimental group is as follows: tAChR, 94.1%; Flt3-L, 83.3%; GM-CSF, 35%. For IgG: tAChR, 93.3%, Flt3-L, GM-CSF protects the muscle endplate from anti-AChR Ab-induced morphologic damage. To determine whether the clinical and immunologic changes observed in GM-CSF-treated mice were associated with prevention of the hallmark pathologic findings of destruction of the postsynaptic membrane in EAMG, electron microscopic observations and morphometric analysis were performed on diaphragm muscle obtained from three mice from each experimental group. Endplates from Flt3-L-treated and untreated tAChR-immunized controls showed strong staining for C3 and IgG, which colocalized to endplate regions, while GM-CSFtreated mice had little or no deposition of C3 or IgG in the majority of endplates regions assessed. The immunofluorescence data represented one of at least 15 sites analyzed for each experimental group with approximately two to three endplates visualized per site. FIG. 27 shows deposition of IgG and C3 was significantly reduced in endplates from GM-CSF-treated mice (p<0.001). In mice treated with FLt3-L and in untreated mice endplates showed morphological abnormalities characterized by simplification of the membrane structure and reduction or loss of the postsynaptic folding pattern. In contrast, the endplate regions in GM-CSF-treated mice were largely normal in appearance. Specifically, the percentage of endplates showing clear morphological abnormalities as described for each of the experimental groups is as follows: tAChR control: 66%; Flt3-L-treated: 71.4%; GM-CSF-treated: 27%.

Electron microscopic examination of the postsynaptic folds of motor endplates in GM-CSF-treated, Flt3-L-treated, and untreated EAMG mice was performed. NMJs from the isolated diaphragm muscle from mice in each of the four experimental groups (CFA, tAChR, Flt3-L, and GM-CSF) were observed. Damaged postsynaptic membranes with a reduction or absence of the normal folded pattern was commonly seen in the tAChR and Flt3-L groups, whereas intact or normal postsynaptic folds were observed in the CFA and GM-CSF groups.

The immunopathogenesis of EAMG involves the production of high-affinity anti-AChR Abs whose synthesis is modulated by, and dependent upon AchR-specific CD4+ T cells. The activation of AChR specific T cells is, in turn, determined by their interactions with APCs. As the most potent APC of the immune system, DCs play an important role in MG by presenting self-Ags and promoting the priming and/or boosting of AchR-specific T cells.

Treatment with GM-CSF results in mobilization of CD11c'/CD8a− DCs and a skewing of the immune response to a Th2 polarization in the EAMG mouse model. Accordingly, GM-CSF-treated mice showed only slight increases in the intracellular expression of IFN-y and TNF-a by splenocytes compared with nonimmunized control (CFA) mice, had significantly reduced levels of these cytokines, and increased production of IL-4 and IL-10 compared with control tAChR-immunized mice.

Enhanced production of IL-10 in GM-CSF-treated animals might be expected to promote the synthesis of anti-AChR Abs and possibly make EAMG worse. In fact, the opposite effect was observed.

One possible explanation for this apparent paradox, may be that Ab isotype switching resulted in a shift to less pathogenic (noncomplement-fixing) isotypes, a hypothesis that is supported by reduced circulating levels of IgG2b Abs, as well as reduced IgG and complement deposition at the NMJs in GM-CSFtreated animals. However, total IgG levels were significantly reduced in GM-CSF-treated mice, suggesting that the observed switch to a Th2 immune response in these animals did not result in enhanced B cell responses, at least with regard to autoreactive B cell responses.

In fact, the suppressive effect of GM-CSF on the induction of EAMG may be best explained by the over-riding effects of the expanded population of Tregs induced by tolerogenic DCs on the proliferation of AChR specific T cells and the synthesis of anti-AChR Abs.

GM-CSF-treated mice, having relatively increased numbers of CD4+CD25+ and FoxP3 expressing T cells, are protected against the induction of EAMG, an Ab-mediated, T cell-dependent, autoimmune disease. Despite persistent exposure to endogenous AChR Ag in all the experimental groups, this expansion of cells with a regulatory phenotype occurred only with GM-CSF pretreatment. Not only an expansion of CD25+FoxP3+ cells was observed, but also CD25− FoxP3+ cells having a phenotype consistent with type 1 Tregs (Tr1).

Differential activation of specific subsets of DCs using GM-CSF effectively protects against the induction of EAMG. This effect was likely due to a shift in the cytokine milieu to a Th2 polarization and the generation of increased numbers of CD4+CD25+ and FoxP3 -expressing Tregs, which suppressed anti-AChR T cell and Ab responses.

EXAMPLE 14

Treatment with GM-CSF Over Time Leads to Control of Type-1 Diabetes

The NOD mouse is a well established model for human insulin dependant diabetes mellitus (IDDM). Diabetes onset in NOD mice is believed to be mediated by autoreactive T cells that recognize pancreatic β cell antigens. Both NOD mice and human patients with type I diabetes have a defect in multiple tolerance mechanisms of which a low frequency of CD4+CD25+ regulatory T cells (Treg) has gained the most attention. The significance of Tregs in controlling autoimmunity has been demonstrated in NOD mice by the selective depletion of Tregs which lead to exacerbated T cell mediated destruction of islet cells, whereas adoptive transfer of Tregs can control persistent autoimmunnity.

Tregs can be broadly separated into 'natural' or 'induced' based on their development during thymic central tolerance, or occur as a result of an immune response.

Recent reports support a role for Hassall's corpuscles in the generation of natural Tregs (nTregs) through secretion of thymic stromal lymphopoietin (TSLP). All nTregs are believed to express the transcription repressor Foxp3 which is believed to control Treg development and function. Alternatively, induced or adaptive Tregs are generated in the periphery and produce suppressive cytokines such as interleukin 10 (IL-10) and transforming growth factor-β. The generation of Tregs in either case can be linked to their direct interaction with various dendritic cell subsets. Dendritic cells (DCs), as professional antigen presenting cells, serve as a bridge connecting the innate and acquired immune systems through direct cell-to-cell interactions and/or cytokine production.

NOD mice have been shown to have multiple abnormalities including defective dendritic cell (DC) maturation and function, and deficiencies in $CD4^+CD25^+$ regulatory T cell (Tregs) function. Since myeloid DCs have been implemented in controlling Treg generation in the periphery, expansion of these DCs may increase the interaction between InDCs and Tregs and therefore maintain Treg homeostasis in autoimmune diseases. Hence, restoration of DC and Treg functions to normalcy can be an effective strategy in preventing and/or treating IDDM.

The efficacy of GM-CSF treatment on disease progression in NOD mice was investigated. A continuous treatment with GM-CSF over time leads to protection from disease when compared to untreated healthy and/or diabetic control mice. Analysis of cell populations in both spleen and lymph node tissue reveals an increase in the CD4+CD25+Foxp3+ T cells in treated groups as well as an increase in both IL-10 and TGF-β production. Further, an expansion of myeloid CD8a− DCs with a semimature phenotype in GM-CSF mice was observed, which may be responsible for the expansion of Tregs. Taken together, both the expansion of Tregs and the prevention of diabetes through in vivo administration of recombinant GM-CSF is mediated through the expansion and induction of myeloid semimature DCs.

Suppression of diabetes by GM-CSF. To determine the effects of GM-CSF treatment on diabetes development female NOD mice were either left untreated or treated with 2 µg/mouse/day of GM-CSF for 5 consecutive days on weeks 7 & 9, 11 & 13, or weeks 15 & 17 of age. Since only 60-80% of female NOD mice develop disease, mice were monitored for 30 weeks or until control age matched untreated NOD mice reached >70% diabetic. While treatment with GM-CSF at weeks 7/9, or 11/13 of age (FIG. 28) significantly delayed the onset of diabetes (i.e. ≧500 mg/dl) as indicated by normal blood glucose, treatment on weeks 15/17 had no significant protective effect. These results indicated that relatively early (e.g. when animals might have developed insulitis but not total β cell destruction) treatment with GM-CSF prevents the development of hyperglycemia due to suppression of autoimmune response against the β cells prior to their irreversible destruction. However, if treatment is initiated at an age where disease onset has occurred (i.e. wks 15/17) in a majority of the population, and hence "irreversible" then the regimen seems to be ineffective.

The histopathological staining of pancreatic sections from 18 week old GM-CSF treated, untreated healthy, untreated diabetic mice were obtained. As shown in FIG. 28B, in diabetic and untreated mice, there is severe to moderate peri-insulitis and insultis respectively. In GM-CSF treated mice, sections showed some moderate perinsulitis, but little to no destructive insultiis. In contrast, age matched diabetic mice showed advanced peri-insulitis as well as destructive insulitis.

Continuous treatment with GM-CSF leads prolonged disease onset. Data indicated that early treatment (wks 7 and 9) lead to a significant, but short lived delay in the onset of disease with a declining efficacy post 20 wks of age. Later treatment at wks 11 and 13 had an overall efficacy of 70% protection when compared to controls (FIG. 28). Mechanistically, the 30% disease induction in these mice may be due to the switch from nondestructive insultis to destructive insulitis which usually occurs between 8-12 wks of age. To test whether early and sustained treatment with GM-CSF leads to better and longer lasting protection, female NOD mice were treated bi-weekly from 7-19 weeks of age with recombinant mouse GM-CSF and compared diabetes incidence in age matched untreated control female NOD mice. As indicated in FIG. 29, 80% of untreated mice developed disease by age 20 wks compared to 100% protectin of GM-CSF treated mice. To see how long these animals can remain disease free, the animals were monitored until 40 weeks of age without further GM-CSF treatment. Complete protection was observed through 27 wks of age. By 39 weeks of age 70% of the treated mice developed IDDM (FIG. 29). These results indicated that sustained treatment with GM-CSF initiated at an early age suppresses development of IDDM.

GM-CSF enhances CD4+CD25+ Foxp3+ T cells in NOD mice. It has been demonstrated that CD4+CD25+ regulatory T cells (Tregs) play an essential role in controlling autoimmune responses in NOD mice. Changes in expression of CD4+CD25+ in GM-CSF treated versus untreated mice were analyzed. GM-CSF treated mice from all age groups analyzed showed an expansion in CD4+CD25+ T cells as compared to control mice. Further, an overall decrease in the percentage of CD4+CD25+ T cells in diabetic mice was observed. Foxp3, the forkead/winged helix transcription factor, has been reported to control regulatory T cell function and development. There was a parallel increase in Foxp3 and CD25 expression in both naïve and GM-CSF treated mice. Further, enhanced Foxp3 expression was observed in GM-CSF treated versus untreated groups in both spleen and pancreatic lymph nodes. These results indicated that GM-CSF plays a role in the expansion of Foxp3 positive regulatory T cells.

Adoptive transfer of CD4+CD25+ T cells isolated from GM-CSF treated mice protect when co-transfered with diabetogenic effectors. NOD-scid mice and adoptively transferred splenocytes from a recently diabetic mouse alone or together were used with CD4+CD25+ T cells from GM-CSF treated or untreated donor mice. A delay in disease onset was observed in the co-transfer of naïve CD4+CD25+ donor cells. However, a significant delay in diabetes onset was observed in recipients receiving CD4+CD25+ T cells from GM-CSF treated mice (FIG. 31). Therefore, the protective effect observed was most likely due to the expansion and increased efficacy of CD4+CD25+ T cells in GM-CSF treated mice.

Regulatory Tcells in GM-CSF recipients secrete both TGF-β and IL-10. GM-CSF leads to the expansion of CD4+ CD25+Foxp3+ T cells and that these cells can effectively suppress autoreactive effector cells in vivo. The cytokine milieu produced by splenocytes in GM-CSF treated or untreated mice by ELISA was analyzed (FIG. 32). There was an increase in both IL-10 and TGF-β in GM-CSF treated groups as compared to controls, although the increase in IL-10 was much more apparent. Purified CD4+CD25+ and CD4+CD25− T cells from GM-CSF treated and untreated mice were cultured and compared their cytokine profile. An increase in both TGF-β and IL-10 was found in CD4+CD25+ T cells isolated from both spleen and pancreatic lymph nodes in GM-CSF treated mice as compared to the untreated control mice (FIG. 33).

These results indicate that GM-CSF does indeed lead to the expansion of IL-10/TGF-β producing Foxp3+CD4+CD25+ T cells. CD4+CD25+ and CD4+CD25− T cells were purified from 8 week old GM-CSF treated or untreated female NOD mice and utilized them in a transwell suppression assay. As responder cells, anti CD3/APC stimulated CD4+CD25− T cells were used as responder cells along with varying ratios of CD4+CD25+ T cells in the top transwell. Significant suppression of proliferation in both 1:1 and 2:1 effector to Treg ratio in GM-CSF treated groups versus naïve groups was observed. The CD4+CD25+ T cells did exhibit some suppression but not to the extent of the GM-CSF treated groups. Adding either IL-10 or TGF-b alone had no significant effect in reducing the suppressive function of the Tregs, however, the addition of both antibodies led to proliferation almost to control levels. Taken together, these data indicate that GM-CSF induces the expansion of CD4+CD25+Foxp3+ regulatory T cells that mediate their suppression in a contact independent, IL-10 and TGF-b dependant mechanism.

GM-CSF induces semimature DCs. Dendritic cells have been reported to play essential roles in inducing tolerance through the induction of anergy and regulatory T cells. The ability of DCs to mediate tolerance versus immunity lies in the maturation status. It has been reported that both immature (myeloid and plasmacytoid) and myeloid semimature DCs play roles in maintaining Treg homeostasis. Interestingly, multiple reports show an imbalance favoring immunogenic versus tolerogenic DCs in NOD mice which plays a role in the autoimmune disease progression in these mice. The effect of GM-CSF treatment on DC subtype and maturation was determined. For DC subtype, splenocytes from GM-CSF treated and untreated healthy and diabetic mice were isolated and lymphoid (CD11c+CD8a+) and myeloid (CD11c+CD8a−) populations were compared. A natural imbalance was found favoring CD8a− DCs in untreated groups, but an overall expansion of CD8a− DCs in GM-CSF treated groups. Since maturation status depends on both costimulatory surface marker expression and proinflamatory cytokine production, the effects of GM-CSF on these parameters were analyzed. Spleens from GM-CSF treated and untreated mice had comparable levels of MHCII, B7.1, B7.2, and CD40 marker expression. However, the levels of proinflammatory cytokines, such as TNF-α, IL-12, and IL1β, analyzed by RT-PCR, were significantly higher in DCs from untreated mice and even higher in diabetic mice as compared to GM-CSF treated mice. This evidence indicates that GM-CSF expands myeloid DC populations and maintains them in a semimature status which may play a role in Treg homestasis.

GM-CSF acts on DCs and directly expands CD4+CD25+ Foxp3+ T cells in vivo. GM-CSF treatment leads to the expansion of Foxp3+ Tregs and expands myeloid semimature DCs. To determine whether these DCs maintain tolerance to disease through the expansion of regulatory T cells the NOD scid mouse was used. If GM-CSF treatment tolerizes DCs, then, when compared with wt DCs and encounter with T cells should delay the onset of disease. Naïve CD4+ T cells were adoptively transferred into GM-CSF treated and untreated NOD scid and monitored them for diabetes development. As shown in FIG. 34, there was a significant delay in disease onset in the GM-CSF treated mice when compared to controls. When CD4+CD25− T cells were used as donor cells however the kinetics of disease onset were faster (FIG. 34).

This result indicated that GM-CSF is acting on DCs to influence their tolerizing function on T cell populations. It is possible that GM-CSF is acting on other immune cells which may influence the affects on disease progression observed. In order to rule out this possibility, it was shown that these DCs can specifically mediate tolerance. DCs from both GM-CSF treated and untreated wild type NOD mice were isolated and adoptively transferred these cells into pre-diabetic wild type NOD mice. If the observed tolerogenic effect observed was solely due to the inherent ability of GM-CSF to induce semimature DCs then, a delay in disease development should be seen. GM-CSF DC recipient mice showed a significant delay in disease onset when compared to naïve DC recipients (FIG. 35A). Further, an increase in Foxp3 expression was observed when both spleen and pancreatic lymph node populations were analyzed a week post transfer. Taken together these results demonstrate that GM-CSF leads to the expansion of Tregs through the induction of semimature/tolerogenic DCs (FIG. 35B).

The efficiency of GM-CSF treatment on IDDM in NOD mice was demonstrated. Data demonstrated that GM-CSF can maintain DCs in a semimature status in vivo, expand IL-10/TGF-b producing CD4+CD25+Foxp3+ T cells.

Activation of DCs by foreign antigen leads to a process of maturation. This process involves the upregulation of MHC II, costimulatory markers (CD80, CD86, CD40), and effective production of proinflammatory cytokines. Both upregulation of cell surface markers and cytokine production are essential for mediating an effective immune response. In contrast, immature DCs which express little to no costimulatory markers or proinflammatory cytokines are thought to have more of a tolerogenic quality. A strong T cell interaction with these peptide-MHC (signal 1) without costimulatory interaction (signal 2) leads to T cell anergy. In addition to anergy induction, some studies have shown that iDCs can also expand Tregs both in vitro and in vivo. Recent evidence has found a subset of myeloid DCs where cytokine production resembles iDCs but surface marker expression is indistinguishable from mature DCs. These semimature DCs have been shown to play a major role in the expansion of regulatory T cell. This has been well documented in autoimmune diseases such as EAE, where repetitive injections semimature DCs led to expansion of IL-10 producing Tregs and low amounts of proinflammatory cytokines. These DCs have also been well documenting as the major cell determinants in controlling autoimmune thyroiditis. Data presented herein suggests a semimature DC induced phenotype in GM-CSF treated mice. These bimodal DCs play a key role in mediating tolerance and can fully activate T cells due to their high expression of MHC II molecules but not necessarily elicit an immune response due to their lack of proinflammatory cytokines secretion. Proinflammatory cytokines have been shown to antagonize Treg expansion and development. Data provided herein shows an increase in D4+CD25+Foxp3+ in GM-CSF treated mice as compared to untreated mice. It has been suggested that within both NOD mice and human patients with IDDM that CD4+CD25+ Treg population decrease in both number and function. This trend is also seen in the control groups as healthy mice have less CD25+ cells than treated mice and diabetic mice have even less. In NOD, a similar trend in both the induction of semimature DCs as well as the expansion of CD4+CD25+ T cell populations was observed. In addition, an increase in IL-10 and TGF-B levels in purified CD4+CD25+ populations from GM-CSF treated mice was observed, which were not apparent in control mice. IL-4 levels did not change from control mice and treated mice. No phenotypic skewing effect in NOD mice was observed. Before GM-CSF treatment, an imbalance favoring CD8a− DCs was seen, and still Th1 response occurs. When GM-CSF is administered there is an expansion of these cells which taken together indicates that Th2 responses may not be responsible for the suppression of disease observed and that the expansion of CD4+CD25+ T cells observed may the most contributing factor in the suppression of disease.

In summary, GM-CSF induces the expansion of semimature DCs, which inturn lead to the expansion of CD4+CD25+ regulatory T cells. Data using NOD SCID and adoptive transfer experiments clearly support a mechanism of DC mediated Treg expansion. Therapeutic tools for the maintenance tolerance and prevention and/or treatment of autoimmune disease such as the type-1 diabetes are designed.

Materials and Methods used in relation to Example 14 are provided herein.

Mice: 4-6 week old female NOD/Ltj and NOD scid mice were purchased from Jackson Laboratories (Bar Harbor, Me.). Mice were housed in the Biological Resources Laboratory facility at the University of Illinois-Chicago were they were given food and water ad libitum. Mice were cared for in accordance with the guidelines set by the University of Illinois animal care and use committee. Mice were used at various ages ranging from 7-30 weeks.

GM-CSF & Abs: Recombinant mouse GM-CSF was purchased from either Cell Sciences or Biosource. FITC-conjugated antiCD1 c and PE-conjugated anti-H-2k$^d$ (MHC II), anti-CD8a, anti-CD25, anti -CD80, anti-CD86, and anti-CD40 (BD Phamingen) PE conjugated anti-CD4 (BD Parningen), APC conjugated anti Foxp3 (ebiosciences) Abs were used in flow cytometry. Purified rat IgG2a was used for APC isotype control and rat IgG2b was used for PE and FITC isotypes (ebiosciences). CD4+ T cells, CD4+CD25+ T cells, and DC magnetic bead isolation kits were obtained from Miltenyi Biotec.

GM-CSF treatment: NOD mice were given i.p. injections of GM-CSF (2-3 ug/mouse/day) for 5 consecutive days at the indicated weeks of treatment. Time course of GM-CSF injections included treatments at weeks 7, 9, 11, 13, 15, and 19. Blood glucose levels were monitored weekly for hyperglycemia by using an Accu-Chek complete glucometer by tail vein incision. Mice were considered diabetic if glucose concentration was maintained >250 mg/dl for two consecutive weeks. Efficacy of treatment was determined by comparing age matched untreated NOD mice to the treated groups for disease development.

DC and T cell Isolation: Single cell suspensions were prepared from the spleens and LNs of both GM-CSF treated and untreated female NOD mice. For CD4+CD25+ isolation, CD4+ T cells were first negatively selected using magnetic bead separation) and CD25+ T cells were then isolated using positive selection on magnetic beads (Miltenyi Biotec) according to the manufacturer's instructions. 90% pure CD4+ CD25+ T cells was obtained. For CD11c DC isolation, cell suspensions were positively selected using magnetic bead separation as well (Miltenyi Biotec) according to Milteneyi's instructions. DC purity was about 85% pure.

Analysis of DC maturation: Mice from both treated and age matched control groups were sacrificed after treatment at weeks 9, 13, 15, and 19. Sacrifice of mice occurred 48 h after last treatment of the indicated weeks. Spleen cells from these mice were stained with FITC-conjugated ant-mouse CD11c in combination with PE-conjugated anti-mounse B7.1, B7.2, CD40, CD8a, or MHC class II and analyzed in a FACS analyzer (BD Biosciences). DCs were isolated from splenocytes using a CD11c isolation kit (Miltenyi Biotec), and RNA was extracted using trizol followed by mRNA isolation using a mRNA isolation kit (Miltenyi Biotec). cDNA were further synthesized and used for PCR. Sepsis Cytokine (IL-10, IL-6, TNF-a, IL-1, and IL-12) transcript levels were determined using a multiplex PCR system according to the manufacturer's guidelines (Maxim Biotec).

Adoptive Transfer studies: To determine Treg efficacy, splenocytes ($5\times10^6$) from recently diabetic mice were adoptively transferred either alone or with purified CD4+CD25+ T cells ($1\times10^6$) from GM-CSF treated or untreated mice into 6 week old female NOD scid mice (n=5). Blood glucose was measured weekly and diabetes onset was determined.

For DC's role in regulatory T cell activation either 5 wk old NOD scid mice were treated with GM-CSF (3 ug/100 ul) or left them untreated (n=5/group) and then adoptively transferred either naïve CD4+ T cells or naïve CD4+CD25− T cells from wild type female NOD mice. Blood glucose levels were monitored weekly and diabetes onset was determined as herein.

For further verification of the mechanism CD11c+ DC's ($1.5\times10^6$) from either treated or untreated wt female NOD mice were isolated and adoptively transferred them into 8 wk old naïve wt female NOD mice recipients (n=8). In five of the mice, disease was monitored as above. In the other three, Foxp3 expression was determined 1 wk post transfer by intracellular FACS analysis.

Measurement of cytokine production: Splenocytes ($2.5\times10^6$ cells/well) were incubated in the presence or absence of plate bound anti-CD3 (5 ug/mL) in 1 mL of RPMI 1640 supplemented medium supplemented with 2% normal mouse serum for 36 h. Cell free culture supernatant were assayed by ELISA, using paired Abs to detect Th1/Th2 cytokine levels following the manufactur's instructions (eBioscience), and the $OD_{450}$ was recorded using a Microplate reader (Bio-Rad). Cytokine measurements were determined using corresponding cytokine standards provided by the kit. The suggested lowest detection levels using this kit are 2 pg/ml for IL-2, 4 pg/ml for IL-4, 15 pg/ml for IFN-γ, and 15 pg/ml for IL-10.

H & E and Immunohistochemistry: Pancreata were removed and fixed in formalin, embedded in paraffin, sectioned, and stained with H&E. Sections were scored for mononuclear cell infiltration as follows: grade 0=normal islets; grade 1=focal or peripheral insulitis (localization of lymphocytes around or surrounding the islet, but no destruction of endocrine cells); and grade 2=invasive destructive insulitis.

Statistical analysis: Mean, SD, and statistical significance were calculated using an SPSS application. Statistical significance was determined using the nonparametric Wilcoxon signed test. In most cases, values of individual treated groups were compared with those of untreated groups. A value of p≦0.05 was considered significant.

Materials and Methods

Figure 13:
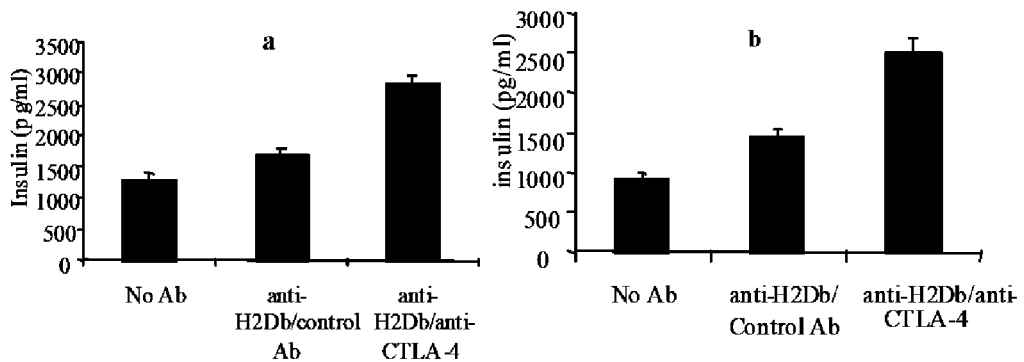
FIG. 13 illustrates inhibition of in vitro alloresponse; CBA/J ($H2^k$) mice were immunized with NIT-1 cells on day 0 and day 10; spleen cells collected from naïve (a) or immune mice (b) on day 20 were stimulated in triplicate with NIT-1 cells in the presence or absence of antibodies for 48 hrs and the spent medium was replaced with fresh medium and incubated for another 48 hrs; supernatants collected from this culture were tested for insulin production by ELISA.

Modulation of immune response to insulin producing cells: The insulin secreting cell line NIT-1 was used as an in vitro surrogate for allogeneic beta cells. A BiAb reagent was prepared that would bind to the H-2$^b$ NIT-1 cell by linking an anti-H2-D$^b$ antibody to the anti-CTLA-4 antibody. Spleen cells from naive or NIT-1 cell primed CBA/j mice (H2-K$^k$) were incubated with NIT-1 cells in the presence of the BiAb and tested for T cell proliferation, and for the ability of NIT cells to produce insulin. The BiAb suppressed the T cell response against NIT-1 cells significantly compared to control antibody. Further, NIT-1 cells incubated with BiAb and primed spleen cells continued to produce insulin indicating that these cells were spared from killing by the allo-reactive T cells (FIG. 13).

In vitro allo-islet protection assays: Balb/c (H2Kd) mice are used as islet donors and C57BL/6 (H2Kb) as the recipient to test an anti-H2-Kd/anti-CTLA-4 BiAb in protecting against immune attack from C57BL/6 (H2-Kb) mice. Pancreatic islets have been routinely isolated from Balb/c mice (H2-d) by collagenase treatment followed by percoll gradient centrifugation. Pancreatic islets from Balb/c mice were isolated by collagenase digestion followed by percoll density gradient centrifugation. Islets during collagenase digestion, purified islets, and islet free fraction were treated with an islet specific stain (dithiazone). These islets have been used in in vitro and in vivo assays to test for the ability of an anti-H2-Kd/anti-CTLA-4 BiAb to protect against immune attack from C57BL/6 (H2-b) mice.

Figure 14:
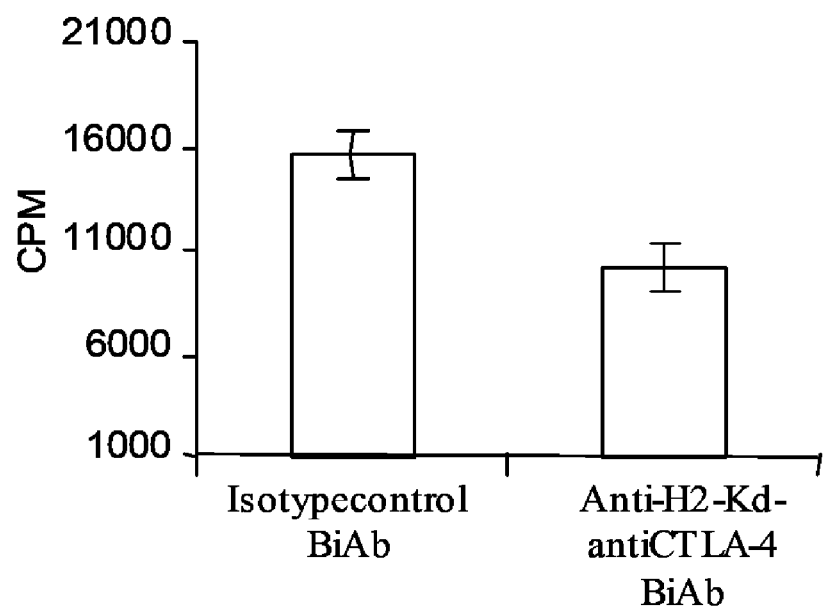
FIG. 14 shows in vitro inhibition of alloresponse to islets; islets were isolated from Balb/c mice and used as single cell suspension prepared by trypsin digestion. Islet cells were coated with either isotype control BiAb or anti-H2-Kd-anti-CTLA-4 BiAb and incubated with spleen cells from mice that were pre-immunized with H2Kd alloantigen; T cell proliferation response was measured by the 3H-thymidine incorporation method.
Figure 15:
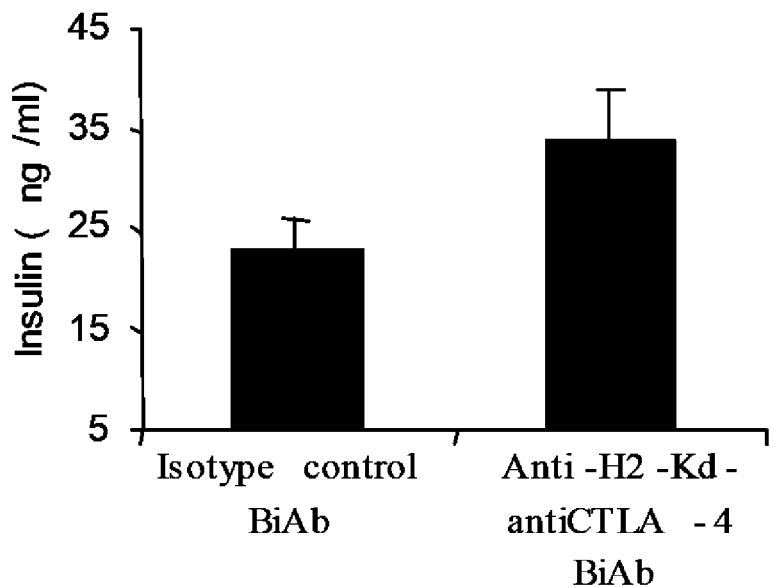
FIG. 15 shows an in vitro insulin production assay; islets were isolated from Balb/c mice and used as single cell suspension prepared by trypsin digestion; islet cells were coated with either isotype control BiAb or anti-H2Kd-anti-CTLA-4 BiAb and incubated with spleen cells from mice that are immune to H2-Kd alloantigen; supernatant from all the cultures were discarded after three days and fresh medium was added; spent medium from days 3-5 cultures were collected and tested for insulin levels using an ELISA kit for murine insulin.

Initially, an anti-H2-Kd antibody was linked to the anti-CTLA-4 antibody to produce an anti-H2-Kd/anti-CTLA-4 BiAb. The potential of the anti-H2-Kd/anti-CTLA-4 BiAb to protect H2-Kd islets in vitro from allo-reactive T cells was determined. Anti-H2Kd antibody linked to hamster IgG was used as an isotype control BiAb. Spleen cells from either naive or H2d (M12 cell) primed C57BL/6 (H2-Kb) mice were incubated with trypsin digested single islet cell suspension from Balb/c mice in the presence of either the BiAb or the isotype control BiAb. Subsequently, T cell proliferation was tested as an indicator of the alloresponse and for the ability of the islet cells to produce insulin as an indicator of islet cell survival. As shown in FIG. 14, BiAb suppressed the T cell proliferation response against the islets significantly compared to the control BiAb. If the alloresponse is suppressed then one would expect islets to survive longer and continue to produce insulin. As expected, islets from BlAb treated cultures produced higher amounts of insulin relative to cultures treated with a control BiAb (FIG. 15).

To test for the efficiency of the transplantation procedure pancreatic islets were isolated from Balb/c (H2-Kd) mice and transplanted (200 islets/mouse) into either syngeneic (Balb/c) or allogeneic (C57BL/6-H2$^b$) mice under the right kidney capsule. These mice had been rendered diabetic by pre-treatment with streptozotocin (200 mg/kg). Recipients were monitored for 20 days for blood glucose levels. Islet transplantation in allogeneic and syngeneic mice were performed. Islets were isolated from Balb/c mice and about 200 islets were transplanted under the right kidney capsule of each Balb/c (syngeneic) or C57BL/6 (allogeneic) mice that were treated with streptozotocin intraperitoneally (200 mg/kg) to induce diabetes; these mice were monitored for glucose levels for 20 days. Mice that received syngeneic islets showed normal glucose levels within 7 days of transplantation. However, mice that received allogeneic islets failed to show normal glucose levels, suggesting graft rejection due to alloresponses. To see whether islet cells are coated with the Bi Ab which protects them, islets from Balb/c (H2-Kd) mice with BiAbs, washed and transplanted them into streptozotocin pre-treated C57BL/6 (H2-Kb) diabetic mice. Islet transplantation in allogeneic and syngeneic mice were performed. Islets were isolated from Balb/c mice and coated with either isotype control BiAb or anti-H2Kd-anti-CTLA-4 BiAb and about 200 islets were transplanted under the right kidney capsule of each C57BL/6 (allogeneic) mice that were treated with streptozotocin intraperitoneally (200 mg/Kg) to induce diabetes. These mice were monitored for glucose levels for 20 days and this experiment was repeated twice with similar results. Glucose levels of recipients were monitored for the next 20 days. Although there was a reduction in glucose levels in mice that received anti-H2-Kd/anti-CTLA-4 BiAb coated islets compared to mice that received isotype control BiAb coated islets, they failed to reach normal glucose levels.

Mice. 6-8 week-old female CBA/J were purchased from The Jackson Laboratory (Bar Harbor, Me.). Mice were housed in the Biological Resources laboratory facility at the University of Illinois (Chicago, Ill.) and provided food and water ad libitum. Animals were cared for in accordance with the guidelines set forth by the University of Illinois Animal Care and Use Committee. All mice were used at 8-10 weeks of age.

GM-CSF, Abs and mouse thyroglobulin. Recombinant mouse GM-CSF was purchased from Cell Sciences (Cell Sciences, Canton, Ma.). FITC-conjugated anti-CD11c and PE-conjugated anti-I-Ak (MHC class II), anti-CD8a, anti-CD80, anti-CD86, and anti-CD40 (BD PharMingen, San Diego, Calif.); PE-conjugated anti- CD4, anti-CD8a, and anti-CD25 (Caltag Laboratories, Burlingame, Calif.) Abs were used in flow cytometry. Neutralizing rat monoclonal Ab to mouse IL-10 receptor (clone 1B1.3a) was provided by Kevin Moore (DNAX, Palo Alta, Calif.). Purified rat IgG was used for isotype control (Fitzgerald, Concord, Mass.). T cells, CD4+CD25+ T cells, and dendritic cell magnetic bead isolation kits were obtained from Miltenyi Biotec (Auburn, Calif.). Normal mouse thyroids obtained from BiochemMed and thyroglobulin was prepared (Winchester, Va.).

GM-CSF treatment and Immunization with thyroglobulin. Three groups of mice (viz, 1, CFA control; 2, mTg control; 3, GM-CSF/mTg) were used unless specified. Mice in groups 1 and 2 were injected with PBS and mice in group 3 were injected with 2 μg of GM-CSF/mouse/day from days 1-5 and 15-19. Mice in groups 2 and 3 were immunized s.c. with mTg (100 μg/mouse) emulsified in Complete Freund's Adjuvant (CFA) on days 6 and 20. Mice in group 1 (CFA control) received PBS emulsified in CFA on days 6 and 20. Mice from these three groups were sacrificed at different time points for different experiments as described below to understand the various aspects of GM-CSF mediated immunomodulation.

Effects of GM-CSF treatment on DC maturations Above mentioned mouse groups 2 and 3 (i.e. mTg control and GM-CSF/mTg respectively) were used. Animals were sacrificed before (days 6 and 20) and after (days 8 and 22) each mTg immunization. The immunization schedule was staggered in such a way that all animals were sacrificed at the same time. Spleen cells from these mice were stained with FITC conjugated anti-mouse CD11c in combination with PE conjugated anti-mouse MHC class II, B7.1, B7.2, or CD40 antibodies and analyzed in a FACS analyzer (Becton Dickinson, Franklin Lakes, N.J.). DCs were isolated from splenocytes using a CD11c isolation kit and mRNA was extracted using an mRNA isolation kit (Miltenyi Biotech, San Francisco, Calif.). All procedures were carried out according to manufacturer's instructions. The cDNAs were synthesized from mRNA samples and used for PCR. Cytokine transcript levels for IL-10, IL-6, TNF-α, IL-1, and IL-12 were determined using multiplex PCR method according to manufacturer's guidelines (Maxim Biotech Inc.).

Adoptive transfer of CD4$^+$CD25$^+$ T cells. CFA control, mTg control, GM-CSF/mTg and a CD4$^+$CD25$^+$ T cell recipient groups were included in this experiment. Mice from GM-CSF/mTg group were used as donors and were sacrificed on day 34 and CD4$^+$CD25$^+$ T cells were isolated from splenocytes and lymph nodes using a CD4$^+$CD25$^+$ isolation kit following manufacturer's instructions (Miltenyi Biotech). Isolated population was >90% pure. One set of mTg immunized mice was adoptively transferred with donor CD4$^+$CD25$^+$ T cells (1×10$^6$/mouse) by i.v. injection on day 28 post-initiation of immunization. Animals were sacrificed on day 45 (day 18 post-transfer) and lymph nodes, spleens, thyroids, and sera were collected for analyzing mTg specific immune response.

CD4$^+$CD25$^+$ T cell Co-culture. mTg control and GM-CSF mTg mouse groups were used. Mice were treated with GM-CSF and immunized with mTg as described herein. They were sacrificed on day 35, spleen and lymph node cells were collected, and CD4$^+$CD25$^+$ T cell were isolated from mice in GM-CSF/mTg group as described above. Effector T cells were isolated from spleen and lymph node cells from mice in mTg control group using magnetic cell sorting (Miltenyi Biotech) and stained with CFSE at a concentration of 1 µM for 10 min at 37° C. Cells were washed 3× and plated into 96-well flat bottom plates at 0.5×10$^6$ cells/well. Isolated CD4$^+$CD25$^+$ T cells from group 3 were added to cultures at a 5:1 effector:Treg ratio. T cell depleted spleen cells (0.5×10$^6$ cells/well) or enriched dendritic cells (0.5×10$^6$ cells/well) from naïve mice (both accomplished by magnetic cell sorting) (Miltenyi Biotech) were used as feeder cells. Cells were harvested after 7 days in culture and tested for CFSE dilution using a FACS analyzer (BD Bioscience, San Jose, Calif.).

αIL-10R antibody treatment. Six groups (viz, 1, CFA control; 2, mTg control; 3, GM-CSF/isotype control; 4, GM-CSF/αIL-10R #1; 5, GM-CSF/αIL-10R #2; 6, GM-CSF/αIL-10R #3) were included in this set of experiments, with 4-5 mice per group. Groups 1, 2, and 3 correspond with those mentioned above with the exception that animals in group 3 received i.p. injections of rat IgG isotype control antibody (0.5 mg/mouse) on days 6, 11, 20, 25 and 32. Animals in group 4, 5 and 6 were treated with GM-CSF and immunized with mTg as described above and received i.p. injections of αIL-10R (0.5 mg/mouse) on days 6, 11, 20, 25, and 32; 6 and 20; and 11, 25 and 32 respectively. All animals were sacrificed on day 45 and lymph nodes, spleen, thyroids, and serum were collected to evaluate thyroiditis.

Effects of GM-CSF treatment on thyroid microenvironment CFA control, mTg control, and GM-CSF/mTg mice were used. Three mice from each group were sacrificed on day 21, thyroids were collected, pooled within groups, and digested with collagenase D (0.5 mg/ml) for 1 h at 37° C. to prepare single cell suspension. Cells were washed with PBS supplemented with 2% FBS, blocked with anti-CD16/CD32 Fc-Block (BD PharMingen) on ice for 30 min. Cells were stained with FITC-conjugated anti-mouse CD4 along with PE-conjugated anti-mouse CD25 mAbs on ice for 15 min, washed, and analyzed using a FACS analyzer (BD Biosciences) and the CellQuest software. At least 10,000 cells per sample were analyzed. To determine cytokine/chemokine production, thyroid cell suspensions were maintained in RPMI-1640 media containing 2% normal mouse serum for 36 h. Cell free supernatants were collected from these cultures and spontaneous cytokine (IL-4, IL-10, and IFN-α) and chemokine production (MCP-1 and RANTES) were detected by a multiplex cytokine/chemokine assay kit using Luminex technology at the Luminex core facility of University of Pittsburgh Cancer Center, Pittsburgh. The suggested lowest detection levels using this kit are 5 pg/ml for IL-4, 1 pg/ml for IFN-α, 15 pg/ml for IL-10, 5 pg/ml for MCP-1, and 5 pg/ml for RANTES.

To assess apoptotic molecule expression on thyrocytes, thyrocytes were separated from other resident cells and mRNA was isolated using an mRNA isolation kit following manufacturer's instructions (Miltenyi Bitoech). RT-PCR was carried out using mRNA and gene specific primers for Fas, FasL, caspase-8 (Maxim Biotech Inc.). α-actin was used as a control to ensure equivalent amounts of RNA in the assay.

mTg specific T cellproliferation. Mouse splenocytes or lymph node cells (5×10$^5$ cells/well) were plated in 96-well flat-bottom tissue culture plates in triplicate in RPMI 1640 containing 2% normal mouse serum at a final volume of 0.25 ml/well. mTg was added at a concentration of 20 µg/ml. Con A (1 µg/ml) was used as a positive control. Cells were incubated for 72 hat 37° C. in a $CO_2$ incubator. Cells were pulsed with 1 µCi [$^3$H] thymidine/well for the last 16 hours of culture, transferred into 96-well U-bottom tissue culture plates, washed 2× with PBS, lysed in water and dried overnight at 37° C. Scintillation fluid was added to these wells (50 µl well) and counted using a 96-well plate Microbeta counter (PerkinElmer Wallac, Gaithersburg, Md.). To evaluate and to test the T cell pattern of proliferation, cells were stained with CFSE as described above, plated in 96-well flat-bottom tissue culture plates in the presence or absence of mTg (20 µg/ml) in RPMI 1640 containing 2% normal mouse serum at a final volume of 0.25 ml/well, maintained for 7 days, harvested and tested for CFSE dilution using FACS (BD Bioscience).

Measurement of cytokine production. Spleen or lymph node 5×10$^6$ cells/well (12-well plate) were incubated in the presence or absence of mTg (20 µg/ml) in 1.5 ml of PRMI 1640 medium supplemented with 2% normal mouse serum for 36 h. Cell-free culture supernatants were collected after 36 h by centrifugation. Cytokine levels in cell-free supernatants were assayed by ELISA using paired Abs for detection of IL-2, IL-10, IL-4, and IFN-α, following manufacturer's instructions (eBioscience, San Diego, Calif.) and the $OD_{450}$ was recorded using a Microplate reader (Bio-Rad, Hercules, Calif.). The amount of cytokine was determined using corresponding cytokine standards. The suggested lowest detection levels using this kit are 2 pg/ml for IL-2, 4 pg/ml for IL-4, 15 pg/ml for IFN-α, and 15 pg/ml for IL-10.

Evaluation of EAT Thyroids collected from mice at the time of sacrifice were fixed in formalin, embedded in paraffin, sectioned, and stained with H&E. Thyroids were scored for the extent of thyroid lymphocytic infiltration, as a marker of disease severity, using a scale of 1+ to 5+. An infiltrate of at least 125 cells in one or several foci was scored 1+; Ten to twenty foci of cellular infiltration involving up to 25% of the gland was scored 2+; An infiltration involving up to 25-50% of the gland was scored 3+: Destruction of greater than 50% of the gland was scored 4+, and near complete destruction of the gland with few or no remaining follicles was scored 5+.

Statistical analysis. Mean, SD, and statistical significance were calculated using an SPSS application. Statistical significance was determined using the nonparametric Wilcoxon signed test. In most cases, values of individual-treated and immunized groups were compared with that of untreated but immunized group. A p value of <0.05 was considered significant. Mean, SD, and statistical significance (value) were calculated using SSPS statistical application (SSPS, Chicago, Ill.). Thep value was determined using the nonparametric Wilcoxon signed test. In most cases, values of BiAb-treated group (mice that received anti-CTLA-4 Ab-coated mM12 cells) were compared with that of mM12 immune group (mice that received isotype control Ab-coated mM12 cells) unless specified. Differences in the percentage of fluorescence-positive cells between test and control groups were tested using the nonparametric sign test. A p value of ≦0.05 was considered significant.

Mouse strains: Six-week-old female CBA/J, BALB/c, and C57BL/6 mice were purchased from The Jackson Laboratory (Bar Harbor, Me.). Mice were housed in the biological resources laboratory at the University of Illinois at Chicago and allowed food and water ad libitum. All mice were used at 8 wk of age and cared for in accordance with the guidelines set forth by the Animal Care and Use Committee at University of Illinois at Chicago.

Abs and cell lines: M12, a B cell lymphoma of BALB/c origin (H-$2^d$), M12 cells stably transfected with the murine TSHR cDNA (mM12 cells), and Ag/8 mouse B cell lymphoma (H-$2^d$) were used. Hamster anti-mouse CTLA-4 hybridoma (UCI0-4-F-I0-11; American Type Culture Collection, Manassas, Va.) and mouse anti-mouse TSHR hybridoma (D6-4), were grown in DMEM/F12 medium supplemented with L-glutamine (2 mM), HEPES (15 mM), sodium pyruvate (1 mM), 2-ME ($5 \times 10^{-5}$ M), penicillin (100 U/ml), streptomycin (0.1 mg/ml), fungizone (1 µg/ml), and 10% FBS. The D6-4 hybridoma was prepared by fusing spleen cells from BALB/c mice with autoimmune Grave's disease and the mouse B cell myeloma Sp2/0. Abs were purified from the spent medium using Protein L (Sigma-Aldrich, St. Louis, Mo.) affinity columns, concentrated, and dialyzed against PBS (0.01 M; pH 7.2). These Abs were digested with pepsin and the F(ab)$_2$ fragments were purified by gel filtration chromatography. Anti-CTLA-4-anti-TSHR BiAb was prepared by SPDP (N-succinimidyl-3-(2-pyridyldithiol)propionate)-SMPB (succinimidyl-4-(p-maleimidophenyl)butyrate) chemical coupling. The coupled Abs were then purified from unlinked Abs by passing first through anti-mouse IgG-Sepharose and followed by anti-hamster IgG-Sepharose affinity columns. The purified Ab was labeled as test BiAb (tBiAb). Purified hamster IgG was purchased from Fitzgerald International (Concord, Mass.), and the F(ab) fragment was prepared and used to prepare control BiAb (cBiAb) by linking to the anti-TSHR F(ab)$_2$ fragment. Coupling and target binding efficiencies of all preparations were tested.

Anti-CD16/CD32 Ab; FITC-conjugated anti-mouse CD3, CD4, and CD8a; and PE-labeled anti-mouse CD4, CD8, CD25, CTLA-4, CD62L, CD69, IL-2, IL-4, IL-10, IFN-γ, and TGF-β1 (Caltag Laboratories, San Francisco, Calif., and BD Pharmingen, San Diego, Calif.) were used in flow cytometry. Paired Abs and required cytokine standards for detecting mouse IL-2, IL-4, and IFN-γ (Caltag Laboratories) and for detecting IL-10 and TGF-β1 (BD Pharmingen) were used in ELISA. Neutralizing Abs to mouse IL-4 (rat IgG1; clone 11B11) and IL-10 (rat IgG1; clone JES5-2A5) were purchased from eBioscience (San Diego, Calif.). Recombinant mouse IL-2 (rmIL-2), neutralizing Ab to mouse TGF-β1 (rat IgG1; clone 1D11), and normal rat IgG1 isotype control were purchased from R&D Systems (Minneapolis, Minn.); magnetic bead-conjugated, anti-PE, anti-mouse CD4, CD62L Abs, pan T cell isolation kit, CD4$^+$CD25$^+$ T cell isolation kits (Miltenyi Biotec, Auburn, Calif.) were used to isolate CD3$^+$, CD4$^+$, CD4$^+$CD25$^+$, CD4$^+$CD25$^+$CD62L$^+$, and CD4$^+$CD25$^+$ CD62L$^-$ cells. The Fab of anti-CTLA-4 was prepared by papain digestion using papain-linked agarose beads (Pierce, Rockford, Ill.) according to the manufacturer's instructions.

Tolerance induction by CTLA-4 engagement. mM12 cells were treated with mitomycin C (50 µg/$10^7$ cells/ml), and $1 \times 10^7$ cells were incubated with either cBiAb or tBiAb (100 µg) for 30 min on ice. Eight-week-old female CBA/J mice (H-$2^k$) were then injected with these cells i.p. twice at 10-day interval (on day 0 and 10). Although control mice (mM12 immune group) received mM12 cells coated with cBiAb prepared from control Abs (anti-TSHR anti-hamster IgG BiAb), test mice (BiAb-treated group) received mM12 cells coated with tBiAb prepared by linking anti-CTLA-4 and anti-TSHR Abs unless specified. Hereafter, mice that received cBiAb-coated mM12 cells and tBiAb-coated are referred as control group and BiAb-treated group, respectively. Mice were sacrificed 10 days after the booster injection (day 20), and lymphocytes were collected from spleens and lymph nodes. For some studies, tolerized mice were rechallenged with M12 cells on day 60 and sacrificed on day 70.

Immunization/challenge with alloantigens. Mice were tolerized by CTLA-4 engagement as described above. On day 20, these mice were immunized (i.p.) with mitomycin C-treated spleen cells ($1 \times 10^7$ cells/mouse) from C57BL/6 (H$2^b$) or BALB/c (H$2^d$) mice, or Ag8 (H$2^d$) cells ($2 \times 10^6$ cells/mouse). These mice were sacrificed on day 30 and tested for their ability to respond to M12 and other alloantigens by lymphocyte proliferation and IL-2 production assays.

Proliferation assay. Effector cells (spleen cells or purified T cell populations; $0.5 \times 10^6$ cells) and mitomycin C-treated target cells (M12 cells, $0.5 \times 10^5$ cells/well; spleen cells, $5 \times 10^5$) were plated in 96-well flat-bottom tissue culture plates in triplicate in RPMI 1640 containing 2% normal mouse serum at a final volume of 0.25 ml well. In some experiments, the assay was conducted in the presence of varying concentrations (5-200 U/ml) of rmIL-2. After 48 h, cells were pulsed with 1 µCi/well [$^3$H]thymidine for 18 h in 100 µl of the above medium supplemented with 2% normal mouse serum. Cells were harvested, and [$^3$H]thymidine incorporation was measured using Microbeta scintillation counter (PerkinElmer Wallac, Gaithersburg, Md.). Background counts of effector cell cultures containing no M12 cells were subtracted from test values to calculate the actual counts.

CFSE staining. Single-cell suspensions of splenic or purified lymphocytes from either immune or tolerant mice were suspended in HBSS at a concentration of $1 \times 10^6$ cells/ml and labeled with the tracking fluorochrome CFSE (Molecular Probes, Eugene, Oreg.). Cells were incubated with CFSE at a final concentration of 1 µM in HBSS for 5 min, and labeling was terminated by the addition of FCS (10% of the total volume). Cells were washed twice in complete RPMI 1640 medium and used in proliferation assays as described above. The dilution of CFSE was measured by flow-cytometric analysis after 7 days of incubation.

Flow cytometry. Single-cell suspensions of spleen and lymph nodes were washed with PBS supplemented with 2% FBS (pH 7.4) and blocked with anti-CD16/CD32 Fc block on ice for 15 min. Cells were stained with FITC-, PE-, and cytochrome-labeled appropriate Abs in various combinations on ice for 30 min, washed, and analyzed in a FACS analyzer (BD Biosciences, San Jose, Calif.), and the data were analyzed using the CellQuest or WinMDI software. Control cells were stained with isotype-matched control Abs and analyzed. At least 10,000 cells were analyzed in all experiments.

Cytokine production. A total of $5 \times 10^6$ spleen cells/well (12-well plate) was incubated in the presence of $0.5 \times 10^6$ mitomycin C-treated target M12 cells in 1.5 ml of RPMI 1640 medium supplemented with 2% normal mouse serum for 48 h. Cell-free culture supernatants (spentmedium) were collected after 48 h, and the cytokine levels were assayed by ELISA using paired Abs and respective cytokine standards for the detection of IL-2, IL-4, IL-10, IFN-γ, and TGF-β1 according to the manufacturer's directions. Cytokines were detected by adding HRP-labeled streptavidin followed by washing and addition of tetramethyl benzidine-$H_2O_2$ substrate (BD Pharmingen) for 5-10 min. The OD$_{450}$ was read using a Microplate reader (Bio-Rad Laboratories, Hercules, Calif.). The amount of cytokine was determined using an appropriate cytokine-specific standard curve. Background cytokine levels of effector cell cultures containing no M12 cells were subtracted from test values to calculate the actual cytokine response.

For intracellular cytokine expression analysis, spleen cells collected at the end of the experiment were either activated with mitomycin C-treated M12 cells or allowed to rest for 36 h. Cells were stained with FITC-conjugated Ab to CD3 and were then fixed and permeabilized using Cytofix/perm reagent (BD Pharmingen). Subsequently, these cells were stained with PE-labeled specific anti-cytokine Abs, washed, and analyzed in a FACS analyzer as described above. In some experiments, cytokines were detected by multipex cytokine assay using Luminex (Austin, Tex.) technology at the Luminex core facility of University of Pittsburgh Cancer Center (Pittsburgh, Pa.).

Cytokine neutralization and CTLA-4 blockade assays. T cells were cultured in the presence of mitomycin C-treated M12 cells as described above for CFSE dilution assay. To these cultures, varying concentrations of neutralizing anti-mouse IL-4 (10-2000 ng/ml), anti-mouse IL-10 (10-5000 ng/ml), anti-mouse TGF-β1 (10-2000 ng/ml), and/or isotype-matched control Abs were added and incubated for 7 days. Varying concentrations (100 ng to 10 μg/ml) of Fab of anti-mouse CTLA-4 or isotype control Ab were added to some cultures to block CTLA-4 interactions. The dilution of CFSE was measured by flow-cytometric analysis after 7 days of incubation.

Isolation of $CD4^+CD25^+$ T cells and other T cell subpopulations. $CD4^+CD25^+$ cells were isolated using Abs conjugated to magnetic beads and magnetic separation column according to manufacturer's directions. Pooled mouse spleen and lymph node cells were incubated with anti-CD16/32 Ab for 15 min on ice to block FcRs, and subsequently, $CD3^+$ T cells were isolated using a pan T cell isolation (negative selection) kit by following manufacturer's instructions. $CD4^+CD25^+$ T cells were isolated from spleen cells or the $CD3^+$ population using either PE-labeled anti-mouse CD25 and magnetic bead-labeled anti-PE Abs, or a CD4+CD25+ T cell isolation kit. Cells were incubated with PE-labeled anti-mouse CD25 Ab for 30 min on ice. Cells were then incubated with magnetic bead-conjugated anti-PE Ab for 15 min on ice, washed, and sorted using LS magnetic columns or an automated machine (Automacs; Miltenyi Biotec). Isolated cells were washed and stained with FITC- or PE-labeled appropriate Abs, and tested for purity in a flow cytometer (FACS-Calibur; BD Biosciences). For some experiments, $CD4^+CD25^+$ cells were enriched for $CD62L^+$ and $CD62L^-$ populations using magnetic separation procedures. For this, $CD3^+$ cells were isolated using the pan T cell isolation kit, and $CD62L^+$ and $CD62L^-$ cells were enriched using magnetic bead-labeled anti-mouse CD62L Ab. $CD25^+$ cells from $CD62L^-$ fraction were enriched as described above. $CD62L^+$ T cells were washed using acidified PBS to remove bound beads, and the $CD25^+$ population was enriched.

Cocultivation of $CD25^+$ and $CD25^-$ T cells. $CD4^+CD25^-$ cells from control mice (mM12 immune) were mixed with $CD4^+CD25^+$ cells from tolerant mice and vice versa at a ratio of 10:1. In some assays, $CD4^+CD25^+CD62L^+$ or $CD4^+CD25^+CD62L^-$ enriched populations were used instead of $CD4^+CD25^+$ cells. These mixtures at various ratios or individual cell populations were used in T cell proliferation assays (total of $0.6×10^5$ cells/well) that were conducted either in the presence or absence of M12 cells, as described above.

Transwell T cell inhibition assays. $CD4^+CD25^+$ cells from tolerant mice were isolated as described above. $CD4^+CD25^+$ cells ($2.5×10^5$) plus mitomycin C-treated M12 cells ($0.5×10^5$) in the well insert (upper compartment) and $CD25^-$ T cells plus M12 cells ($2.5×10^6$) in the well (lower compartment) were cultured in a Transwell assay system using Falcon Transwell tissue culture well inserts (BD Biosciences) in a 24-well plate format. After 48 h, cells were pulsed with 2.5 μCi of [$^3$H]thymidine for 18 h. Cells from the upper and lower compartments were pooled, and proliferation was measured as [$^3$H]thymidine incorporation in a scintillation counter.

Adoptive transfer of Treg cells. $CD4^+CD25^+$ T cells were isolated from both control and test mice (CBA/J; $H2^k$) as described above. Recipient mice were immunized with M12 cells ($H2^d$) on day 0 and C57BL/6 spleen cells ($H2^b$) on day 10. Approximately $5×10^6$ $CD4^+CD25^+$ T cells were adoptively transferred (i.v.) to recipient mice on day 20, 2 h before challenge injection with M12 cells. These mice were sacrificed on day 30 post transfer, and tested for T cell-proliferative and IL-2 responses to M12 cells and C57BL/6 spleen cells as described above.

DOCUMENTS

The following documents, to the extent they relate materials and methods used in this disclosure, are incorporated by reference herein.

Adorini et al., 2003. *J. Cell Biochem.* 88:227.
Aruna et al., 2005. Proc. Natl. Acad. Sci. USA 102: 10285-10290.
Asano et al., 1996. *J Exp Med.* 184:387.
Brocke et al., 1988. J. Clin. Invest. 82: 1894-1900.
Batteux et al., 1999. *Eur J Immunol.* 29:958.
Cristadoss et al., 2000. Clin. Immunol. 2: 75-87.
Dieckmann et al., 2002. *J. Exp. Med.* 196;247.
Dogan et al., 2003. J. Immunol. 170: 2195-2204.
Drachman, D. B. 1994. N. Engl. J. Med. 330: 1797-1810.
Duan et al., 2004. Neurobiol. Dis. 16: 461-467.
Gad et al., 2003. *APMIS.* 111:766.
Goulvestre et al., 2002. *Eur J Immunol.* 32:3435.
Groux, H., and F. Cottrez. 2003. *J Autoimmun.* 20:281.
Groux, H., N. Fournier, and F. Cottrez. 2004. *Semin Immunol.* 16:99.
Hackstein et al., 2001. Trends Immunol. 22: 437-442.
Hamilton et al., 1991. *Clin Exp Immunol.* 83:64.
Hara et al., 2001. *J Immunol.* 166:3789.
Horwitz et al., 2003. *J Leukoc Biol.* 74:471.
Jonuleit et al., 2001. *Trends Immunol.* 22:394.
Jonuleit et al., 2002. *J. Exp. Med.* 196:255.
Karachunski et al., 2000. J. Immunol. 164: 5236-5244.
Kingsley et al., 2002. *J Immunol.* 168:1080.
Kuwana, M. 2002. *Hum Immunol.* 63:1156.
Levings et al., 2002. *Int Arch Allergy Immunol.* 129:263.
Levings, M. K., and M. G. Roncarolo. 2000. *Allergy Clin. Immunol.* 106:S109.
Li et al., 2005. J. Huazhong Univ. Sci. Technolog. Med. Sci. 25: 215-218.
Lutz et al., 2000. *Eur. J. Immuno.* 30:1813.
Lutz, M. B., and G. Schuler. 2002. *Trends Immunol.* 23:445.
Mahnke et al., 2003. Blood. 101:4862.
Maldonado-Lopez et al., 1999. *J Leukoc Biol.* 66:242.
Maldonado-Lopez et al., 2001. *J Immunol* 167:4345.
Maldonado-Lopez, et al., 1999. *J Exp Med.* 189:587.
Maraskovsky et al., 1997. Adv. Exp. Med. Biol. 417: 33-40.
McKenna et al., 2000. Immunol. Today 21: 19-23.
Menges et al., 2002. *J Exp Med.* 195:15.
Mignon-Godefroy et al, 1995. *J Immunol.* 154:6634.
Min et al., 2003. *J. Immunol.* 170:1304.
Montani et al., 1998. *Endocrinology.* 139:290.
Morel et al., 2003. *Clin Exp Immunol.* 133:1.
Morelli, A. E., and A. W. Thomson. 2003. *Immunol Rev.* 196:125.
Morris et al., 2003. Cell Immunol; 226:20.
Moser, M. 2003. *Immunit.* 19:5.
Nagane et al., 2003. Muscle Nerve 27: 582-589.

O'Garra, A., and P. Vieira. 2004. *Nat Med.* 10:801.
O'Keefe et al., 2002. Blood 99: 2122-2130.
Piccirillo, C. A., and A. M. Thornton. 2004. *Trends Immunol.* 25:374.
Pinkoski, M. J., and D. R. Green. 2000. *Nat Immunol.* 1:461.
Pujol-Borrell et al., 1986. *Mol Biol Med.* 3:159.
Roncarolo et al., 2001. *Immunol Rev.* 182:68.
Rossi & Young. 2005. J. Immunol. 175: 13 73 -1381.
Rutella, S., and R. M. Lemoli. 2004. *Immunol Lett.* 94:11.
Shevach, E. M. 2000. *Annu Rev Immunot.* 18:423.
Stafford & Rose. 2000. *Int Rev Immunol.* 19:501.
Stassi et al., 2000. *Nat Immunol.* 1:483.
Stassi, G., and R. De Maria. 2002. *Nat Rev Immunol.* 2:195.
Thompson, C., and F. Powrie. 2004. *Curr Opin Pharmacol.* 4:408.
Tourneur et al., 2002. *Eur J Immunol.* 32:1292.
Vasu et al., 2003. *Autoimmunity.* 36:389.
Vasu et al., 2003. *J Immunol.* 170:5511.
Vincent et al., 2001. Myasthenia gravis. Lancet 357: 2122-2128.
Vincent, A. 2002. Nat. Rev. Inmunol. 2: 797-804.
Wakkach et al., 2003. *Immunity.* 18:605.
Wang et al., 2002. *J Immunol.* 168:2470.
Weetman &McGregor. 1994. *Endocr Rev.* 15:788.
Xiao et al., 2003. Cell. Inmunol. 223: 63-69.
Zhang et al., 2003. *Acta Pharmacol Sin.* 24:885.
Zhang et al., 2004. *Int Immunol.* 16:249.
Zhang, W., and Y. C. Kong. 1998. *Cell Immunol.* 187:95-102.
Zheng et al., 2004. *J Immunol.* 172:5213.

What is claimed is:

1. A composition comprising a semi-mature dendritic cell coated with a bispecific antibody, wherein the bispecific antibody binds to an antigenic surface molecule on a dendritic cell and to a T-cell receptor that suppresses T-cell activation.

2. The composition of claim 1, wherein the inhibitory T cell receptor is CTLA-4.

3. The composition of claim 1, wherein the dendritic cell is treated with GM-CSF to maintain semimature status.

4. The composition of claim 1, wherein the dendritic cell is pulsed with an antigen of interest.

5. A bispecific anti-CTLA-4 antibody that activates CTLA-4 signaling to suppress T-cell activation, wherein the antibody binds to CTLA-4 and also to a specific molecule on a dendritic cell surface.

6. The composition of claim 1, wherein the surface molecule is CD11 on dendritic cells.

7. The composition of claim 1, wherein dendritic cells are pulsed with a tissue specific antigen.

8. The bispecific antibody of claim 5, wherein the specific molecule on the dendritic cell is CD 11.

* * * * *

UNITED STATES PATENT AND TRADEMARK OFFICE
CERTIFICATE OF CORRECTION

PATENT NO. : 7,527,972 B2  Page 1 of 1
APPLICATION NO. : 11/560649
DATED : May 5, 2009
INVENTOR(S) : Prabhakar et al.

It is certified that error appears in the above-identified patent and that said Letters Patent is hereby corrected as shown below:

In Column 1, the paragraph beginning at line 18 should read as follows:

--This invention was made with government support under Grant Numbers 5 K08 01021-01, AI059745, AI058190, and AI073858, awarded by the National Institutes of Health. The U.S. government has certain rights in the invention.--

Signed and Sealed this

Sixteenth Day of March, 2010

David J. Kappos
*Director of the United States Patent and Trademark Office*